(12) United States Patent
Shiga et al.

(10) Patent No.: US 9,708,498 B2
(45) Date of Patent: Jul. 18, 2017

(54) AZO COMPOUND, INK CONTAINING AZO COMPOUND, DISPLAY INCLUDING SAID INK AND ELECTRONIC PAPER

(71) Applicant: MITSUBISHI CHEMICAL CORPORATION, Tokyo (JP)

(72) Inventors: Yasushi Shiga, Kanagawa (JP); Tomoko Kadowaki, Kanagawa (JP); Yuki Tanaka, Kanagawa (JP); Mitsuya Aoba, Kanagawa (JP); Mio Ishida, Kanagawa (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 17 days.

(21) Appl. No.: 14/723,256

(22) Filed: May 27, 2015

(65) Prior Publication Data

US 2015/0284581 A1  Oct. 8, 2015

Related U.S. Application Data

(63) Continuation of application No. PCT/JP2013/081931, filed on Nov. 27, 2013.

(30) Foreign Application Priority Data

Nov. 28, 2012 (JP) .................. 2012-260019
Nov. 28, 2012 (JP) .................. 2012-260020

(51) Int. Cl.
| | | |
|---|---|---|
| C09D 11/033 | (2014.01) | |
| C09D 11/037 | (2014.01) | |
| C09B 31/043 | (2006.01) | |
| C09B 31/14 | (2006.01) | |
| C09B 35/037 | (2006.01) | |
| G02B 26/00 | (2006.01) | |
| G02F 1/167 | (2006.01) | |
| C07D 333/38 | (2006.01) | |
| C09D 11/52 | (2014.01) | |
| G02B 26/02 | (2006.01) | |

(52) U.S. Cl.
CPC ............ *C09D 11/52* (2013.01); *C07D 333/38* (2013.01); *C09B 31/043* (2013.01); *C09B 31/14* (2013.01); *C09B 35/037* (2013.01); *C09D 11/033* (2013.01); *C09D 11/037* (2013.01); *G02B 26/02* (2013.01); *G02F 1/167* (2013.01); *G02B 26/005* (2013.01); *G02F 2001/1678* (2013.01)

(58) Field of Classification Search
CPC ... C09D 11/033; C09D 11/037; C09B 31/043; C09B 31/14; C09B 35/037; C07D 333/35; G02B 26/005; G02F 1/167

USPC .......... 106/31.5, 31.52, 31.44; 534/757, 761; 359/290, 296
See application file for complete search history.

(56) References Cited

U.S. PATENT DOCUMENTS

| | | | |
|---|---|---|---|
| 3,883,504 A | 5/1975 | Schickfluss et al. | |
| 4,621,136 A | 11/1986 | Imahori et al. | |
| 4,743,581 A | 5/1988 | Gregory | |
| 5,070,069 A | 12/1991 | Bradbury et al. | |
| 5,106,815 A | 4/1992 | Akada et al. | |
| 5,296,448 A | 3/1994 | Bradbury et al. | |
| 5,510,314 A | 4/1996 | Evans et al. | |
| 5,782,934 A | 7/1998 | Hall et al. | |
| 8,143,382 B2* | 3/2012 | Shiga ................ | C09D 11/037 106/31.5 |
| 8,747,537 B2* | 6/2014 | Shiga ................ | C09D 11/037 106/31.44 |
| 8,834,619 B2 | 9/2014 | Nagata et al. | |
| 8,999,050 B2* | 4/2015 | Ishida ................ | G02F 1/167 106/31.44 |
| 9,200,171 B2* | 12/2015 | Takeda ............... | C09B 31/043 |
| 2008/0225374 A1 | 9/2008 | Hayes et al. | |
| 2010/0292450 A1 | 11/2010 | Shiga et al. | |
| 2013/0188238 A1 | 7/2013 | Shiga et al. | |

FOREIGN PATENT DOCUMENTS

| | | |
|---|---|---|
| EP | 0492911 A | 7/1992 |
| JP | 48-87172 A | 11/1973 |
| JP | 57-109860 A | 7/1982 |
| JP | 57-111356 A | 7/1982 |
| JP | 57-125262 A | 8/1982 |
| JP | 57-125263 A | 8/1982 |
| JP | 57-145154 A | 9/1982 |
| JP | 59-145252 A | 8/1984 |
| JP | 62-87393 A | 4/1987 |
| JP | 63-270882 A | 11/1988 |
| JP | 02-150390 A | 6/1990 |
| JP | 03-65393 A | 3/1991 |
| JP | 03-256793 A | 11/1991 |
| JP | 04-278389 A | 10/1992 |
| JP | 08-267939 A | 10/1996 |

(Continued)

OTHER PUBLICATIONS

English translation of the Written Opinion of the International Search Authority mailed Jan. 21, 2013 for PCT/JP2013/081931; 11 pages.*
English translation of JP 2013/129697; Jul. 2013; 27 pages.*
Hayes et al. "Video-speed electronic paper based on electrowetting", *Nature*, Sep. 25, 2003, p. 383-385, vol. 425.
International Search Report mailed Jan. 21, 2014 for the corresponding PCT application No. PCT/JP2013/081931.

(Continued)

*Primary Examiner* — Helene Klemanski
(74) *Attorney, Agent, or Firm* — Leason Ellis LLP

(57) ABSTRACT

The present invention relates to an ink comprising: a solvent having a relative permittivity, measured at a frequency of 1 kHz and a temperature of 22° C., of 3 or less and a solubility in water at 25° C. of 20 mg/L or less; and a specific azo compound.

13 Claims, No Drawings

(56) References Cited

FOREIGN PATENT DOCUMENTS

| | | |
|---|---|---|
| JP | 09-508939 A | 9/1997 |
| JP | 10-119441 A | 5/1998 |
| JP | 2000-313174 A | 11/2000 |
| JP | 2005-213484 A | 8/2005 |
| JP | 2007-99823 A | 4/2007 |
| JP | 2007-531917 A | 11/2007 |
| JP | 2009-056711 A | 3/2009 |
| JP | 2009-138189 A | 6/2009 |
| JP | 2012-211293 A | 11/2012 |
| JP | 2013-129697 A | 7/2013 |
| WO | WO-2010-031860 A | 3/2010 |
| WO | WO-2012/033177 A | 3/2012 |
| WO | WO 2012/161098 A1 * | 11/2012 |

OTHER PUBLICATIONS

Office Action mailed Jul. 8, 2016 for the corresponding Chinese Patent Application No. 201380062256.9.
Office Action mailed Jan. 24, 2017 for the corresponding Chinese Patent Application No. 201380062256.9.

* cited by examiner

AZO COMPOUND, INK CONTAINING AZO COMPOUND, DISPLAY INCLUDING SAID INK AND ELECTRONIC PAPER

TECHNICAL FIELD

The present invention relates to an azo compound and an ink containing the azo compound. More particularly, the invention relates to an azo compound having a specific chemical structure and to an ink which includes an azo compound and a solvent and is useful as a display material or for optical shutters.

BACKGROUND ART

An electrowetting display is an image display system in which a plurality of pixels each filled with two phases, i.e., an aqueous medium and an oil-based coloring ink, is disposed on a substrate and the affinity at the aqueous-medium/substrate interface is controlled for each pixel by means of voltage application on-off switching to cause the oil-based coloring ink to spread/agglomerate on the substrate and thereby display an image (non-patent document 1). Colorants for use in electrowetting displays are required to have, for example, high solubility in lowly polar solvents (patent document 1 and patent document 2).

In patent documents 3 to 6 are shown dye colorants for polyester fibers, the dye colorants including a disazo compound having excellent fastness properties. In patent document 7 are shown a cyan colorant which is for use in thermal transfer sheets and which readily undergoes sublimation and/or thermal diffusion and an ink composition that employs the colorant. Media for ink preparation are mentioned therein.

PRIOR-ART DOCUMENTS

Patent Documents

Patent Document 1: JP-T-2007-531917 (the term "JP-T" as used herein means a published Japanese translation of a PCT patent application)
Patent Document 2: International Publication WO 2010/031860
Patent Document 3: JP-A-57-109860
Patent Document 4: JP-A-57-111356
Patent Document 5: JP-A-57-125262
Patent Document 6: JP-A-57-125263
Patent Document 7: JP-A-3-256793

Non-Patent Document

Non-Patent Document 1: Nature, (the United Kingdom), Vol. 425, pp. 383-385, 2003

SUMMARY OF THE INVENTION

Problems that the Invention is to Solve

However, any colorant having high solubility in lowly polar solvents and having a high extinction coefficient is not specifically shown in patent document 2.

Although patent documents 3 to 6 include statements concerning dye pigments and patent document 7 includes statements concerning colorants and media for ink preparation, no investigation has been made in these documents with respect to the solubility of colorants in solvents, in particular, solubility in lowly polar solvents having a relative permittivity not higher than a specific value.

An object of the invention is to provide an azo compound having excellent solubility in specific solvents, a high extinction coefficient, and excellent light fastness and an ink which contains the azo compound. Another object is to provide an ink which has an excellent hue, brings about excellent operation characteristics when used in displays or the like, and attains a high OD (optical density) value while having a reduced compound concentration therein and a reduced ink viscosity.

Means for Solving the Problems

The present inventors diligently made investigations in order to overcome the problems. As a result, the inventors have found that an azo compound having a certain chemical structure has excellent solubility in solvents and further has a high molar extinction coefficient and high light fastness and that an excellent hue and excellent operation characteristics are attained by using a specific solvent and the azo compound. The invention has been achieved on the bases of these findings.

Essential points of the invention reside in the following [1] to [15].

[1] An ink comprising: a solvent having a relative permittivity, measured at a frequency of 1 kHz and a temperature of 22° C., of 3 or less and a solubility in water at 25° C. of 20 mg/L or less; and an azo compound represented by the following general formula (1):

[Chem. 1]

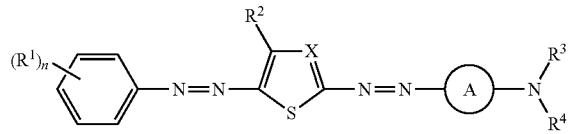

[In general formula (1),
$R^1$ represents any substituent,
$R^2$ represents a hydrogen atom or any substituent,
$R^3$ and $R^4$ each independently represent an alkyl group which may have a substituent,
ring A represents general formula (2) or (3),
when ring A is general formula (2), then X represents a nitrogen atom or a methine group which may have a substituent,
when ring A is general formula (3), then X represents a methine group having either a cyano group or an alkoxycarbonyl group which may have a substituent,
when ring A is general formula (3) and $R^2$ is a hydrogen atom, then X represents a methine group having an alkoxycarbonyl group which may have a substituent, and
n represents an integer of 0-5.]

[Chem. 2]

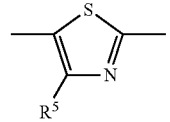

[In general formula (2), $R^5$ represents a hydrogen atom or any substituent.]

[Chem. 3]

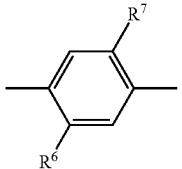

(3)

[In general formula (3), $R^6$ and $R^7$ each independently represent a hydrogen atom or any substituent.]

[2] The ink according to the [1], wherein the solvent comprises at least one member selected from hydrocarbon-based solvents, silicone oils, and fluorocarbon-based solvents.

[3] The ink according to the [1] or [2], wherein a product $\epsilon C$ of a molar extinction coefficient $\epsilon$ ($Lmol^{-1}$ $cm^{-1}$) at an absorption maximum wavelength in an n-decane solution of the azo compound and a saturation concentration C ($molL^{-1}$) at 5° C. of the solution is 1,000 $cm^{-1}$ or larger.

[4] The ink according to any one of the [1] to [3], which further comprises at least one member selected from the group consisting of heterocyclic compounds, cyanovinyl compounds, and anthraquinone compounds.

[5] The ink according to the [4], wherein the heterocyclic compounds are at least one compound selected from the group consisting of the following general formulae (4) to (7):

[Chem. 4]

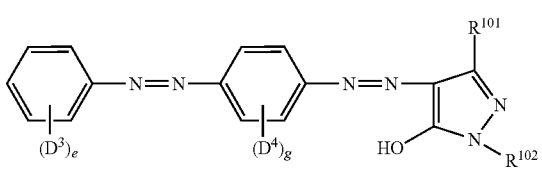

(4)

[In general formula (4), $R^{101}$ and $R^{102}$ each independently represent a hydrogen atom or any substituent, $D^3$ and $D^4$ each independently represent any substituent, e represents an integer of 0-5, and when e is 2 or larger, the two or more $D^3$s present in the molecule may be the same or different, and g represents an integer of 0-4, and when g is 2 or larger, the two or more $D^4$s present in the molecule may be the same or different.]

[Chem. 5]

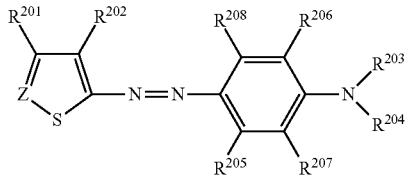

(5)

[In general formula (5), $R^{201}$, $R^{202}$, $R^{203}$, $R^{204}$, $R^{205}$, $R^{206}$, $R^{207}$, and $R^{208}$ each independently represent a hydrogen atom or any substituent, and Z represents a nitrogen atom or a methine group which may have a substituent.]

[Chem. 6]

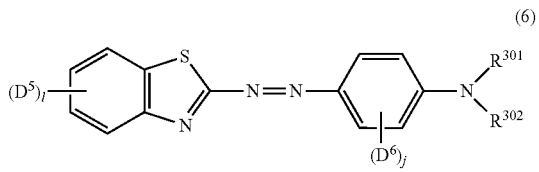

(6)

[In general formula (6), $R^{301}$, $R^{302}$, $D^5$, and $D^6$ each independently represent any substituent, l represents an integer of 0-4, and when l is 2 or larger, the two or more $D^5$s present in the molecule may be the same or different, and j represents an integer of 0-4, and when j is 2 or larger, the two or more $D^6$s present in the molecule may be the same or different.]

[Chem. 7]

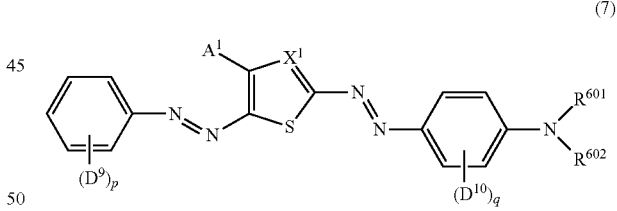

(7)

[In general formula (7), $R^{601}$, $R^{602}$, $D^9$, or $D^{10}$ each independently represents any substituent, $A^1$ represents a hydrogen atom or any substituent, p represents an integer of 0-5, and when p is 2 or larger, the two or more $D^9$s present in the molecule may be the same or different, q represents an integer of 0-4, and when q is 2 or larger, the two or more $D^{10}$s present in the molecule may be the same or different, $X^1$ represents a nitrogen atom or a methine group which may have a halogen atom, a cyano group, or a —$COOR^{605}$ group as a substituent, and $R^{605}$ represents a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.]

[6] The ink according to the [4] or [5], wherein the anthraquinone compounds are represented by the following general formula (8):

[Chem. 8]

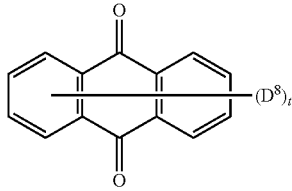

(8)

[In general formula (8), $D^8$ represents any substituent, and t represents an integer of 0-8, and when t is 2 or larger, the two or more $D^8$s present in the molecule may be the same or different.]

[7] The ink according to any one of the [1] to [6], which is for displays or for optical shutters.

[8] A display which comprises a display part including the ink according to any one of the [1] to [6], wherein an image is displayed by controlling voltage application to the display part.

[9] The display according to the [8], wherein the display part includes electrophoretic particles or an aqueous medium.

[10] The display according to the [8] or [9], wherein an image is displayed by causing a change in the coloration state by the voltage application.

[11] The display according to any one of the [8] to [10], wherein an image is displayed in an electrowetting mode or an electrophoresis mode.

[12] An electronic paper which comprises the display according to any one of the [8] to [11].

[13] An ink comprising: a solvent which has a relative permittivity, measured at a frequency of 1 kHz and a temperature of 22° C., of 3 or less and a solubility in water at 25° C. of 20 mg/L or less; and at least one of each of the following compounds (I) to (IV):

(I) compounds which have an absorption maximum wavelength in a decane solution thereof of 400 nm or larger and less than 500 nm, (II) compounds which have an absorption maximum wavelength in a decane solution thereof of 500 nm or larger and less than 570 nm, (III) disazo compounds which have an absorption maximum wavelength in a decane solution thereof of 570 nm or larger and less than 640 nm, (IV) compounds which have an absorption maximum wavelength in a decane solution thereof of 640 nm to 700 nm.

[14] An azo compound represented by the following general formula (10):

[Chem. 9]

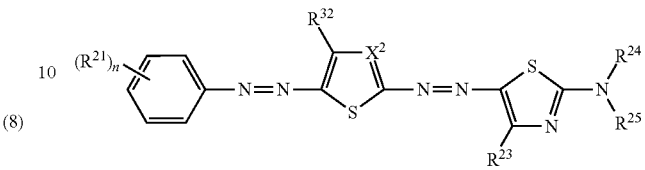

(10)

[In general formula (10), $R^{21}$ represents any substituent, $R^{22}$ and $R^{23}$ each independently represent a hydrogen atom or any substituent, $R^{24}$ and $R^{25}$ each independently represent an alkyl group which may have a substituent, $X^2$ represents a nitrogen atom or a methine group which may have a substituent, and n' represents an integer of 0-5.]

[15] An azo compound represented by the following general formula (11):

[Chem. 10]

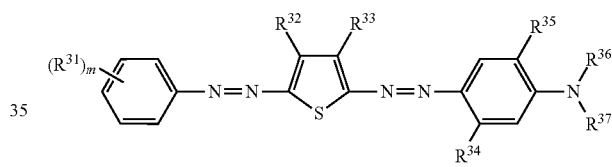

(11)

[In general formula (11), $R^{31}$ represents any substituent, $R^{32}$ represents a hydrogen atom or an alkyl group, $R^{33}$ represents a cyano group or an alkoxycarbonyl group, with the proviso that when $R^{32}$ is a hydrogen atom, $R^{33}$ represents an alkoxycarbonyl group, $R^{34}$ and $R^{35}$ each independently represent a hydrogen atom or any substituent, $R^{36}$ and $R^{37}$ each independently represent a branched alkyl group which has 4-20 carbon atoms and may have a substituent, and m represents an integer of 0-5.]

Effects of the Invention

The azo compounds of the invention and the inks containing the azo compounds combine high solubility especially in lowly polar solvents and a high molar extinction coefficient, are excellent in terms of hue and operation characteristics, and are hence useful in or as inks for use especially in displays and optical shutters. With respect to displays, the azo compounds and the inks are useful especially in displays which each have a display part including an ink and which are displays wherein voltage application to the display part is controlled to thereby display an image, or are displays wherein a change in coloration is caused by voltage application to thereby display an image, or are displays wherein electrophoretic particles or an aqueous medium is used in the display part to display an image.

Here, the electrophoretic particles are charged particles, and the particles may have a color. Multiple kinds of electrophoretic particles may be included in the display part. Meanwhile, the aqueous medium is a fluid which may have a color, and the display part may include multiple kinds of such aqueous media.

The azo compounds and inks of the invention are especially useful as inks for use in displays operated in an electrowetting mode or displays operated in an electrophoresis mode.

Furthermore, the inks of the invention can be provided as inks of different colors, including a satisfactory black ink with an excellent hue, by using the azo compounds of the invention in combination with other compound(s), and are useful also as a member which functions as an optical shutter.

Although usable in any display devices having a display, the inks of the invention are especially useful in electronic paper.

MODES FOR CARRYING OUT THE INVENTION

Representative embodiments for carrying out the invention are explained below in detail. However, the invention should not be construed as being limited to the following embodiments, and can be variously modified without departing from the spirit of the invention.

One of the inks of the invention is an ink including a solvent having a relative permittivity, measured at a frequency of 1 kHz and a temperature of 22° C., of 3 or less and a solubility in water at 25° C. of 20 mg/L or less and an azo compound represented by the following general formula (1).

[Chem. 11]

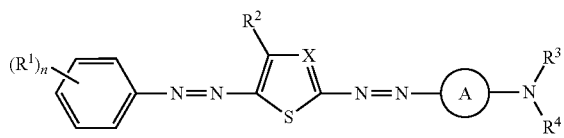

(1)

[In general formula (1), $R^1$ represents any substituent, $R^2$ represents a hydrogen atom or any substituent, $R^3$ and $R^4$ each independently represent an alkyl group which may have a substituent, ring A represents general formula (2) or (3), when ring A is general formula (2), then X represents a nitrogen atom or a methine group which may have a substituent, when ring A is general formula (3), then X represents a methine group having either a cyano group or an alkoxycarbonyl group which may have a substituent, when ring A is general formula (3) and $R^2$ is a hydrogen atom, then X represents a methine group having an alkoxycarbonyl group which may have a substituent, and n represents an integer of 0-5.]

[Chem. 12]

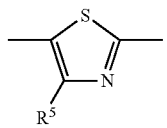

(2)

[In general formula (2),
$R^5$ represents a hydrogen atom or any substituent.]

[Chem. 13]

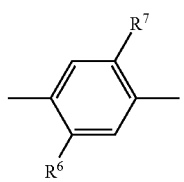

(3)

[In general formula (3),
$R^6$ and $R^7$ each independently represent a hydrogen atom or any substituent.]

(Solvent)

In displays and optical shutters to which this ink of the invention is applied, a lowly polar solvent is used as the solvent of the ink. The ink of the invention can be used, for example, in a display device which has layers such as an aqueous layer and an oily layer and which is based on the breaking-up or moving-aside of a layer. For displaying clear images, the oily layer which contains an ink is required to be immiscible with the aqueous layer and to stably break up or move aside. Because of this, the solvent is required to have low compatibility with water, low polarity, etc. According to the invention, since the ink includes a specific solvent and an azo compound, the oily layer can stably break up or move aside.

There are cases where in a device in which electrophoretic particles are used in a solvent to display an image, a high permittivity of the solvent inhibits the operation. Use of the specific solvent and azo compound according to the invention makes it possible to color a solvent without inhibiting the movement of particles.

The solvent to be used in the invention has a relative permittivity, measured at a frequency of 1 KHz and at 22° C., of 3 or less. The relative permittivity thereof is preferably 2.5 or less, more preferably 2.2 or less. Although there is no particular lower limit on the relative permittivity thereof, adequate values thereof are usually 1.5 and larger, preferably 1.8 and larger. For measuring the relative permittivity of a solvent, the method which will be shown in Examples is used. In the case where multiple solvents are mixed together and used as the solvent of the ink, the relative permittivity is the relative permittivity of the mixed solvent.

In cases when the ink-containing layer has a relative permittivity within an adequate range, the display device tends to be operated without raising difficulties. For example, in the case where the other layer, which contains no ink, is a liquid such as an electroconductive or polar liquid, e.g., water or a salt solution, layer mingling tends not to occur, when the relative permittivity of the solvent used in the ink-containing layer is within an adequate range.

The solvent to be used in the invention has a solubility in water at 25° C. of 20 mg/L or less. The solubility thereof is preferably 10 mg/L or less, more preferably 5 mg/L or less. Since the solubility in water is not higher than the specific value, there is, for example, a tendency that the oily layer does not mingle with the aqueous layer and the display device can be operated without raising difficulties.

For determining the solubility of a solvent in water, the method which will be shown in Examples is used. In the case where multiple solvents are mixed together and used as the solvent of the ink, the solubility in water is the solubility of the mixed solvent.

The boiling point of the solvent according to the invention is not particularly limited. However, the boiling point thereof is preferably 120° C. or higher, more preferably 150° C. or higher, especially preferably 170° C. or higher. It is also preferable that the boiling point thereof should be 300° C. or lower. In cases when the boiling point is not too high, this solvent has neither too high a melting point nor too high a viscosity and, when used in a display device, tends to bring about smooth operation. Furthermore, in cases when the boiling point is not too low, this solvent is less apt to volatilize and stability and safety tend to be obtained.

The viscosity of the solvent to be used in the invention is not particularly limited. It is, however, preferable that the solvent, when having a temperature of 25° C., should have a viscosity of 0.1 mPa·s or higher. The viscosity thereof is preferably 10,000 mPa·s or less, more preferably 1,000 mPa·s or less, especially preferably 100 mPa·s or less. In cases when the viscosity of the solvent is not too high, compounds and the like readily dissolve therein and this solvent, when used in a display device, tends to bring about smooth operation.

One solvent can be used alone, or solvents can be used as a mixture thereof. Examples thereof include hydrocarbon-based solvents, fluorocarbon-based solvents, and silicone oils.

Examples of the hydrocarbon-based solvents include linear or branched, aliphatic hydrocarbon solvents, alicyclic hydrocarbon solvents, aromatic hydrocarbon solvents, and petroleum naphtha.

Examples of the aliphatic hydrocarbon solvents and alicyclic hydrocarbon solvents include aliphatic hydrocarbon solvents such as n-decane, isodecane, decaline, nonane, dodecane, isododecane, tetradecane, hexadecane, and isoalkanes. Examples of commercial products thereof include Isopar E, Isopar G, Isopar H, Isopar L, and Isopar M (registered trademark; manufactured by Exxon Mobil Corp.), IP Solvent (registered trademark; manufactured by Idemitsu Petrochemical Co., Ltd.), and Soltol (manufactured by Phillips Petroleum International Ltd.).

Examples of the aromatic hydrocarbon solvents include alkylnaphthalenes and tetralin.

Examples of the petroleum naphtha solvent include Shell S.B.R., Shellsol 70, and Shellsol 71 (manufactured by Shell Sekiyu K.K.), Pegasol (manufactured by Exxon Mobil Corp.), and Hisol (manufactured by Nippon Oil Co., Ltd.).

The fluorocarbon-based solvents are hydrocarbons mainly substituted with fluorine, and examples thereof include perfluoroalkanes represented by $C_nF_{2n+2}$, such as $C_7F_{16}$ and $C_8F_{18}$. Commercial products thereof include Fluorinert PF5080 and Fluorinert PF5070 (manufactured by Sumitomo 3M Ltd.).

Examples of fluorochemical inert liquids include Fluorinert FC series (manufactured by Sumitomo 3M Ltd.). Examples of the fluorocarbons include Krytox GPL series (registered trademark; manufactured by DuPont Japan Ltd.).

Examples of chlorofluorocarbons include HCFC-141b (manufactured by Daikin Industries, Ltd.). Examples of iodofluorocarbons, such as $F(CF_2)_4CH_2CH_2I$ and $F(CF_2)_6I$, include 1-1420 and 1-1600 (manufactured by Daikin Fine Chemical Laboratory Co., Ltd.).

Examples of the silicone oils include low-viscosity synthetic demethylpolysoloxanes, and examples of the commercial products thereof include KF96L (manufactured by Shin-Etsu Silicones) and SH200 (manufactured by Dow Corning Tray Silicone Co., Ltd.).

It is preferable that the solvent should include at least one selected from the group consisting of hydrocarbon-based solvents, fluorocarbon-based solvents, and silicone oils. The content of these solvents, based on that solvent, is usually 50% by mass or higher, preferably 70% by mass or higher, more preferably 90% by mass or higher.

In the case of using a mixture of solvents, the relative permittivity of the mixed solvent can be approximated at a value obtained by multiplying the relative permittivity of each of the individual solvents that constitute the mixed solvent by the volume fraction thereof and summing up the resultant products, when the interaction between the solvents is slight as in the invention. Likewise, when the interaction between the solvents is slight, the solubility of the mixed solvent in water can be approximated at a value obtained by multiplying the solubility in water of each of the solvents that constitute the mixed solvent by the molar fraction thereof and summing up the resultant products.

The ink of the invention includes the specific solvent and an azo compound, and may be obtained by dissolving the azo compound and other compounds, additives, etc., which are used according to need, in the solvent.

Here, with regard to the term "dissolve", the azo compound need not have been completely dissolved in the solvent. The azo compound may be in such a state that the azo compound can pass through a filter of about 0.1 µm and that the extinction coefficient thereof can be measured. The compound may also be in the state of having been dispersed as fine particles thereof.

(Azo Compound Represented by General Formula (1))

With respect to the azo compound according to the invention, which has a structure represented by general formula (1), and $R^1$ to $R^7$, n, and X that are used in general formula (1), specific examples thereof are explained below.

<$R^1$>

$R^1$ represents any substituent. This substituent is not particularly limited so long as the substituent is a known substituent used in azo compounds. However, from the standpoints of high solubility in solvents and high extinction coefficient, specific examples thereof include: halogen atoms such as fluorine, chlorine, bromine, and iodine atoms; an alkyl group which has 1-20 carbon atoms and may have a substituent; an alkoxy group which has 1-20 carbon atoms and may have a substituent; and an alkoxycarbonyl group which has 2-21 carbon atoms and may have a substituent. Of these, the alkyl group which has 1-20 carbon atoms and may have a substituent is preferred from the standpoints of high solubility in solvents and high extinction coefficient.

(Alkyl Group which May have a Substituent)

Specific examples of the alkyl group which may have a substituent, as $R^1$, include alkyl groups which have 1-20 carbon atoms and may have a branched chain and a cyclic structure, such as methyl, ethyl, propyl, isopropyl, cyclopropyl, butyl, isobutyl, sec-butyl, tert-butyl, pentyl, cyclopentyl, hexyl, cyclohexyl, heptyl, octyl, 2-ethylhexyl, 3,5, 5-trimethylhexyl, decyl, and dodecyl. Preferred of these are ones having 2-20 carbon atoms. More preferred are ones having 2-10 carbon atoms. In cases when the number of carbon atoms is in an adequate range, the compound tends to be capable of having high solubility in solvents and a high extinction coefficient.

(Alkoxy Group which May have a Substituent)

Specific examples of the alkoxy group which may have a substituent, as $R^1$, include alkoxy groups which have 1-20 carbon atoms and may have a straight chain, a branched chain, and a cyclic structure, such as methoxy, ethoxy, propoxy, isopropoxy, cyclopropoxy, butoxy, isobutoxy, sec-butoxy, tert-butoxy, pentyloxy, cyclobutoxy, cyclopentyloxy, hexyloxy, cyclohexyloxy, heptyloxy, octyloxy, 2-ethylhexyloxy, 3,5,5-trimethylhexyloxy, decyloxy, and dodecyloxy. Preferred of these are ones having 2-20 carbon atoms. More preferred are ones having 2-10 carbon atoms. In cases when the number of carbon atoms is in an adequate range, the compound tends to be capable of having high solubility in solvents and a high extinction coefficient.

(Alkoxycarbonyl Group which May have a Substituent)

Specific examples of the alkoxycarbonyl group which may have a substituent, as $R^1$, include alkoxycarbonyl groups which have 2-21 carbon atoms and may have a branched chain and a cyclic structure, such as methoxycarbonyl, ethoxycarbonyl, propoxycarbonyl, isopropoxycarbonyl, cyclopropoxycarbonyl, butoxycarbonyl, isobutoxycarbonyl, sec-butoxycarbonyl, tert-butoxycarbonyl, cyclobutoxycarbonyl, pentyloxycarbonyl, cyclopentyloxycarbonyl, hexyloxycarbonyl, cyclohexyloxycarbonyl, heptyloxycarbonyl, octyloxycarbonyl, 2-ethylhexyloxycarbonyl, 3,5,5-trimethylhexyloxycarbonyl, decyloxycarbonyl, and dodecyloxycarbonyl. Preferred of these are ones having 3 or more carbon atoms and ones having 11 or less carbon atoms. In cases when the number of carbon atoms is in an adequate range, the compound tends to be capable of having high solubility in solvents and a high extinction coefficient.

The alkyl, alkoxy, and alkoxycarbonyl groups which may have a substituent, as $R^1$, may have any substituents. Examples of the substituents include: halogen atoms such as fluorine, chlorine, bromine, and iodine atoms; and alkoxy groups which have 1-20 carbon atoms and may have a branched chain and a cyclic structure, such as methoxy, ethoxy, propoxy, isopropoxy, cyclopropoxy, butoxy, isobutoxy, sec-butoxy, tert-butoxy, cyclobutoxy, pentyloxy, cyclopentyloxy, hexyloxy, cyclohexyloxy, heptyloxy, octyloxy, 2-ethylhexyloxy, 3,5,5-trimethylhexyloxy, decyloxy, and dodecyloxy.

<n>

Symbol n represents an integer of 0-5. It is preferable that n should by 0-3, in particular, 0-2. In the case where n is 2 or larger, the two or more Ws present in the molecule may be the same or different. The position at which each $R^1$ substituent has been bonded may be either ortho, meta, or para to the azo bond.

<$R^2$>

$R^2$ represents a hydrogen atom or any substituent. Although $R^2$ is not particularly limited unless the effects of the invention are lessened, it is preferable the $R^2$ should be a hydrogen atom or an alkyl group which has 1-20 carbon atoms and may have a substituent, or be a halogen atom, etc., from the standpoint of enabling the compound to have excellent solubility in solvents and a high molar extinction coefficient.

The term "alkyl group which may have a substituent" for $R^2$ has the same meaning as the alkyl group which may have a substituent shown above with regard to the $R^1$ contained in general formula (1), and the substituents which may be possessed are also the same. The number of carbon atoms of the alkyl group as $R^2$ is preferably 10 or less, more preferably 5 or less. In cases when the number of carbon atoms is in an adequate range, the compound tends to have excellent solubility in solvents and further have a high gram extinction coefficient.

<$R^3$ and $R^4$>

$R^3$ and $R^4$ each independently represent an alkyl group which may have a substituent. The term "alkyl group which may have a substituent" for $R^3$ and $R^4$ has the same meaning as the alkyl group which may have a substituent shown above with regard to the $R^1$ contained in general formula (1), and the substituents which may be possessed are also the same.

The number of carbon atoms of each of the alkyl groups as $R^3$ and $R^4$ is preferably 2 or larger, more preferably 4 or larger, especially preferably 6 or larger, and is preferably 20 or less, more preferably 12 or less. In cases when the number of carbon atoms is in an adequate range, high solubility in solvents and a high extinction coefficient tend to be able to be obtained.

It is preferable that at least either of the alkyl groups represented by $R^3$ and $R^4$ should by a branched alkyl group. It is more preferable that the alkyl groups should be both branched alkyl groups. In cases when at least one of the alkyl groups has a branched structure, high solubility tends to be obtained.

<Ring A>

Ring A represents general formula (2) or (3).

[Chem. 14]

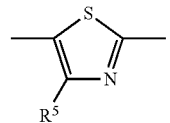

(2)

[In general formula (2),
$R^5$ represents a hydrogen atom or any substituent.]

[Chem. 15]

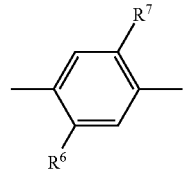

(3)

[In general formula (3),
$R^6$ and $R^7$ each independently represent a hydrogen atom or any substituent.]

<$R^5$>

$R^5$ represents a hydrogen atom or any substituent. $R^5$ is not particularly limited so long as $R^5$ is a known substituent to be used in the coupler moieties of azo compounds. However, from the standpoints of high solubility in solvents and high extinction coefficient, examples thereof include a hydrogen atom, an alkyl group which has 1-20 carbon atoms and may have a substituent, an acylamino group which has 1-20 carbon atoms and may have a substituent, and an alkylsulfonylamino group which has 1-20 carbon atoms and may have a substituent.

It is preferable that $R^5$ should be an alkyl group which has 1-20 carbon atoms and may have a substituent or an acylamino group which has 1-20 carbon atoms and may have a substituent, among those, because high solubility in solvents and a high extinction coefficient are obtained thereby.

(Acylamino Group which May have a Substituent)

Specific examples of the acylamino group which may have a substituent, as $R^5$, include acylamino groups which have 1-20 carbon atoms and may have a branched chain and a cyclic structure, such as formylamino, acetylamino, propionylamino, butyrylamino, isobutyrylamino, cyclopropylcarbonylamino, valerylamino, isovalerylamino, pivaloylamino, hexanoylamino, cyclopentylcarbonylamino, heptanoylamino, cyclohexylcarbonylamino, octanoylamino, 2-ethylhexanoylamono, decanoylamino, and dodecanoylamino.

Preferred of these are ones having 2 or more carbon atoms, and are aliphatic acylamino groups having 10 or less, more preferably 6 or less, carbon atoms. In cases when the number of carbon atoms is in an adequate range, the compound tends to be capable of having high solubility in solvents and a high extinction coefficient.

(Alkylsulfonylamino Group which May have a Substituent)

Examples of the alkylsulfonylamino group which may have a substituent, as $R^5$, include alkylsulfonylamino groups which have 1-20 carbon atoms and may have a branched chain and a cyclic structure, such as methylsulfonylamino, ethylsulfonylamino, propylsulfonylamino, isopropylsulfonylamino, cyclopropylsulfonylamino, butylsulfonylamino, isobutylsulfonylamino, sec-butylsulfonylamino, tert-butylsulfonylamino, pentylsulfonylamino, cyclopentylsulfonylamino, hexylsulfonylamino, cyclohexylsulfonylamino, heptylsulfonylamono, octylsulfonylamino, 2-ethylhexylsulfonylamono, 3,5,5-trimethylhexylsulfonylamino, decylsulfonylamino, and dodecylsulfonylamino.

Preferred of these are ones having 1-10 carbon atoms. More preferred are ones having 1-6 carbon atoms. In cases when the number of carbon atoms is in an adequate range, the compound tends to be capable of having high solubility in solvents and a high extinction coefficient.

The acylamino group and alkylsulfonylamino group which are represented by $R^5$ each independently may have any substituents. Examples of the substituents include: halogen atoms such as fluorine, chlorine, bromine, and iodine atoms; and alkoxy groups which have 1-20 carbon atoms and may have a branched chain and a cyclic structure, such as methoxy, ethoxy, propoxy, isopropoxy, cyclopropoxy, butoxy, isobutoxy, sec-butoxy, tert-butoxy, cyclobutoxy, pentyloxy, cyclopentyloxy, hexyloxy, cyclohexyloxy, heptyloxy, octyloxy, 2-ethylhexyloxy, 3,5,5-trimethylhexyloxy, decyloxy, and dodecyloxy.

<$R^6$>

$R^6$ represents a hydrogen atom or any substituent. This substituent is not particularly limited so long as the substituent is a known substituent to be used in the coupler moieties of azo compounds. However, from the standpoints of high solubility in solvents and high extinction coefficient, examples thereof include: halogen atoms such as fluorine, chlorine, bromine, and iodine atoms; an alkyl group which has 1-20 carbon atoms and may have a substituent; an alkoxy group which has 1-20 carbon atoms and may have a substituent; an acylamino group which has 1-20 carbon atoms and may have a substituent; and an alkylsulfonylamino group which has 1-20 carbon atoms and may have a substituent.

It is preferable that $R^6$ should be an alkyl group which has 1-20 carbon atoms and may have a substituent, an alkoxy group which has 1-20 carbon atoms and may have a substituent, or an acylamino group which has 1-20 carbon atoms and may have a substituent, among those groups, because this compound tends to have high solubility in solvents and a high extinction coefficient.

(Acylamino Group which May have a Substituent)

The term "acylamino group which may have a substituent" for $R^6$ has the same meaning as the acylamino group which may have a substituent shown above with regard to the $R^5$ contained in general formula (2), and the substituents which may be possessed are also the same.

Preferred of these are aliphatic acylamino groups having 2-10 carbon atoms. More preferred are aliphatic acylamino groups having 2-6 carbon atoms. In cases when the number of carbon atoms is in an adequate range, the compound tends to be capable of having high solubility in solvents and a high extinction coefficient.

(Alkylsulfonylamino Group which May have a Substituent)

The term "alkylsulfonylamino group which may have a substituent" for $R^6$ has the same meaning as the alkylsulfonylamino group which may have a substituent shown above with regard to the $R^5$ contained in general formula (2), and the substituents which may be possessed are also the same.

Preferred of these are ones having one or more carbon atoms, and are ones having 10 or less, more preferably 6 or less, carbon atoms. In cases when the number of carbon atoms is in an adequate range, the compound tends to be capable of having high solubility in solvents and a high extinction coefficient.

<X>

In the case where ring A is general formula (2), X represents a nitrogen atom or a methine group which may have a substituent. In the case where ring A is general formula (3), X represents a methine group having either a cyano group or an alkoxycarbonyl group which may have a substituent. In the case where ring A is general formula (3) and $R^2$ is a hydrogen atom, X represents a methine group having an alkoxycarbonyl group which may have a substituent.

The substituent which the methine group may have is not particularly limited. However, it is preferable that the substituent should be a cyano group or an alkoxycarbonyl group which may have a substituent, from the standpoint of obtaining high solubility in solvents and a high molar extinction coefficient.

The term "alkoxycarbonyl group which may have a substituent" has the same meaning as the alkoxycarbonyl group which may have a substituent shown above with regard to the $R^1$ contained in general formula (1), and the substituents which may be possessed are also the same. Preferred of these are ones having 2-7 carbon atoms. In cases when the number of carbon atoms is in an adequate range, the compound tends to be capable of having high solubility in solvents and a high extinction coefficient.

<$R^7$>

$R^7$ represents a hydrogen atom or any substituent. This substituent is not particularly limited so long as the substituent is a known substituent to be used in the coupler moieties of azo compounds. However, from the standpoints of high solubility in solvents and high extinction coefficient, examples thereof include a hydrogen atom, an alkyl group which has 1-20 carbon atoms and may have a substituent, and an alkoxy group which has 1-20 carbon atoms and may have a substituent. It is preferable that $R^7$ should be a hydrogen atom or an alkoxy group which has 1-20 carbon atoms and may have a substituent, because this compound tends to have high solubility in solvents and a high extinction coefficient.

(Alkyl Group which May have a Substituent)

The term "alkyl group which may have a substituent" for $R^5$, $R^6$, and $R^7$ has the same meaning as the alkyl group which may have a substituent, examples of which were shown above with regard to the $R^1$ contained in general formula (1), and the substituents which may be possessed are also the same. The alkyl groups represented by $R^5$, $R^6$, and $R^7$ preferably are ones having one or more carbon atoms, and are ones having 10 or less, more preferably 6 or less, carbon atoms. In cases when the number of carbon atoms is in an adequate range, the compound tends to be capable of having high solubility in solvents and a high extinction coefficient.

(Alkoxy Group which May have a Substituent)

The term "alkoxy group which may have a substituent" for $R^6$ and $R^7$ has the same meaning as the alkoxy group which may have a substituent, examples of which were shown above with regard to the $R^1$ contained in general formula (1), and the substituents which may be possessed are also the same. Preferred of these are ones having 1-10 carbon atoms. More preferred are ones having 1-6 carbon atoms. In cases when the number of carbon atoms is in an adequate range, the compound tends to be capable of having high solubility in solvents and a high extinction coefficient.

Specific examples of the azo compound represented by general formula (1) are shown below. The invention should not be construed as being limited to the following examples unless the invention departs from the spirit thereof.

<Compounds in which Ring A is Represented by General Formula (2)>

[Chem. 16]

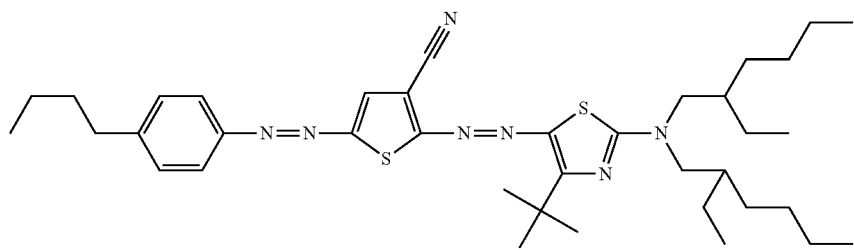

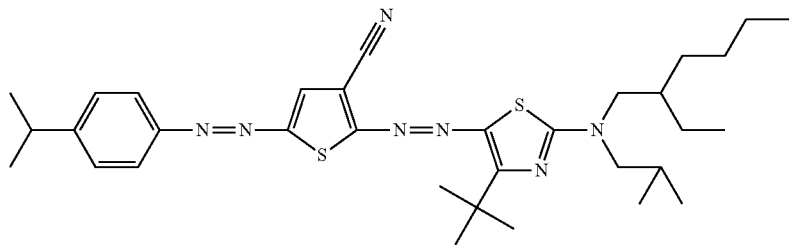

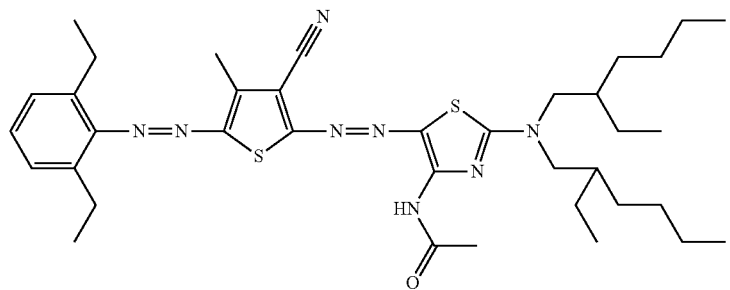

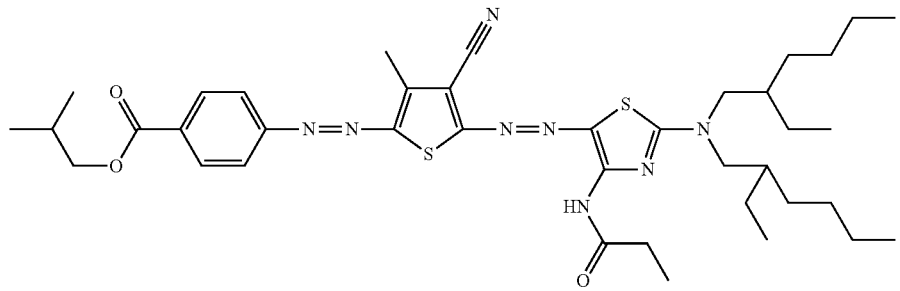

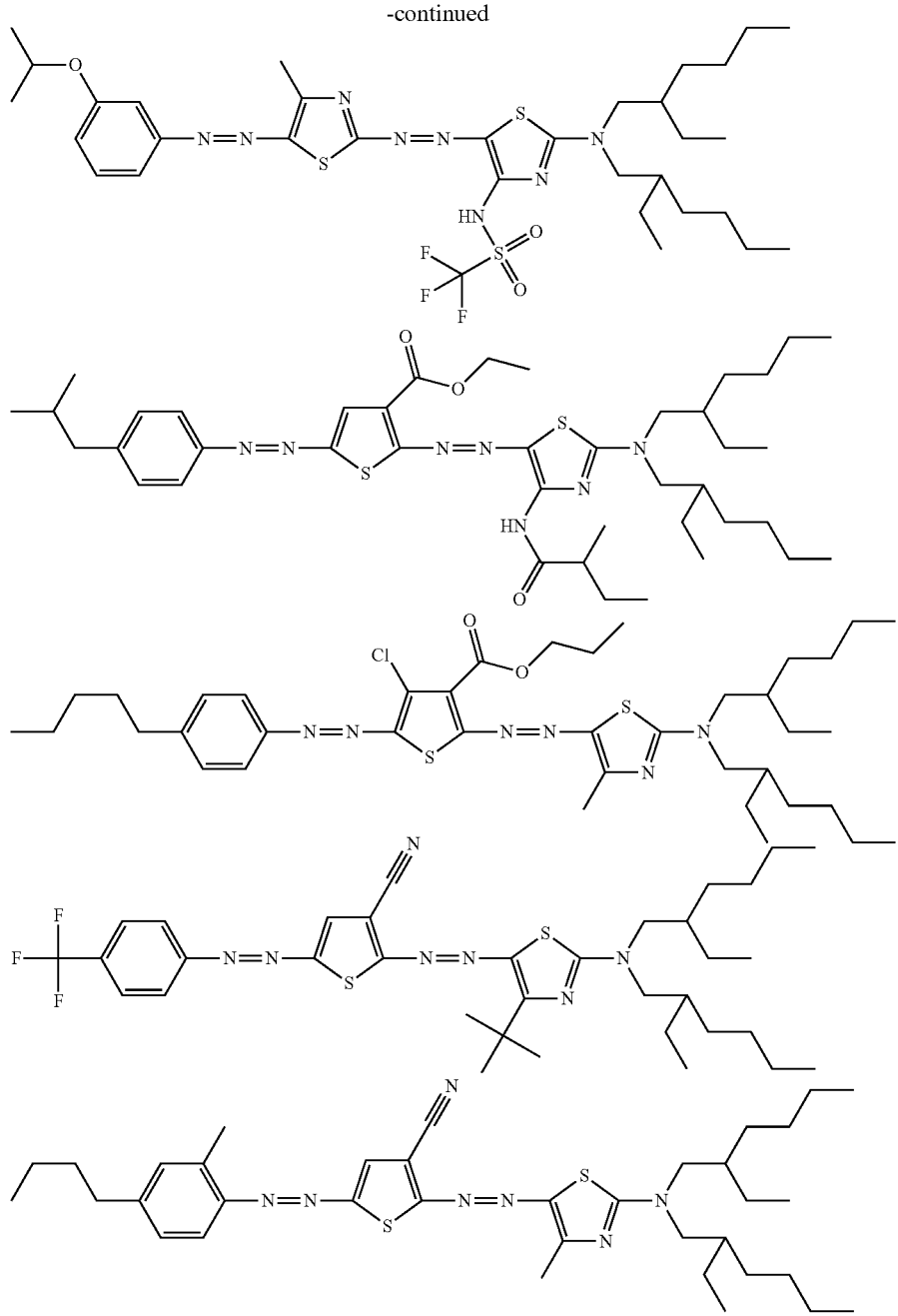
<Compounds in which Ring A is Represented by General Formula (3)>
[Chem. 17]
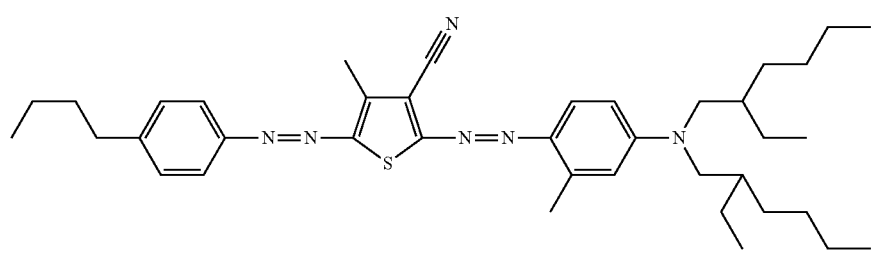

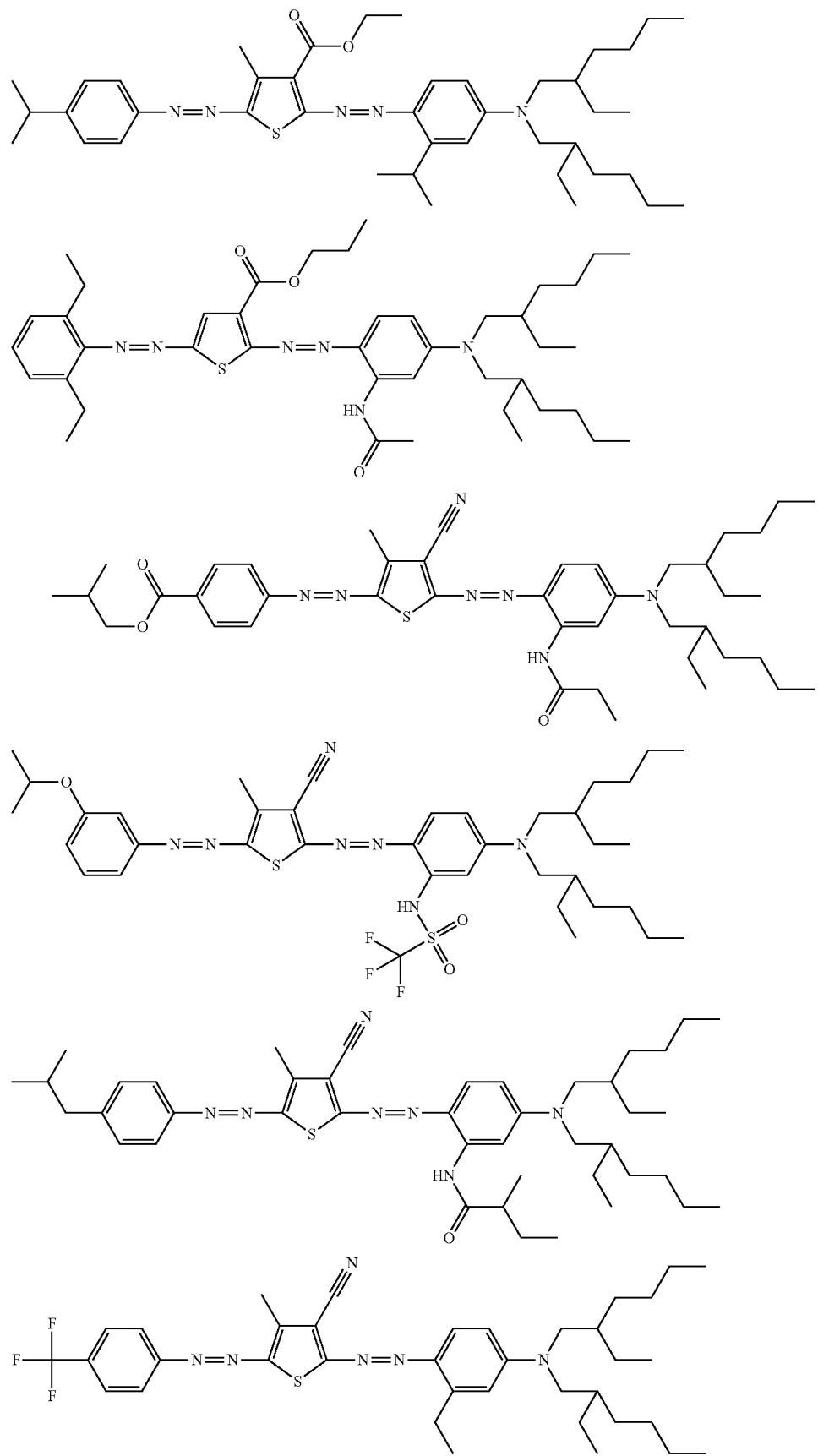

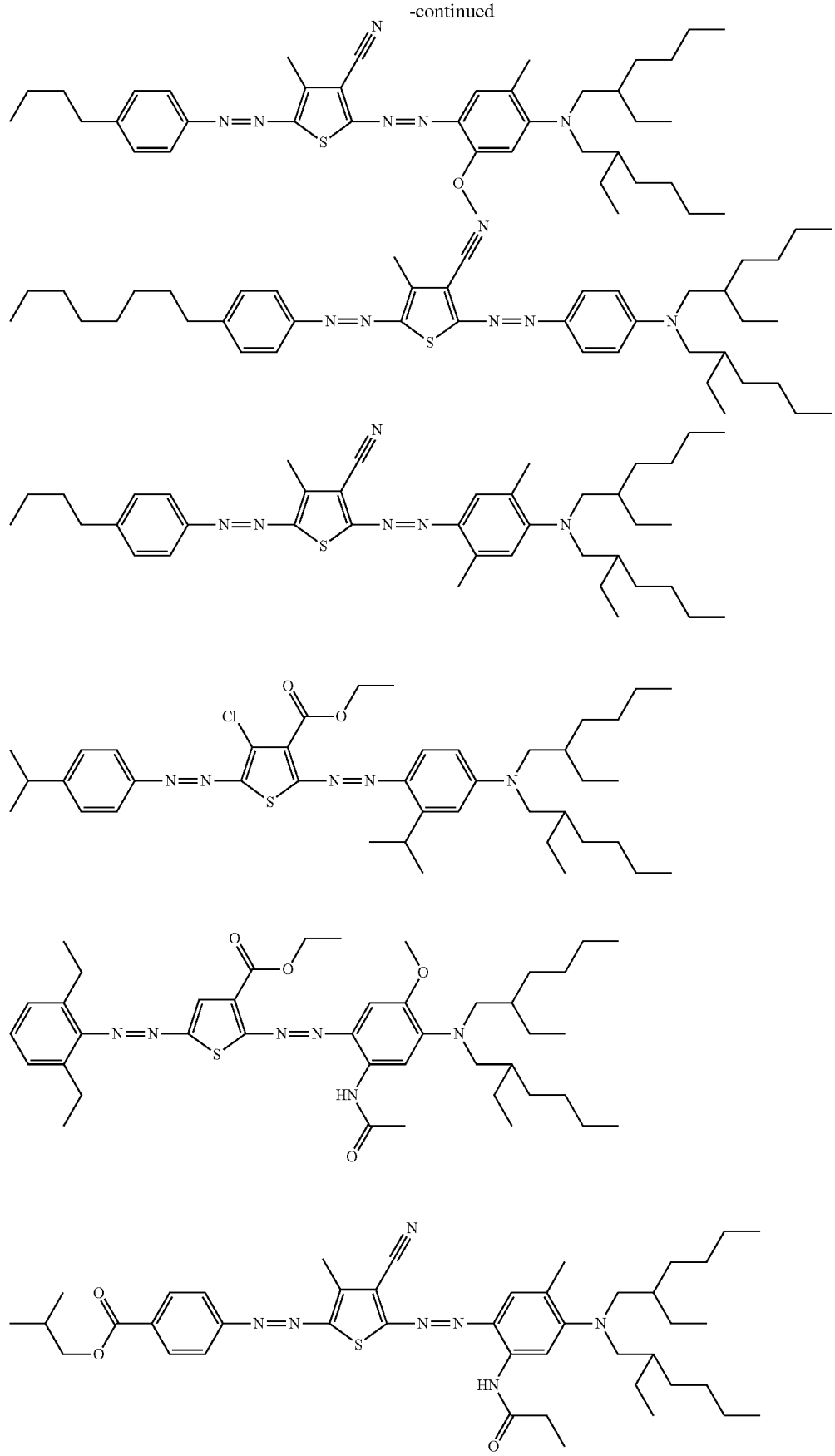

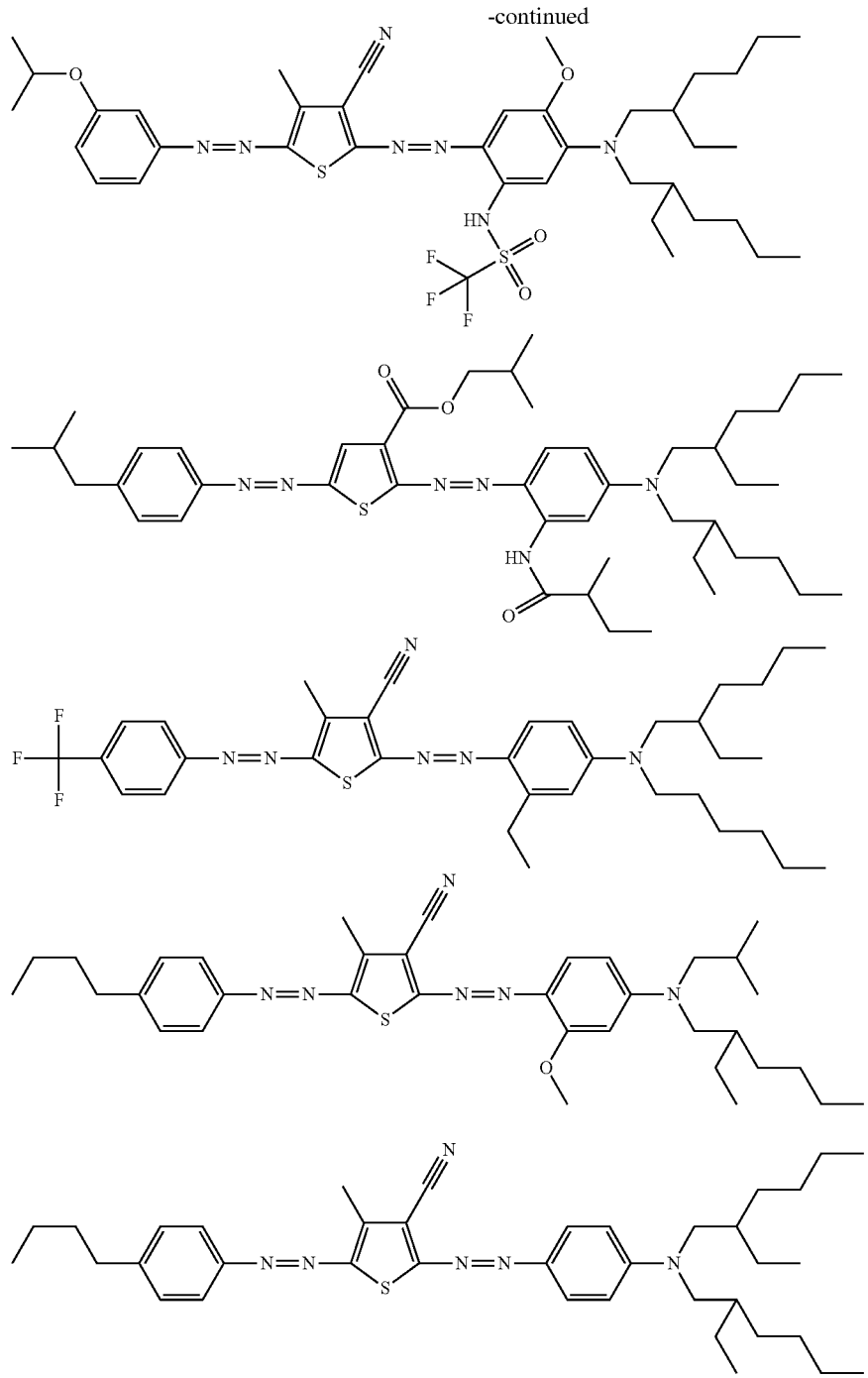

-continued

The molecular weight of the azo compound of the invention, including the substituents in the case where the compound has substituents, is preferably 3,000 or less, more preferably 1,500 or less. The molecular weight thereof is preferably 350 or higher. In cases when the molecular weight thereof is within an adequate range, a satisfactory gram extinction coefficient can be obtained.

The compound represented by general formula (1) wherein ring A is represented by general formula (2) can be synthesized, for example, by diazotizing a compound represented by general formula (12) and subjecting the diazotized compound to a coupling reaction with a compound represented by general formula (13).

[Chem. 18]

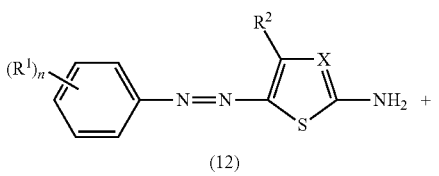

(12)

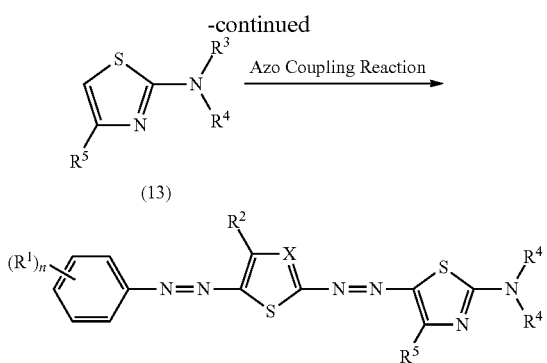

(13)

The substituents in general formulae (12) and (13) have the same meanings as those shown above with regard to general formulae (1) and (2).

The compound represented by general formula (1) wherein ring A is represented by general formula (3) can be synthesized, for example, by diazotizing a compound represented by general formula (14) and subjecting the diazotized compound to a coupling reaction with a compound represented by general formula (15).

[Chem. 19]

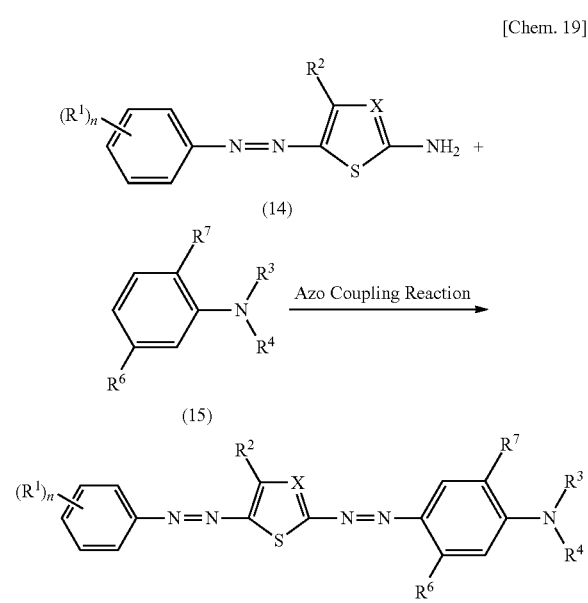

The substituents in general formulae (14) and (15) have the same meanings as those shown above with regard to general formulae (1) and (3).

The azo compound of the invention is characterized by having excellent solubility in solvents, in particular, in solvents which have a relative permittivity of 3 or less and have a solubility in water at 25° C. of 20 mg/L or less.

The azo compound of the invention has a solubility in 5° C. n-decane of usually 1% by mass or higher, preferably 3% by mass or higher, more preferably 5% by mass or higher. The higher the solubility, the more the compound is preferred. Usually, however, the solubility of the compound is up to about 80% by mass. There are cases where the azo compound can be used for displaying images on display devices such as displays, when the solubility thereof is not less than a specific value.

It is preferable that in the case of using the azo compound of the invention in electrowetting displays, the azo compound should be water-insoluble, in view of the principle of the displays. The term "water-insoluble" herein means that the solubility in water, under the conditions of 25° C. and 1 atm, is 0.1% by mass or less, preferably 0.01% by mass or less.

The molar extinction coefficient thereof is preferably 10,000 (L·mol$^{-1}$·cm$^{-1}$) or higher, and is more preferably 40,000 (L·mol$^{-1}$·cm$^{-1}$) or higher, from the standpoint of satisfying the performance of the display device.

Furthermore, the value of the product $\epsilon$ C of the molar extinction coefficient $\epsilon$ (L·mol$^{-1}$ cm$^{-1}$) at an absorption maximum wavelength of an n-decane solution of the azo compound of the invention and the saturation concentration C (mol·L$^{-1}$) at 5° C. of the azo compound in n-decane is preferably 1,000 cm$^{-1}$ or larger, more preferably 2,000 cm$^{-1}$ or larger. The larger the value of $\epsilon$ C, the higher the coloring properties and the more the azo compound is hence preferred. Although there is no particular upper limit, the value of $\epsilon$C is usually 100,000 cm$^{-1}$ or less.

With respect to the concentration of the azo compound in the ink of the invention, the ink is prepared so as to have any desired concentration in accordance with the intended use thereof. For example, in the case of use as a colorant for electrowetting displays, the azo compound is diluted, before use, with a nonpolar solvent usually to a concentration of 1% by mass or higher, in accordance with a required concentration. However, the concentration thereof is preferably 3% by mass or higher, more preferably 5% by mass or higher. Preferably, the concentration thereof is usually about 80% by mass or less.

The ink of the invention may contain one compound alone which is the azo compound described above, or may contain any desired two or more compounds in combination which each are the azo compound described above, in any desired proportion.

Since the azo compound of the invention has excellent solubility in solvents and has a high extinction coefficient, the azo compound is useful as a material for optical shutters and a material for displays, in particular, as a material for electrowetting displays and a material for electrophoretic displays.

There is no particular lower limit on the viscosity at 25° C. of the ink of the invention. However, the viscosity at 25° C. thereof is usually preferably 0.1 mPa·s or higher. Meanwhile, the upper limit thereof is preferably 10,000 mPa·s or less, more preferably 1,000 mPa·s or less, especially preferably 100 mPa·s or less. In case where the ink has too high a viscosity, this ink may raise difficulties in operating the display device.

With respect to the relative permittivity and viscosity of the solvent according to the invention and those of the ink, which includes the solvent, the colorant, etc., it is preferable that the difference between the solvent and the ink in each of these properties should be smaller because influences to be exerted on the operation characteristics when the ink is used in a display device or the like are reduced. Consequently, although the ink of the invention may contain any additives suitable for applications according to need so long as the effects of the invention are not lessened thereby, it is preferred to keep the properties of the solvent unchanged.

<Other Compounds>

The ink of the invention may contain the azo compound of the invention alone, or may further contain one or more other compounds in order to obtain a desired color tone. For example, the azo compound of the invention may be mixed with compounds of multiple colors, e.g., yellow, red, blue, purple, and orange, to obtain various colors including black.

Such other compounds which the ink of the invention may contain can be selected at will from compounds which have solubility or dispersibility in the solvent to be used, so long as the effects of the invention are not lessened thereby.

In the case where the ink of the invention is to be used for electrowetting displays, any desired compounds can be selected and used as those other compounds. Examples thereof include nitroso compounds, nitro compounds, monoazo compounds, disazo compounds, triazo compounds, polyazo compounds, stilbene compounds, carotenoid compounds, diarylmethane compounds, triarylmethane compounds, xanthene compounds, acridine compounds, quinoline compounds, methine compounds, thiazole compounds, isothiazole compounds, indamine compounds, indophenol compounds, azine compounds, oxazine compounds, thiazine compounds, heterocyclic compounds, sulfur dyes, lactone compounds, hydroxyketone compounds, aminoketone compounds, anthraquinone compounds, indigo compounds, phthalocyanine compounds, pyrazole compounds, cyanovinyl compounds, natural dyes, oxidation dyes, inorganic pigments, metal complexes, and carbon blacks.

Specific examples thereof include Oil Blue N (alkylamine-substituted anthraquinone), Solvent Green, Solvent Blue, Sudan Blue, Sudan Red, Sudan Yellow, Sudan Black, Disperse Violet, Disperse Red, Disperse Blue, Disperse Yellow, the compounds shown in International Publication WO 2009/063880, the compounds shown in International Publication WO 2010/031860, the compounds shown in International Publication WO 2012/033177, and the compounds shown in JP-A-57-125263.

Although the ink according to the invention is not particularly limited, it is preferable that the ink should contain at least one compound selected from the group consisting of heterocyclic compounds, cyanovinyl compounds, and anthraquinone compounds among those compounds. By combining these compounds at will, inks of various colors including a preferred black color can be rendered possible.

Specific examples of the heterocyclic compounds are not particularly limited. However, it is preferable that the heterocyclic compounds should be at least one compound selected from the group consisting of general formulae (4) to (7) which will be described later.

Examples of the heterocyclic compounds include compounds represented by the following general formula (4).

[Chem. 20]

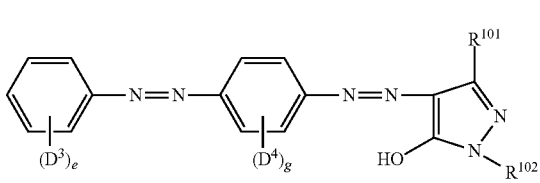

(4)

[In general formula (4),
$R^{101}$ and $R^{102}$ each independently represent a hydrogen atom or any substituent,
$D^3$ and $D^4$ each independently represent any substituent,
e represents an integer of 0-5, and when e is 2 or larger, the two or more $D^3$s present in the molecule may be the same or different, and
g represents an integer of 0-4, and when g is 2 or larger, the two or more $D^4$s present in the molecule may be the same or different.]

<$R^{101}$ and $R^{102}$>
$R^{101}$ and $R^{102}$ each independently represent a hydrogen atom or any substituent. Examples of the substituent represented by $R^{101}$ include a hydrogen atom, alkyl groups which have 1-20 carbon atoms and may have a substituent, alkoxy groups which have 1-20 carbon atoms and may have a substituent, aryl groups which have 6-20 carbon atoms and may have a substituent, heteroaryl groups which have 2-20 carbon atoms and may have a substituent, a —COOR$^{103}$ group, an —NR$^{107}$R$^{108}$ group, or a —COR$^{112}$ group. In cases when $R^{101}$ is any of the atom and substituents, high solubility in solvents and a high extinction coefficient tend to be obtained.

Examples of the substituent represented by $R^{102}$ include a hydrogen atom, alkyl groups which have 1-20 carbon atoms and may have a substituent, aryl groups which have 6-20 carbon atoms and may have a substituent, or heteroaryl groups which have 2-20 carbon atoms and may have a substituent. When $R^{102}$ is any of the atom and substituents, high solubility in solvents and a high extinction coefficient tend to be obtained.

<$R^{103}$, $R^{107}$, $R^{108}$, and $R^{112}$>
$R^{103}$, $R^{107}$, $R^{108}$, and $R^{112}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)
The term "alkyl group which may have a substituent" for $R^{101}$, $R^{102}$, $R^{103}$, $R^{107}$, $R^{108}$, and $R^{112}$ specifically has the same meaning as the alkyl group which may have a substituent, examples of which were shown above with regard to the $R^1$ contained in general formula (1), and the substituents which may be possessed are also the same.

The number of carbon atoms of each of the alkyl groups represented by $R^{102}$, $R^{103}$, $R^{107}$, $R^{108}$, and $R^{112}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)
The aryl group which may have a substituent that is represented by each of $R^{101}$, $R^{102}$, $R^{103}$, $R^{107}$, $R^{108}$, and $R^{112}$ is a group obtained by removing one hydrogen atom from a monocycle or from a fused ring made up of two to four monocycles fused together.

Specific examples thereof include groups obtained from a benzene ring, naphthalene ring, anthracene ring, phenanthrene ring, perylene ring, tetracene ring, pyrene ring, benzpyrene ring, chrysene ring, triphenylene ring, acenaphthene ring, fluoranthene ring, fluorene ring, and the like.

(Heteroaryl Group which May have a Substituent)
The heteroaryl group which may have a substituent that is represented by each of $R^{101}$, $R^{102}$, $R^{103}$, $R^{107}$, $R^{108}$, and $R^{112}$ is a group obtained by removing one hydrogen atom from a monocycle or from a fused ring made up of two to four monocycles fused together.

Specific examples thereof include groups obtained from a furan ring, benzofuran ring, thiophene ring, benzothiophene ring, pyrrole ring, pyrazole ring, imidazole ring, oxadiazole ring, indole ring, carbazole ring, pyrroloimidazole ring, pyrrolopyrazole ring, pyrrolopyrrole ring, thienopyrrole ring, thienothiophene ring, furopyrrole ring, furofuran ring, thienofuran ring, benzisooxazole ring, benzisothiazole ring, benzimidazole ring, pyridine ring, pyrazine ring, pyridazine ring, pyrimidine ring, triazine ring, quinoline ring, isoquinoline ring, cinnoline ring, quinoxaline ring, phenanthridine ring, benzimidazole ring, perimidine ring, quinazoline ring, quinazolinone ring, azulene ring, and the like.

The substituents which may be possessed by the aryl groups and heteroaryl groups represented by $R^{104}$, $R^{102}$, $R^{103}$, $R^{107}$, $R^{108}$, and $R^{112}$ are not particularly limited. Specific examples thereof include halogen atoms, alkyl groups having 1-20 carbon atoms, alkoxy groups having 1-20 carbon atoms, or alkoxycarbonyl groups having 1-20 carbon atoms.

(Alkoxy Group which May have a Substituent)

The term "alkoxy group which may have a substituent" for $R^{100}$ and $R^{102}$ specifically has the same meaning as the alkoxy group which may have a substituent, examples of which were shown above with regard to the $R^1$ contained in general formula (1), and the substituents which may be possessed are also the same.

The number of carbon atoms of each of the alkoxy groups represented by $R^{101}$ and $R^{102}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

<$D^3$>

$D^3$ represents any substituent. $D^3$ is not particularly limited unless the effects of the invention are lessened thereby. However, from the standpoints of high solubility in solvents and high extinction coefficient, it is preferable that $D^3$ should be a halogen atom, an alkyl group which has 1-20 carbon atoms and may have a substituent, an alkoxy group which has 1-20 carbon atoms and may have a substituent, a cyano group, a hydroxy group, a —$COOR^{104}$ group, an —NHCOR$^{109}$ group, an —NHSO$_2$R$^{110}$ group, a —COR$^{113}$ group, or an —OCOR$^{115}$ group.

Symbol e represents an integer of 0-5. When e is 2 or larger, the two or more $D^3$s present in the molecule may be the same or different.

<$R^{104}$, $R^{109}$, $R^{110}$, $R^{113}$, and $R^{115}$>

$R^{104}$, $R^{109}$, $R^{110}$, $R^{113}$, and $R^{115}$ each independently represent an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for $D^3$, $R^{104}$, $R^{109}$, $R^{110}$, $R^{113}$, and $R^{115}$ specifically has the same meaning as the alkyl group which may have a substituent, examples of which were shown above with regard to the $R^1$ contained in general formula (1), and the substituents which may be possessed are also the same.

The number of carbon atoms of each of the alkyl groups represented by $D^3$, $R^{104}$, $R^{109}$, $R^{110}$, $R^{113}$, and $R^{115}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group which may have a substituent" for $D^3$ has the same meaning as the alkoxy group which may have a substituent, examples of which were shown above with regard to the $R^1$ contained in general formula (1), and the substituents which may be possessed are also the same.

The number of carbon atoms of the alkoxy group represented by $D^3$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group which may have a substituent" for $R^{104}$, $R^{109}$, $R^{110}$, $R^{113}$, and $R^{115}$ specifically has the same meaning as the aryl group which may have a substituent, examples of which were shown above with regard to $R^{101}$, and the substituents which may be possessed are also the same as those of the aryl group which were shown above as examples with regard to $R^{101}$.

(Heteroaryl Group which May have a Substituent)

The term "heteroaryl group" for $R^{104}$, $R^{109}$, $R^{110}$, $R^{113}$, and $R^{115}$ specifically has the same meaning as the heteroaryl group, examples of which were shown above with regard to $R^{101}$, and the substituents which may be possessed are also the same as those of the heteroaryl group which were shown above as examples with regard to $R^{101}$.

<$D^4$>

$D^4$ represents any substituent. $D^4$ is not particularly limited unless the effects of the invention are lessened thereby. However, from the standpoints of high solubility in solvents and high extinction coefficient, it is preferable that $D^4$ should be a halogen atom, an alkyl group which has 1-20 carbon atoms and may have a substituent, an alkoxy group which has 1-20 carbon atoms and may have a substituent, a cyano group, a —COOR$^{105}$ group, an —NHCOR$^{106}$ group, an —NHSO$_2$R$^{111}$ group, or a —COR$^{114}$ group.

Symbol g represents an integer of 0-4. When g is 2 or larger, the two or more $D^4$s present in the molecule may be the same or different.

<$R^{105}$, $R^{106}$, $R^{111}$, and $R^{114}$>

$R^{105}$, $R^{106}$, $R^{111}$, and $R^{114}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for $D^4$, $R^{105}$, $R^{106}$, $R^{111}$, and $R^{114}$ specifically has the same meaning as the alkyl group which may have a substituent, examples of which were shown above with regard to the $R^1$ contained in general formula (1), and the substituents which may be possessed are also the same.

The number of carbon atoms of each of the alkyl groups represented by $D^4$, $R^{105}$, $R^{106}$, $R^{111}$, and $R^{114}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group which may have a substituent" for $D^4$ has the same meaning as the alkoxy group which may have a substituent, examples of which were shown above with regard to the $R^1$ contained in general formula (1), and the substituents which may be possessed are also the same. The number of carbon atoms of the alkoxy group represented by $D^4$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group which may have a substituent" for $R^{105}$, $R^{106}$, $R^{111}$ and $R^{114}$ specifically has the same meaning as the aryl group which may have a substituent, examples of which were shown above with regard to $R^{101}$, and the substituents which may be possessed are also the same as those of the aryl group which were shown above as examples with regard to $R^{101}$.

(Heteroaryl Group which May have a Substituent)

The term "heteroaryl group which may have a substituent" for $R^{105}$, $R^{106}$, $R^{111}$, and $R^{114}$ specifically has the same meaning as the heteroaryl group which may have a substituent, examples of which were shown above with regard to $R^{101}$, and the substituents which may be possessed are also the same as those of the heteroaryl group which were shown above as examples with regard to $R^{101}$.

Specific examples of the compounds represented by general formula (4) are shown below. However, the invention should not be construed as being limited to the following examples unless the invention departs from the spirit thereof.

[Chem. 21]

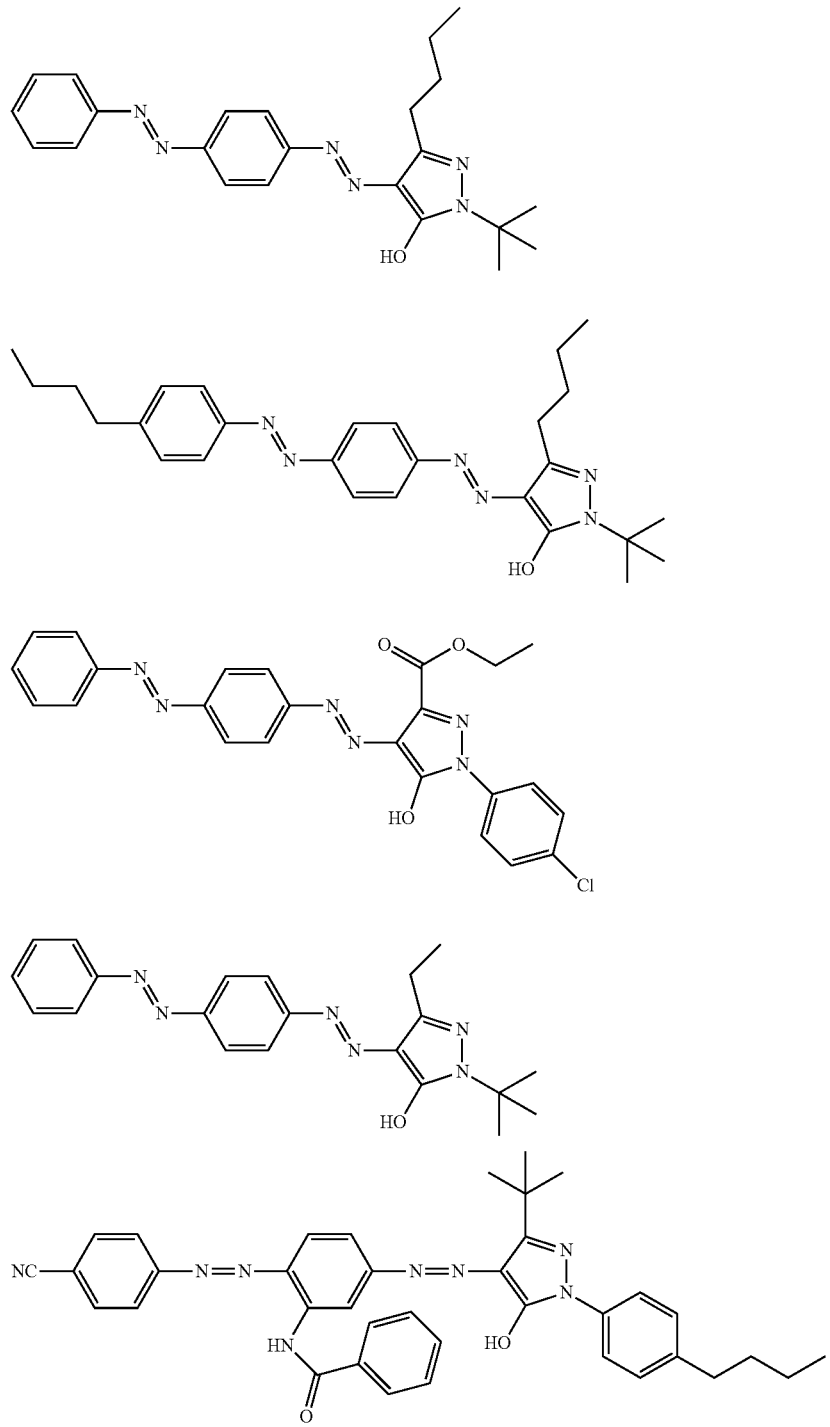

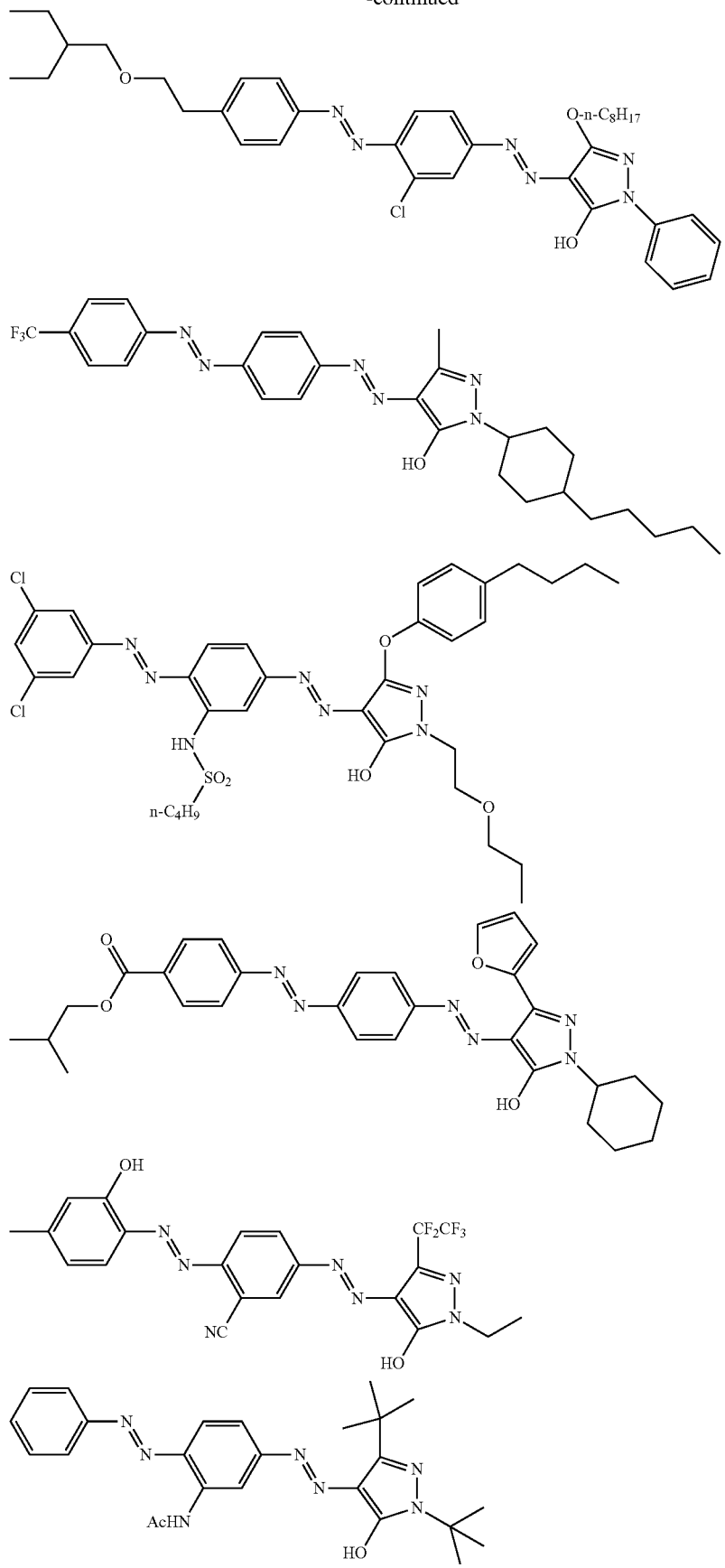

-continued
[Chem. 22]
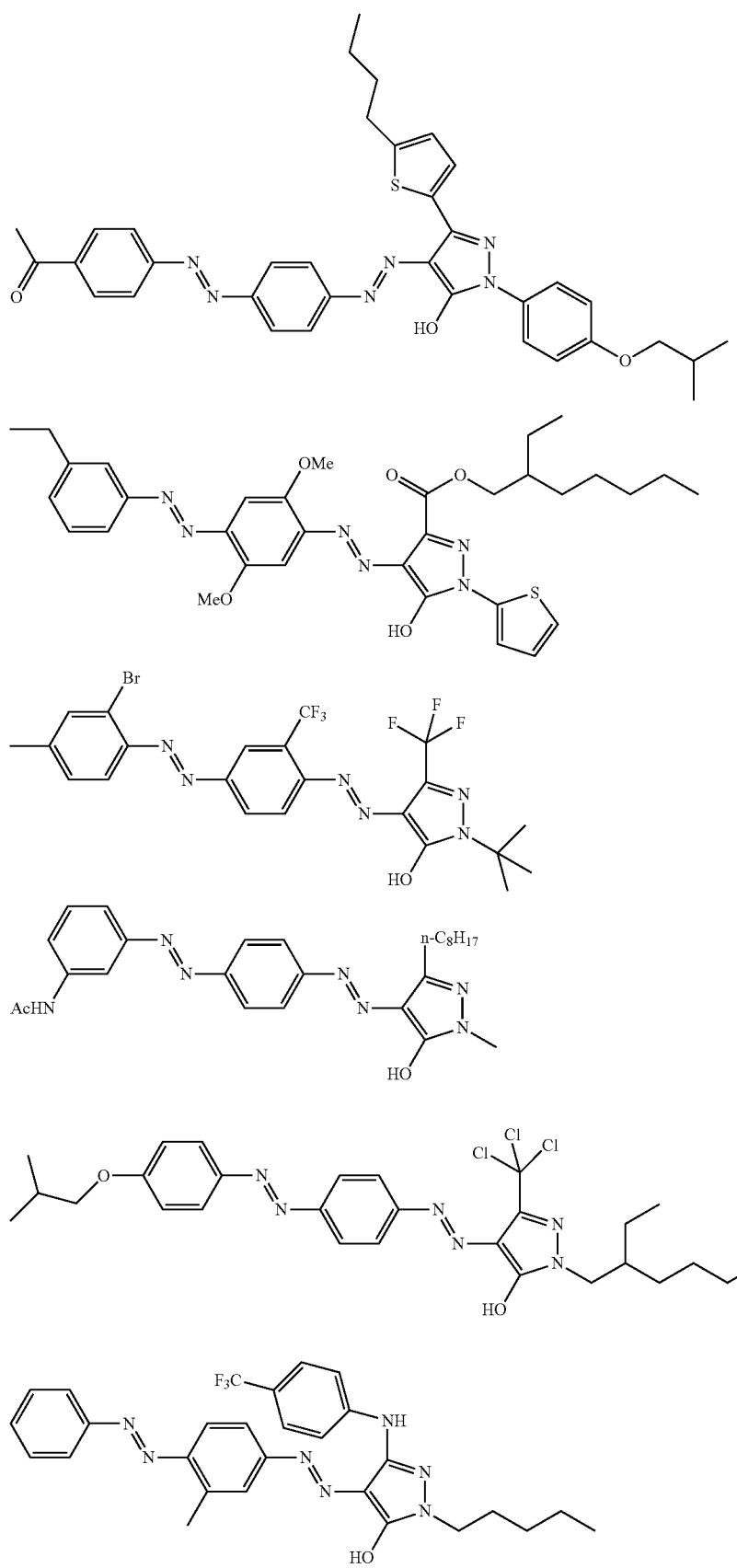

-continued

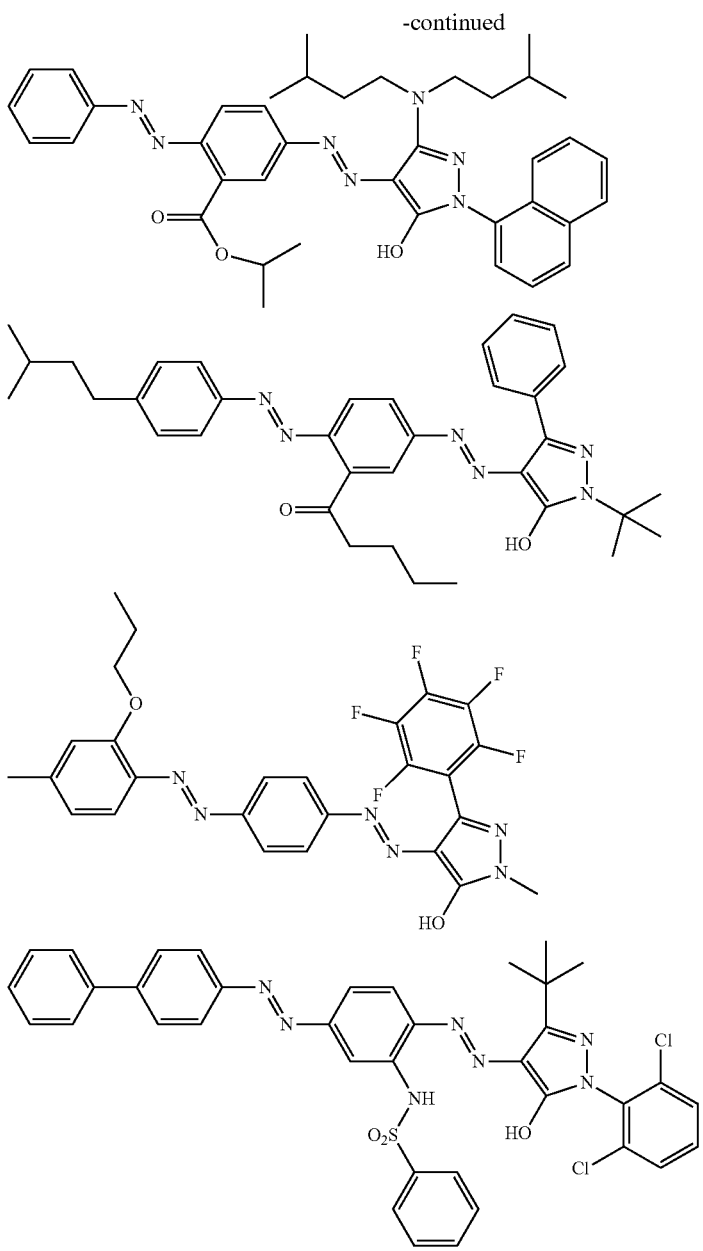

The compound represented by general formula (4) can be synthesized, for example, in accordance with the method described in International Publication WO 2009/063880.

Examples of the heterocyclic compounds include compounds represented by the following general formula (5).

[Chem. 23]

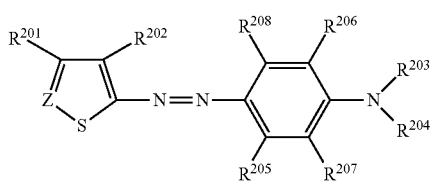

[In general formula (5),
$R^{201}$, $R^{202}$, $R^{203}$, $R^{204}$, $R^{205}$, $R^{206}$, $R^{207}$, and $R^{208}$ each independently represent a hydrogen atom or any substituent, and
Z represents a nitrogen atom or a methine group which may have a substituent.]

<$R^{201}$>

$R^{201}$ represents a hydrogen atom or any substituent. Although $R^{201}$ is not particularly limited unless the effects of the invention are lessened thereby, it is preferable from the standpoint of high extinction coefficient that $R^{201}$ should be a hydrogen atom or an alkyl group which has 1-20 carbon atoms and may have a substituent.

(Alkyl Group which May have a Substituent)

The term "alkyl group which has 1-20 carbon atoms and may have a substituent" for $R^{201}$ has the same meaning as the alkyl group which may have a substituent, examples of which were shown above with regard to the $R^1$ contained in general formula (1), and the substituents which may be possessed are also the same. $R^{201}$ may be bonded to Z to form a cyclic structure.

It is preferable that $R^{201}$ should be a substituent having a low molecular weight, from the standpoint of gram extinction coefficient. Specifically, the number of carbon atoms thereof is preferably 16 or less, more preferably 10 or less, especially preferably 6 or less. In cases when the number of carbon atoms thereof is in an adequate range, there are cases where the compound can have excellent solubility in solvents and a high gram extinction coefficient.

From the standpoint of production, it is preferable that $R^{201}$ should be an unsubstituted alkyl group, and it is especially preferable that $R^{201}$ should be an unsubstituted alkyl group having 1-4 carbon atoms, such as methyl, ethyl, propyl, isopropyl, or butyl.

<$R^{202}$>

$R^{202}$ represents a hydrogen atom or any substituent. Although $R^{202}$ is not particularly limited unless the effects of the invention are lessened thereby, it is preferable that $R^{202}$ should be a cyano group or a —$COOR^{209}$ group, from the standpoints of high solubility in solvents and high extinction coefficient.

$R^{209}$ represents an alkyl group which has 1-20 carbon atoms and may have a substituent, an aryl group which has 6-20 carbon atoms and may have a substituent, or a heteroaryl group which has 2-20 carbon atoms and may have a substituent.

The term "alkyl group which may have a substituent" for $R^{209}$ specifically has the same meaning as the alkyl group which may have a substituent, examples of which were shown above with regard to the $R^1$ contained in general formula (1), and the substituents which may be possessed are also the same. The number of carbon atoms of the alkyl group represented by $R^{209}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

The term "aryl group which may have a substituent" for $R^{209}$ specifically has the same meaning as the aryl group which may have a substituent, examples of which were shown above with regard to the $R^{101}$ contained in general formula (4), and the substituents which may be possessed are also the same as those of the aryl group which were shown above as examples with regard to the $R^{101}$ contained in general formula (4).

The term "heteroaryl group which may have a substituent" for $R^{209}$ specifically has the same meaning as the heteroaryl group which may have a substituent, examples of which were shown above with regard to the $R^{101}$ contained in general formula (4), and the substituents which may be possessed are also the same as those of the heteroaryl group which were shown above as examples with regard to the $R^{101}$ contained in general formula (4).

<$R^{203}$ and $R^{204}$>

$R^{203}$ and $R^{204}$ each independently represent a hydrogen atom or any substituent. Although $R^{203}$ and $R^{204}$ are not particularly limited unless the effects of the invention are lessened thereby, it is preferable that $R^{203}$ and $R^{204}$ should each independently be an alkyl group which has 1-20 carbon atoms and may have a substituent, from the standpoints of high solubility in solvents and high extinction coefficient.

$R^{203}$ and $R^{204}$ may be bonded to each other to form a cyclic structure. Furthermore, $R^{203}$ or $R^{204}$ may be bonded respectively to $R^{206}$ or $R^{207}$ to form a cyclic structure.

The term "alkyl group which may have a substituent" for $R^{203}$ and $R^{204}$ specifically has the same meaning as the alkyl group which may have a substituent, examples of which were shown above with regard to the $R^1$ contained in general formula (1), and the substituents which may be possessed are also the same.

The number of carbon atoms of each of the alkyl groups represented by $R^{203}$ and $R^{204}$ is preferably 2 or larger, more preferably 4 or larger. Meanwhile, the number of carbon atoms thereof is preferably 16 or less, more preferably 10 or less, especially preferably 6 or less. In cases when the number of carbon atoms thereof is in an adequate range, there are cases where the compound can have excellent solubility in solvents and a high gram extinction coefficient.

<$R^{205}$, $R^{206}$, $R^{207}$, and $R^{208}$>

$R^{205}$, $R^{206}$, $R^{207}$, and $R^{208}$ each independently represent a hydrogen atom or any substituent. $R^{205}$, $R^{206}$, $R^{207}$, and $R^{208}$ are not particularly limited unless the effects of the invention are lessened thereby. However, from the standpoints of high solubility in solvents and high extinction coefficient, it is preferable that $R^{205}$, $R^{206}$, $R^{207}$, and $R^{208}$ each should be a hydrogen atom, a halogen atom, an alkyl group which has 1-20 carbon atoms and may have a substituent, an alkoxy group which has 1-20 carbon atoms and may have a substituent, an —$NHCOR^{210}$ group, or an —$NHSO_2R^{212}$ group.

$R^{210}$ and $R^{212}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

It is preferable that $R^{205}$, $R^{206}$, $R^{207}$, and $R^{208}$ should each independently be an alkyl group having 1-4 carbon atoms, such as methyl, ethyl, propyl, isopropyl, cyclopropyl, butyl, isobutyl, sec-butyl, or tert-butyl, an —$NHCOR^{210}$ group, or an —$NHSO_2R^{212}$ group, among those atoms and groups. Methyl, an —$NHCOR^{210}$ group, or an —$NHSO_2R^{212}$ group is especially preferred from the standpoints of high solubility in solvents and high extinction coefficient.

(Alkyl Group which May have a Substituent)

The term "alkyl group which may have a substituent" for $R^{205}$, $R^{206}$, $R^{207}$, $R^{208}$, $R^{210}$, $R^{212}$ specifically has the same meaning as the alkyl group which may have a substituent, examples of which were shown above with regard to the $R^1$ contained in general formula (1), and the substituents which may be possessed are also the same.

The number of carbon atoms of each of the alkyl groups represented by $R^{205}$, $R^{206}$, $R^{207}$, $R^{208}$, $R^{210}$, $R^{212}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group which may have a substituent" for $R^{205}$, $R^{206}$, $R^{207}$, and $R^{208}$ has the same meaning as the alkoxy group which may have a substituent, examples of which were shown above with regard to the $R^1$ contained in general formula (1), and the substituents which may be possessed are also the same.

The number of carbon atoms of each of the alkoxy groups represented by $R^{205}$, $R^{206}$, $R^{207}$, and $R^{208}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group which may have a substituent" for $R^{210}$ and $R^{212}$ specifically has the same meaning as the aryl group which may have a substituent, examples of which were shown above with regard to the $R^{101}$ contained in general formula (4), and the substituents which may be possessed are also the same.

(Heteroaryl Group which May have a Substituent)

The term "heteroaryl group which may have a substituent" for $R^{210}$ and $R^{212}$ specifically has the same meaning as the heteroaryl group which may have a substituent, examples of which were shown above with regard to the $R^{101}$ contained in general formula (4), and the substituents which may be possessed are also the same.

<Z>

Z represents a nitrogen atom or a methine group which may have a substituent. In the case where Z is a methine group, this Z may be unsubstituted or may have a substituent. Examples of the substituent which may be possessed by Z include alkyl groups which have 1-10 carbon atoms and may have a substituent, and further include a $-COOR^{211}$ group.

$R^{211}$ represents an alkyl group which has 1-20 carbon atoms and may have a substituent. Specifically, this term has the same meaning as the alkyl group which may have a substituent, examples of which were shown above with regard to the $R^1$ contained in general formula (1), and the substituents which may be possessed are also the same. The number of carbon atoms of the alkyl group represented by $R^{211}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

It is preferable that Z should be a nitrogen atom, a methine group, a methine group substituted with an alkyl group having 1-4 carbon atoms, or a methine group substituted with an alkoxycarbonyl group having 2-5 carbon atoms.

Especially preferred compounds among the compounds represented by general formula (5) include the compounds shown in the following Tables 1 to 3.

TABLE 1

| No. | Z | $R^{201}$ | $R^{202}$ | $R^{203}$ |
|---|---|---|---|---|
| 1 | N | $CH_2CH_3$ | CN | $i-C_4H_9$ |
| 2 | N | $CH_3$ | CN | $CH_2CH(CH_2CH_3)CH_2CH_2CH_2CH_3$ |
| 3 | $C-CO_2CH_2CH_3$ | $CH_3$ | $CO_2CH_2CH_3$ | $CH_2CH(CH_2CH_3)CH_2CH_2CH_2CH_3$ |
| 4 | N | $CH_2CH_3$ | CN | $CH_2CH(CH_2CH_3)CH_2CH_2CH_2CH_3$ |
| 5 | N | $CH_3$ | CN | $CH_2CH(CH_2CH_3)CH_2CH_2CH_2CH_3$ |
| 6 | $C-CO_2CH_2CH_3$ | $CH_3$ | $CO_2CH_2CH_3$ | $CH_2CH(CH_2CH_3)CH_2CH_2CH_2CH_3$ |
| 7 | $C-CO_2CH_2CH_3$ | $CH_3$ | $CO_2CH_2CH_3$ | $CH_2CH(CH_2CH_3)CH_2CH_2CH_2CH_3$ |
| 8 | N | $CH_3$ | CN | $CH_2CH(CH_2CH_3)CH_2CH_2CH_2CH_3$ |
| 9 | N | $CH_3$ | CN | $CH_2CH(CH_2CH_3)CH_2CH_2CH_2CH_3$ |
| 10 | N | $CH_2CH_3$ | CN | $CH_2CH(CH_2CH_3)CH_2CH_2CH_2CH_3$ |
| 11 | N | $CH_2CH_3$ | CN | $CH_2CH(CH_2CH_3)CH_2CH_2CH_2CH_3$ |
| 12 | N | $n-C_4H_9$ | CN | $i-C_4H_9$ |
| 13 | N | $n-C_4H_9$ | CN | $CH_2CH(CH_2CH_3)CH_2CH_2CH_2CH_3$ |
| 14 | N | $i-C_3H_7$ | CN | $CH_2CH(CH_2CH_3)CH_2CH_2CH_2CH_3$ |
| 15 | N | $CH_3$ | CN | $CH_2CH(CH_2CH_3)CH_2CH_2CH_2CH_3$ |
| 16 | N | $CH_3$ | CN | $CH_2CH(CH_2CH_3)CH_2CH_2CH_2CH_3$ |
| 17 | N | $CH_3$ | CN | $CH_2CH(CH_2CH_3)CH_2CH_2CH_2CH_3$ |
| 18 | $C-CO_2CH_2CH_3$ | $CH_3$ | $CO_2CH_2CH_3$ | $i-C_4H_9$ |
| 19 | $C-CO_2CH_2CH_3$ | $CH_3$ | CN | $CH_2CH(CH_2CH_3)CH_2CH_2CH_2CH_3$ |
| 20 | $C-CO_2CH_2CH_3$ | $CH_3$ | CN | $CH_2CH(CH_2CH_3)CH_2CH_2CH_2CH_3$ |

| No. | $R^{204}$ | $R^{205}$ | $R^{206}$ | $R^{207}$ | $R^{208}$ |
|---|---|---|---|---|---|
| 1 | $i-C_4H_9$ | $NHCOCH_3$ | H | H | H |
| 2 | $CH_2CH(CH_2CH_3)CH_2CH_2CH_2CH_3$ | $NHCOCH_3$ | H | H | H |
| 3 | $CH_2CH(CH_2CH_3)CH_2CH_2CH_2CH_3$ | $NHCOCH_3$ | H | H | H |
| 4 | $CH_2CH(CH_2CH_3)CH_2CH_2CH_2CH_3$ | $CH_3$ | H | H | H |
| 5 | $n-C_8H_{17}$ | $CH_3$ | H | H | H |
| 6 | $CH_2CH(CH_2CH_3)CH_2CH_2CH_2CH_3$ | $CH_3$ | H | H | H |
| 7 | $CH_2CH(CH_2CH_3)CH_2CH_2CH_2CH_3$ | $NHCOCH_2CH_3$ | H | H | H |
| 8 | $CH_2CH(CH_2CH_3)CH_2CH_2CH_2CH_3$ | $CH_2CH_3$ | H | H | H |
| 9 | $CH_2CH(CH_2CH_3)CH_2CH_2CH_2CH_3$ | $NHCOCH_2CH_3$ | H | H | H |
| 10 | $CH_2CH(CH_2CH_3)CH_2CH_2CH_2CH_3$ | $NHCOCH_3$ | H | H | H |
| 11 | $CH_2CH_3$ | $NHCOCH_3$ | H | H | H |
| 12 | $i-C_4H_9$ | $NHCOCH_3$ | H | H | H |
| 13 | $CH_2CH(CH_2CH_3)CH_2CH_2CH_2CH_3$ | $CH_3$ | H | H | H |
| 14 | $CH_2CH(CH_2CH_3)CH_2CH_2CH_2CH_3$ | $CH_3$ | H | H | H |
| 15 | $CH_2CH(CH_2CH_3)CH_2CH_2CH_2CH_3$ | $i-C_3H_7$ | H | H | H |
| 16 | $CH_2CH(CH_2CH_3)CH_2CH_2CH_2CH_3$ | $CH_3$ | $OCH_3$ | H | H |
| 17 | $CH_2CH(CH_2CH_3)CH_2CH_2CH_2CH_3$ | H | H | H | H |
| 18 | $i-C_4H_9$ | $CH_3$ | H | H | H |
| 19 | $CH_2CH(CH_2CH_3)CH_2CH_2CH_2CH_3$ | $CH_3$ | $OCH_3$ | H | H |
| 20 | $CH_2CH(CH_2CH_3)CH_2CH_2CH_2CH_3$ | $CH_2CH_3$ | H | H | H |

TABLE 2

| No. | Z | $R^{201}$ | $R^{202}$ | $R^{203}$ |
|---|---|---|---|---|
| 21 | N | i-$C_3H_7$ | CN | i-$C_4H_9$ |
| 22 | N | $CH_3$ | $CO_2CH_3$ | $CH_2CH(CH_2CH_3)CH_2CH_2CH_2CH_3$ |
| 23 | N | $CH_3$ | $CO_2$—n-$C_3H_7$ | i-$C_4H_9$ |
| 24 | N | $CH_3$ | CN | $(CF_2)_5CF_3$ |
| 25 | N | $CH_3$ | CN | $CH_2CH(CH_2CH_3)CH_2CH_2CH_2CH_3$ |
| 26 | N | $CH_3$ | CN | i-$C_4H_9$ |
| 27 | N | $CH_3$ | CN | $CH_2CH(CH_2CH_3)CH_2CH_2CH_2CH_3$ |
| 28 | C—$CO_2CH_3$ | $CH_3$ | $CO_2CH_3$ | $CH_2CH(CH_2CH_3)CH_2CH_2CH_2CH_3$ |
| 29 | C—$CO_2$—n-$C_4H_9$ | $CH_3$ | $CO_2$—n-$C_4H_9$ | i-$C_4H_9$ |
| 30 | C—$CH_3$ | $CH_3$ | $CO_2CH_3$ | $CH_2CH(CH_2CH_3)CH_2CH_2CH_2CH_3$ |
| 31 | C—n-$C_4H_9$ | $CH_3$ | $CO_2CH_3$ | i-$C_4H_9$ |
| 32 | C—$CO_2$—$CH_2CH_3$ | $CH_3$ | CN | $CH_2CH(CH_2CH_3)CH_2CH_2CH_2CH_3$ |
| 33 | C—$CO_2$—$CH_2CH_3$ | $CH_3$ | $CO_2$—$CH_2CH_3$ | $CH_2CH(CH_2CH_3)CH_2CH_2CH_2CH_3$ |
| 34 | C—$CO_2$—$CH_2CH_3$ | $CH_3$ | $CO_2$—$CH_2CH_3$ | $CH_2CH(CH_2CH_3)CH_2CH_2CH_2CH_3$ |
| 35 | C—$CO_2$—$CH_2CH_3$ | $CH_3$ | CN | $CH_2CH(CH_2CH_3)CH_2CH_2CH_2CH_3$ |
| 36 | C—CN | $CH_3$ | CN | $CH_2CH(CH_2CH_3)CH_2CH_2CH_2CH_3$ |
| 37 | C—CN | $CH_3$ | CN | $CH_2CH(CH_2CH_3)CH_2CH_2CH_2CH_3$ |
| 38 | N | $CH_3$ | CN | $CH_2CH(CH_2CH_3)CH_2CH_2CH_2CH_3$ |
| 39 | N | $CH_3$ | CN | $CH_2CH(CH_2CH_3)CH_2CH_2CH_2CH_3$ |
| 40 | C—$CO_2CH_3$ | $CH_3$ | $CO_2CH_3$ | $CH_2CH(CH_2CH_3)CH_2CH_2CH_2CH_3$ |

| No. | $R^{204}$ | $R^{205}$ | $R^{206}$ | $R^{207}$ | $R^{208}$ |
|---|---|---|---|---|---|
| 21 | i-$C_4H_9$ | H | H | H | H |
| 22 | $CH_2CH(CH_2CH_3)CH_2CH_2CH_2CH_3$ | $NHCOCH_3$ | H | H | H |
| 23 | i-$C_4H_9$ | $NHCOCH_3$ | H | H | H |
| 24 | $(CF_2)_5CF_3$ | $NHCOCH_3$ | H | H | H |
| 25 | $CH_2CH(CH_2CH_3)CH_2CH_2CH_2CH_3$ | NHCOPh | H | H | H |
| 26 | i-$C_4H_9$ | NHCO—i-$C_4H_9$ | H | H | H |
| 27 | $CH_2CH(CH_2CH_3)CH_2CH_2CH_2CH_3$ | $NHCOCH_3$ | $OCH_3$ | H | H |
| 28 | $CH_2CH(CH_2CH_3)CH_2CH_2CH_2CH_3$ | Cl | H | $CH_3$ | H |
| 29 | i-$C_4H_9$ | $NHCOCH_3$ | $CH_3$ | H | H |
| 30 | $CH_2CH(CH_2CH_3)CH_2CH_2CH_2CH_3$ | $CH_3$ | H | $OCH_3$ | H |
| 31 | i-$C_4H_9$ | NHCO—i-$C_4H_9$ | H | H | H |
| 32 | $CH_2CH(CH_2CH_3)CH_2CH_2CH_2CH_3$ | $NHCOCH_3$ | H | H | H |
| 33 | $CH_2CH(CH_2CH_3)CH_2CH_2CH_2CH_3$ | $NHCOCH_3$ | $OCH_3$ | H | H |
| 34 | $CH_2CH(CH_2CH_3)CH_2CH_2CH_2CH_3$ | $CH_3$ | $OCH_3$ | H | H |
| 35 | $CH_2CH(CH_2CH_3)CH_2CH_2CH_2CH_3$ | $CH_3$ | H | H | H |
| 36 | $CH_2CH(CH_2CH_3)CH_2CH_2CH_2CH_3$ | $NHCOCH_3$ | H | H | H |
| 37 | $CH_2CH(CH_2CH_3)CH_2CH_2CH_2CH_3$ | $CH_3$ | H | H | H |
| 38 | $CH_2CH(CH_2CH_3)CH_2CH_2CH_2CH_3$ | $NHCOCH_3$ | Cl | H | H |
| 39 | $CH_2CH(CH_2CH_3)CH_2CH_2CH_2CH_3$ | F | H | H | H |
| 40 | $CH_2CH(CH_2CH_3)CH_2CH_2CH_2CH_3$ | Cl | $CH_3$ | H | H |

TABLE 3

| No. | Z | $R^{201}$ | $R^{202}$ | $R^{203}$ |
|---|---|---|---|---|
| 41 | N | n-$C_6H_{13}$ | $CO_2$—n-$C_4H_9$ | n-$C_6H_{13}$ |
| 42 | N | $CH_2OCH_2CH_3$ | $CO_2CF_3$ | $CH_2OCH_2CH_3$ |
| 43 | N | $CF_3$ | $CO_2$—Ph | $CF_3$ |
| 44 | N | $CF_2CF_3$ | $CO_2CH_2$—Ph | $CF_2CF_3$ |
| 45 | N | Ph | $CO_2CH_2$-cyclohexanel | Ph |
| 46 | N | $CH_2$—Ph | $CO_2CH_2CH_2OCH_3$ | $CH_2$—Ph |
| 47 | N | $CH_2CH_2O$—Ph | $CO_2$—n-$C_8H_{17}$ | $CH_2CH_2O$—Ph |
| 48 | N | $CH_2$-cyclohexyl | $CO_2CH_2CH_2CH_2CF_3$ | $CH_2$-cyclohexyl |
| 49 | N | n-$C_8H_{17}$ | $CO_2CH_2CH_2CH_2CN$ | n-$C_8H_{17}$ |
| 50 | N | $CH_3$ | CN | $CH_2CH(CH_2CH_3)CH_2CH_2CH_2CH_3$ |
| 51 | C—$CO_2$Ph | n-$C_6H_{13}$ | $CO_2$—n-$C_4H_9$ | n-$C_6H_{13}$ |
| 52 | C—$CO_2CH_2$Ph | $CH_2OCH_2CH_3$ | $CO_2CF_3$ | $CH_2OCH_2CH_3$ |
| 53 | C—$CO_2$—n-$C_8H_{17}$ | $CF_3$ | $CO_2$—Ph | $CF_3$ |
| 54 | C—$CO_2$—n-$C_6H_{13}$ | $CF_2CF_3$ | $CO_2CH_2$—Ph | $CF_2CF_3$ |
| 55 | C—$CO_2$-cyclohexyl | Ph | $CO_2CH_2$-cyclohexanel | Ph |
| 56 | C—CN | $CH_2$—Ph | $CO_2CH_2CH_2OCH_3$ | $CH_2$—Ph |
| 57 | C—CN | $CH_2CH_2O$—Ph | $CO_2$—n-$C_8H_{17}$ | $CH_2CH_2O$—Ph |
| 58 | C—CN | $CH_2$-cyclohexyl | $CO_2CH_2CH_2CH_2CF_3$ | $CH_2$-cyclohexyl |
| 59 | C—CN | n-$C_8H_{17}$ | $CO_2CH_2CH_2CH_2CN$ | n-$C_8H_{17}$ |
| 60 | C—CN | $CH_2CH_2CH_2CF_3$ | $CO_2CH(CH_3)CH_2CH_3$ | $CH_2CH_2CH_2CF_3$ |

| No. | $R^{204}$ | $R^{205}$ | $R^{206}$ | $R^{207}$ | $R^{208}$ |
|---|---|---|---|---|---|
| 41 | n-$C_6H_{13}$ | O—n-Bu | H | H | H |
| 42 | $CH_2OCH_2CH_3$ | $CF_3$ | H | H | H |
| 43 | $CF_3$ | $NHSO_2CF_3$ | H | H | H |
| 44 | $CF_2CF_3$ | $NHSO_2$—n-Bu | H | H | H |

TABLE 3-continued

| | | | | | |
|---|---|---|---|---|---|
| 45 | Ph | Br | H | H | H |
| 46 | CH$_2$—Ph | H | O—n-C$_6$H$_{13}$ | H | H |
| 47 | CH$_2$CH$_2$O—Ph | H | CF$_2$CF$_2$CF$_2$CF$_3$ | H | H |
| 48 | CH$_2$-cyclohexyl | H | NHSO$_2$CH$_2$—Ph | H | H |
| 49 | n-C$_8$H$_{17}$ | H | NHSO$_2$—Ph | H | H |
| 50 | CH$_2$CH(CH$_2$CH$_3$)CH$_2$CH$_2$CH$_3$ | NHSO$_2$—n-Bu | H | H | H |
| 51 | n-C$_6$H$_{13}$ | O—n-Bu | H | H | H |
| 52 | CH$_2$OCH$_2$CH$_3$ | CF$_3$ | H | H | H |
| 53 | CF$_3$ | NHSO$_2$CF$_3$ | H | H | H |
| 54 | CF$_2$CF$_3$ | NHSO$_2$—n-Bu | H | H | H |
| 55 | Ph | Br | H | H | H |
| 56 | CH$_2$—Ph | H | O—n-C$_6$H$_{13}$ | H | H |
| 57 | CH$_2$CH$_2$O—Ph | H | CF$_2$CF$_2$CF$_2$CF$_3$ | H | H |
| 58 | CH$_2$-cyclohexyl | H | NHSO$_2$CH$_2$—Ph | H | H |
| 59 | n-C$_8$H$_{17}$ | H | NHSO$_2$—Ph | H | H |
| 60 | CH$_2$CH$_2$CH$_2$CF$_3$ | Me | CH$_3$ | Me | H |

The compound represented by general formula (5) can be synthesized, for example, in accordance with the method describe in JP-T-8-505820.

Examples of the heterocyclic compounds include compounds represented by the following general formula (6).

[Chem. 24]

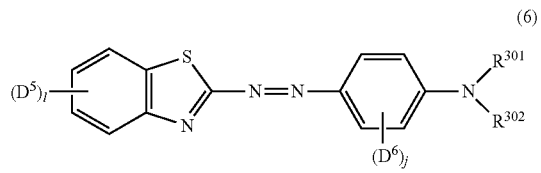

(6)

[In general formula (6),
$R^{301}$, $R^{302}$, $D^5$, and $D^6$ each independently represent any substituent,
l represents an integer of 0-4, and when l is 2 or larger, the two or more $D^5$s present in the molecule may be the same or different, and
j represents an integer of 0-4, and when j is 2 or larger, the two or more $D^6$s present in the molecule may be the same or different.]

<$R^{301}$ and $R^{302}$>

$R^{301}$ and $R^{302}$ each independently represent any substituent. $R^{301}$ and $R^{302}$ are not particularly limited unless the effects of the invention are lessened thereby. However, from the standpoints of high extinction coefficient and high solubility in solvents, it is preferable that $R^{301}$ and $R^{302}$ should each independently be an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for $R^{301}$ and $R^{302}$ specifically has the same meaning as the alkyl group which may have a substituent, examples of which were shown above with regard to the $R^1$ contained in general formula (1), and the substituents which may be possessed are also the same.

The number of carbon atoms of each of the alkyl groups which may have a substituent and are represented by $R^{301}$ and $R^{302}$ is preferably 2 or larger, more preferably 4 or larger. Meanwhile, the number of carbon atoms thereof is preferably 16 or less, more preferably 12 or less. In cases when the number of carbon atoms thereof is in an adequate range, there are cases where the compound can have excellent solubility in solvents and a high gram extinction coefficient.

(Aryl Group which May have a Substituent)

The term "aryl group" for $R^{301}$ and $R^{302}$ specifically has the same meaning as the aryl group, examples of which were shown above with regard to the $R^{101}$ contained in general formula (4), and the substituents which may be possessed are also the same as those of the aryl group which were shown above as examples with regard to the $R^{101}$ contained in general formula (4).

(Heteroaryl Group which May have a Substituent)

The term "heteroaryl group" for $R^{301}$ and $R^{302}$ specifically has the same meaning as the heteroaryl group, examples of which were shown above with regard to the $R^{101}$ contained in general formula (4), and the substituents which may be possessed are also the same as those of the heteroaryl group which were shown above as examples with regard to the $R^{101}$ contained in general formula (4).

<$D^5$>

$D^5$ represents any substituent. $D^5$ is not particularly limited unless the effects of the invention are lessened thereby. However, from the standpoints of high extinction coefficient and high solubility in solvents, it is preferable that $D^5$ should be a halogen atom, a cyano group, an alkyl group which has 1-20 carbon atoms and may have a substituent, an alkoxy group which has 1-20 carbon atoms and may have a substituent, an —SCN group, a —COOR$^{303}$ group, a —COR$^{306}$ group, or an —OCOR$^{307}$ group.

Symbol l represents an integer of 0-4. When l is 2 or larger, the two or more $D^5$s present in the molecule may be the same or different.

$R^{303}$, $R^{306}$, and $R^{307}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group" for $D^5$, $R^{303}$, $R^{306}$, and $R^{307}$ specifically has the same meaning as the alkyl group, examples of which were shown above with regard to the $R^1$ contained in general formula (1), and the substituents which may be possessed are also the same. The number of carbon atoms of each of the alkyl groups represented by $D^5$, $R^{303}$, $R^{306}$, and $R^{307}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group" for $D^5$ has the same meaning as the alkoxy group, examples of which were shown above with regard to the $R^1$ contained in general formula (1), and the substituents which may be possessed are also the same. The number of carbon atoms of the alkoxy group represented by $D^5$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group" for $R^{303}$, $R^{306}$, and $R^{307}$ specifically has the same meaning as the aryl group, examples of which were shown above with regard to the $R^{101}$ contained in general formula (4), and the substituents which may be possessed are also the same as those of the aryl group which were shown above as examples with regard to the $R^{101}$ contained in general formula (4).

(Heteroaryl Group which May have a Substituent)

The term "heteroaryl group" for $R^{303}$, $R^{306}$, and $R^{307}$ specifically has the same meaning as the heteroaryl group, examples of which were shown above with regard to the $R^{101}$ contained in general formula (4), and the substituents which may be possessed are also the same as those of the heteroaryl group which were shown above as examples with regard to the $R^{101}$ contained in general formula (4).

<$D^6$>

$D^6$ represents any substituent. $D^6$ is not particularly limited unless the effects of the invention are lessened thereby. However, from the standpoints of high extinction coefficient and high solubility in solvents, it is preferable that $D^6$ should be an alkyl group which has 1-20 carbon atoms and may have a substituent, an alkoxy group which has 1-20 carbon atoms and may have a substituent, an —NHCOR$^{304}$ group, or an —NHSO$_2$R$^{305}$ group.

Symbol j represents an integer of 0-4. When j is 2 or larger, the two or more $D^6$s present in the molecule may be the same or different.

$R^{304}$ and $R^{305}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group" for $D^6$, $R^{304}$, and $R^{305}$ specifically has the same meaning as the alkyl group, examples of which were shown above with regard to the $R^1$ contained in general formula (1), and the substituents which may be possessed are also the same. The number of carbon atoms of each of the alkyl groups represented by $D^6$, $R^{304}$, and $R^{305}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group" for $D^6$ has the same meaning as the alkoxy group, examples of which were shown above with regard to the $R^1$ contained in general formula (1), and the substituents which may be possessed are also the same. The number of carbon atoms of the alkoxy group represented by $D^6$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group" for $R^{304}$ and $R^{305}$ specifically has the same meaning as the aryl group, examples of which were shown above with regard to the $R^1$ contained in general formula (4), and the substituents which may be possessed are also the same as those of the aryl group which were shown above as examples with regard to the $R^{101}$ contained in general formula (4).

(Heteroaryl Group which May have a Substituent)

The term "heteroaryl group" for $R^{304}$ and $R^{305}$ specifically has the same meaning as the heteroaryl group, examples of which were shown above with regard to the $R^{101}$ contained in general formula (4), and the substituents which may be possessed are also the same as those of the heteroaryl group which were shown above as examples with regard to the $R^{101}$ contained in general formula (4).

Specific examples of the compounds represented by general formula (6) are shown below. However, the heterocyclic compounds should not be construed as being limited t the following examples unless the compounds depart from the spirit thereof.

[Chem. 25]

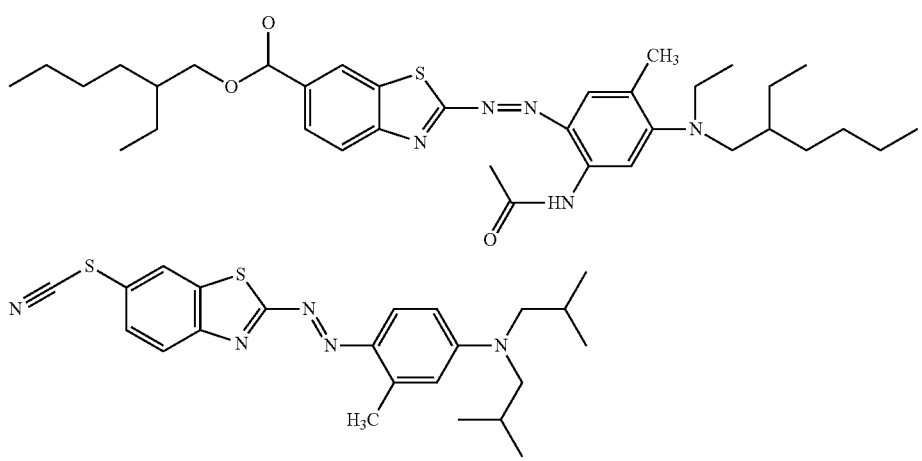

-continued
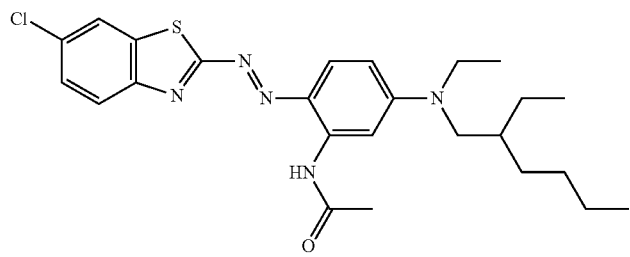
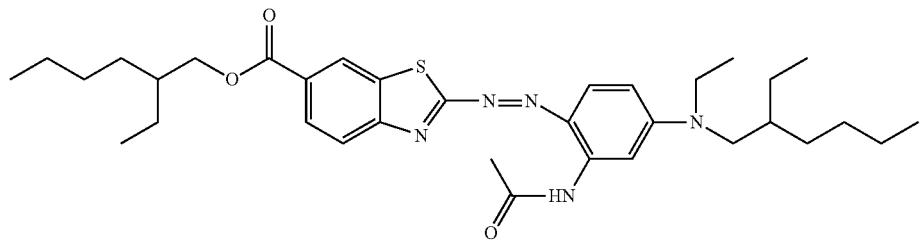
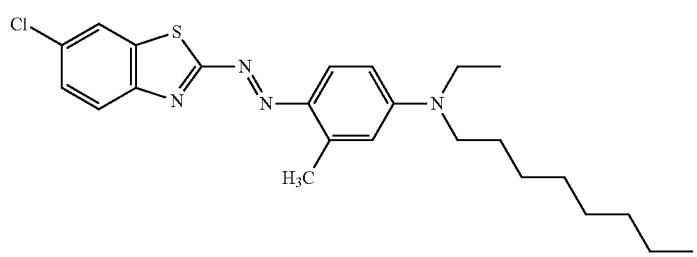
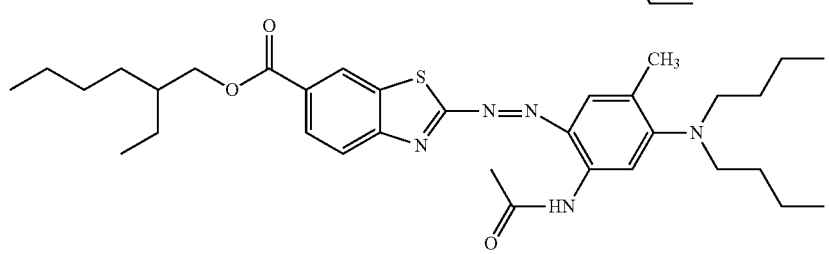
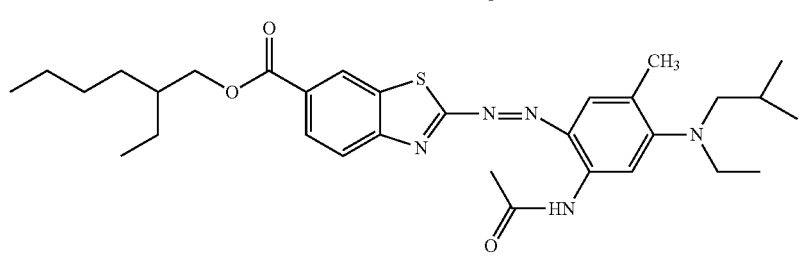
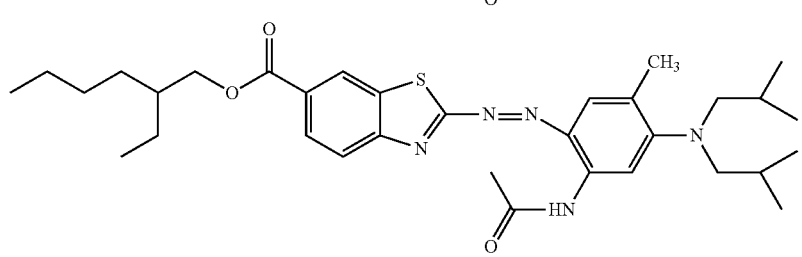
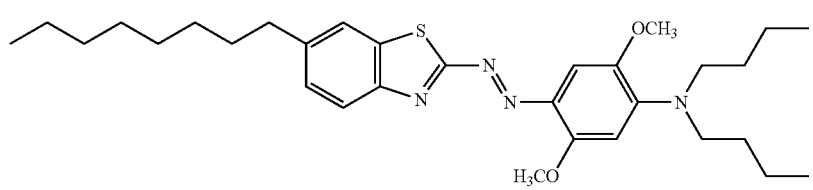

-continued
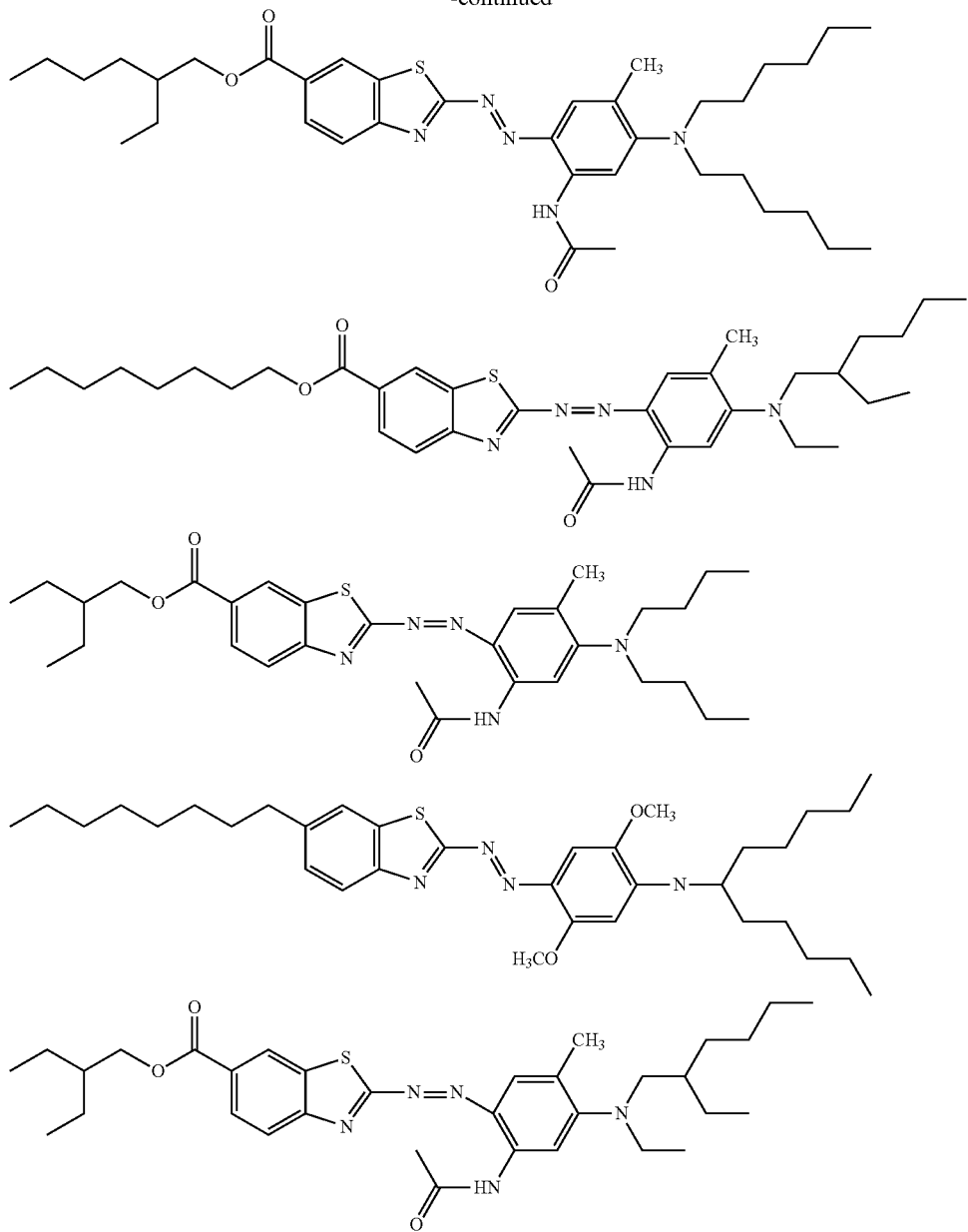
[Chem. 26]
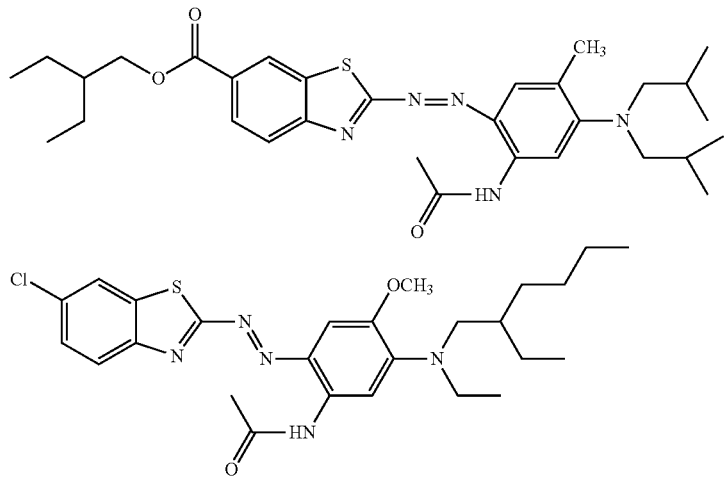

-continued
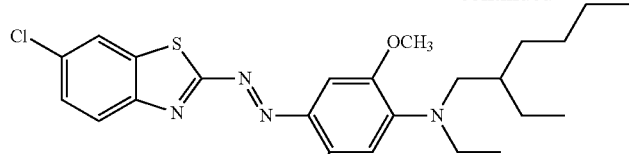
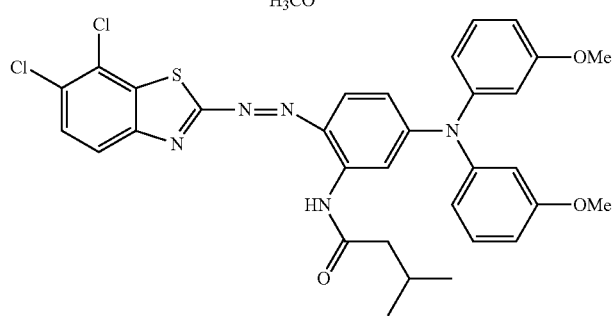
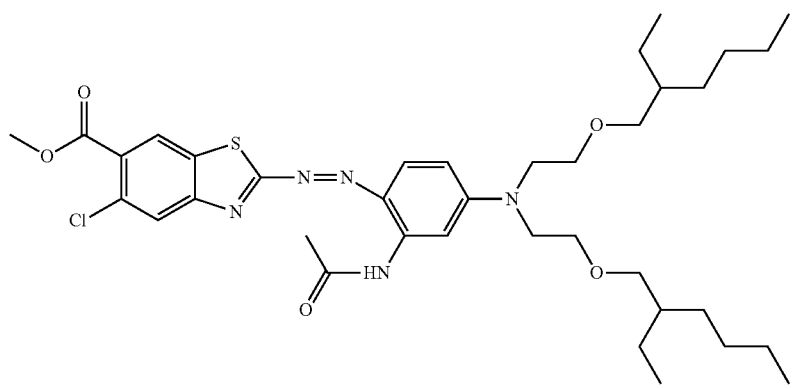
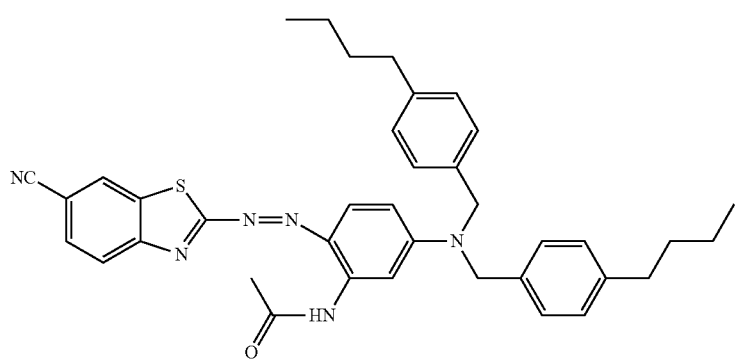
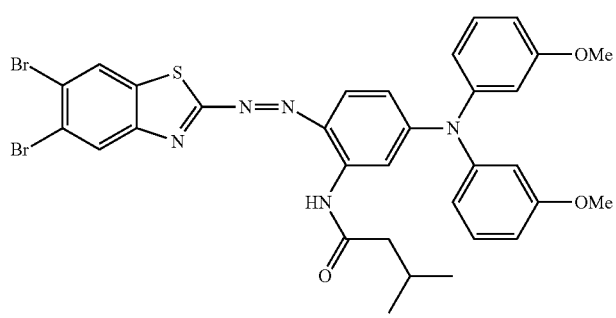

-continued
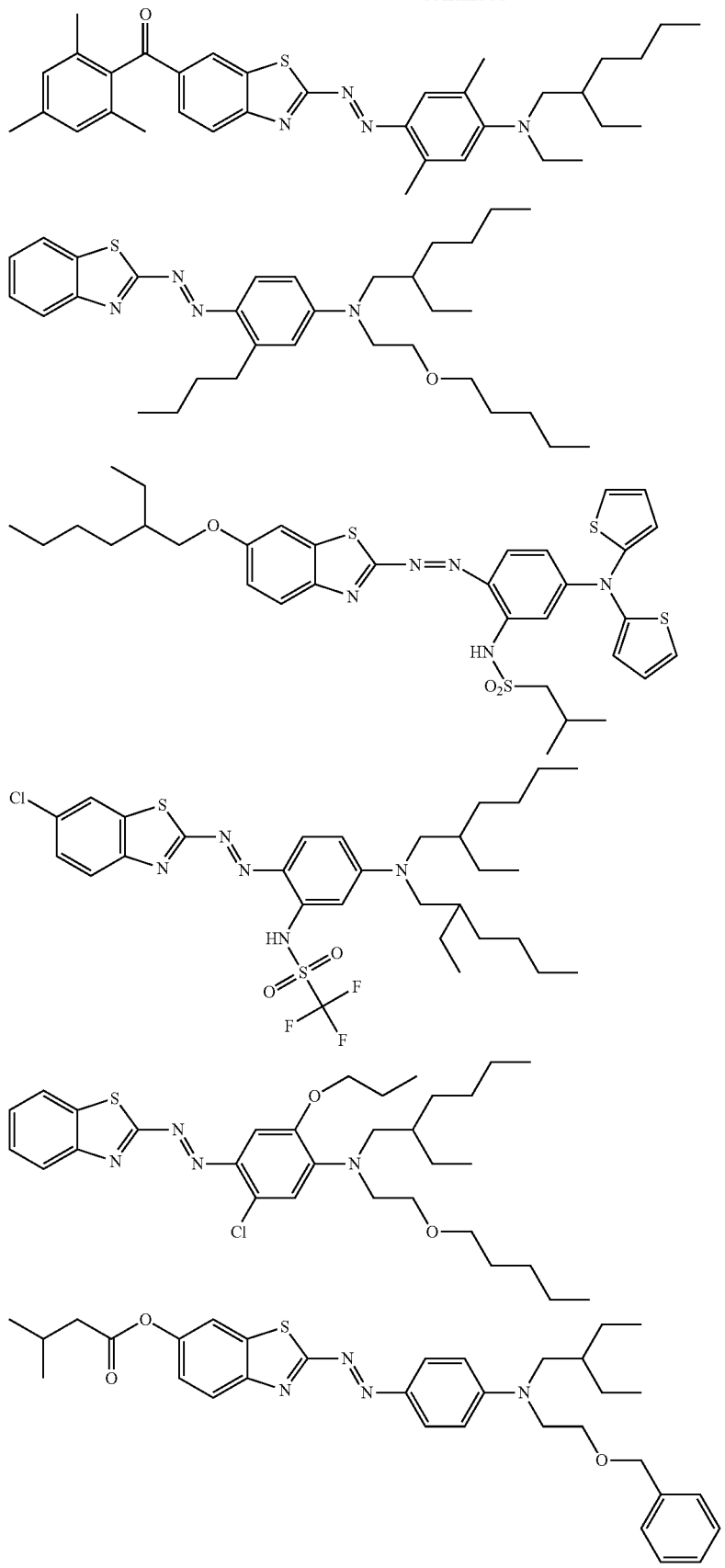

The heterocyclic compound represented by general formula (6) can be synthesized, for example, in accordance with the methods described in JP-A-10-204307 and JP-A-2000-280635.

Examples of the heterocyclic compounds include compounds represented by the following general formula (7).

[Chem. 27]

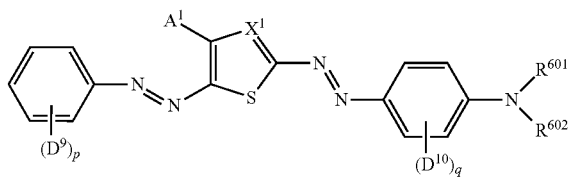

(7)

[In general formula (7),
$R^{601}$, $R^{602}$, $D^9$, and $D^{10}$ each independently represent any substituent,
$A^1$ represents a hydrogen atom or any substituent,
p represents an integer of 0-5, and when p is 2 or larger, the two or more $D^9$s present in the molecule may be the same or different,
q represents an integer of 0-4, and when q is 2 or larger, the two or more $D^{10}$s present in the molecule may be the same or different,
$X^1$ represents a nitrogen atom or a methine group which may have a halogen atom, a cyano group, or a —$COOR^{605}$ group as a substituent, and
$R^{605}$ represents a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.]

<$R^{601}$ and $R^{602}$>

$R^{601}$ and $R^{602}$ each independently represent any substituent. Although $R^{601}$ and $R^{602}$ are not particularly limited so long as the effects of the invention are not lessened thereby, it is preferable that $R^{601}$ and $R^{602}$ each should be an alkyl group which has 1-20 carbon atoms and may have a substituent. Specifically, the term "alkyl group" has the same meaning as the alkyl group, examples of which were shown above with regard to the $R^1$ contained in general formula (1), and the substituents which may be possessed are also the same.

(Alkyl Group which May have a Substituent)

The alkyl groups represented by $R^{601}$ and $R^{602}$ each preferably have 4 or more carbon atoms, and more preferably are an alkyl group having 5 or more carbon atoms. The number of carbon atoms thereof is preferably 16 or less, more preferably 12 or less. In cases when the number of carbon atoms thereof is in an adequate range, the compound tends to have excellent solubility in solvents and have a high gram extinction coefficient.

It is preferable that $R^{601}$ and/or $R^{602}$ should be a branched alkyl group, and it is more preferable that $R^{601}$ and/or $R^{602}$ should be a branched alkyl group having 5-20 carbon atoms. It is even more preferable that $R^{601}$ and $R^{602}$ should both be a branched alkyl group. The branched groups tend to bring about improved solubility in solvents.

<$D^9$>

$D^9$ represents any substituent, and is not particularly limited so long as the effects of the invention are not lessened thereby. It is, however, preferable that $D^9$ should be a halogen atom, a cyano group, an alkyl group which has 1-20 carbon atoms and may have a substituent, an alkoxy group which has 1-20 carbon atoms and may have a substituent, a —$COOR^{604}$ group, a —$COR^{609}$ group, an —$OCOR^{610}$ group, or the like, because this compound tends to have excellent solubility in solvents and a high gram extinction coefficient.

$R^{604}$, $R^{609}$, and $R^{610}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent. Symbol p represents an integer of 0-5. When p is 2 or larger, the two or more $D^9$s presents in the molecule may be the same or different.

<$D^{10}$>

$D^{10}$ represents any substituent, and is not particularly limited so long as the effects of the invention are not lessened thereby. It is, however, preferable that $D^{10}$ should be a halogen atom, an alkyl group which has 1-20 carbon atoms and may have a substituent, an alkoxy group which has 1-20 carbon atoms and may have a substituent, an —$NHCOR^{603}$ group, an —$NHSO_2R^{608}$ group, or the like, because this compound tends to have excellent solubility in solvents and a high gram extinction coefficient.

$R^{603}$ and $R^{608}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

Symbol q represents an integer of 0-5. When q is 2 or larger, the two or more $D^{10}$s presents in the molecule may be the same or different.

<$A^1$>

$A^1$ represents a hydrogen atom or any substituent. $A^1$ is not particularly limited so long as the effects of the invention are not lessened thereby. However, it is preferable from the standpoints of high solubility and high extinction coefficient that $A^1$ should represent a hydrogen atom, an alkyl group which may have a substituent, a halogen atom, a cyano group, an aryl group which has 6-20 carbon atoms and may have a substituent, a heteroaryl group which has 2-20 carbon atoms and may have a substituent, an alkoxy group which has 1-20 carbon atoms and may have a substituent, or a —$COOR^{606}$ group, and that $R^{606}$ should represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

<$X^1$>

$X^1$ represents a nitrogen atom or a methine group which may have a halogen atom, a cyano group, or a —$COOR^{605}$ group as a substituent. $R^{605}$ represents a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

The term "alkyl group which may have a substituent" for $R^{605}$ specifically has the same meaning as the alkyl group which may have a substituent, examples of which were shown above with regard to the $R^1$ contained in general formula (1), and the substituents which may be possessed are also the same. The number of carbon atoms of the alkyl group represented by $R^{605}$ is preferably 16 or less, more preferably 10 or less, even more preferably 6 or less. In cases when the number of carbon atoms thereof is in an adequate range, the compound tends to have excellent solubility in solvents and a high gram extinction coefficient.

The term "aryl group which may have a substituent" for $R^{605}$ specifically has the same meaning as the aryl group which may have a substituent, examples of which were shown above with regard to the $R^{101}$ contained in general formula (4), and the substituents which may be possessed are also the same. Furthermore, the term "heteroaryl group" for $R^{605}$ specifically has the same meaning as the heteroaryl group, examples of which were shown above with regard to the $R^{104}$ contained in general formula (4), and the substituents which may be possessed are also the same.

(Alkyl Group which May have a Substituent)

The term "alkyl group which may have a substituent" for $D^9$, $D^{10}$, $R^{603}$, $R^{604}$, $R^{605}$, $R^{606}$, $R^{608}$, $R^{609}$, $R^{610}$, and $A^1$ specifically has the same meaning as the alkyl group which may have a substituent, examples of which were shown above with regard to the contained in general formula (1), and the substituents which may be possessed are also the same. The number of carbon atoms of each of these alkyl groups is preferably 16 or less, more preferably 10 or less, especially preferably 6 or less. In cases when the number of carbon atoms thereof is in an adequate range, the compound tends to have excellent solubility in solvents and a high gram extinction coefficient.

(Alkoxy Group which May have a Substituent)

The term "alkoxy group which may have a substituent" for $D^9$, $D^{10}$, and $A^1$ has the same meaning as the alkoxy group which may have a substituent, examples of which were shown above with regard to the $R^1$ contained in general formula (1), and the substituents which may be possessed are also the same.

The number of carbon atoms of each of the alkoxy groups represented by $D^9$, $D^{10}$, and $A^1$ is preferably 16 or less, more preferably 10 or less, especially preferably 6 or less. In cases when the number of carbon atoms thereof is in an adequate range, the compound tends to have excellent solubility in solvents and a high gram extinction coefficient.

(Aryl Group which May have a Substituent)

The term "aryl group which may have a substituent" for $R^{603}$, $R^{604}$, $R^{605}$, $R^{606}$, $R^{608}$, $R^{609}$, $R^{610}$, and $A^1$ specifically has the same meaning as the aryl group which may have a substituent, examples of which were shown above with regard to the $R^{101}$ contained in general formula (4), and the substituents which may be possessed are also the same.

(Heteroaryl Group which May have a Substituent)

The term "heteroaryl group which may have a substituent" for $R^{603}$, $R^{604}$, $R^{605}$, $R^{606}$, $R^{608}$, $R^{609}$, $R^{610}$, and $A^1$ specifically has the same meaning as the heteroaryl group which may have a substituent, examples of which were shown above with regard to the $R^{101}$ contained in general formula (4), and the substituents which may be possessed are also the same.

Specific examples of the compounds represented by general formula (7) are shown below. However, the heterocyclic compounds should not be construed as being limited to the following examples unless the compounds depart from the spirit thereof.

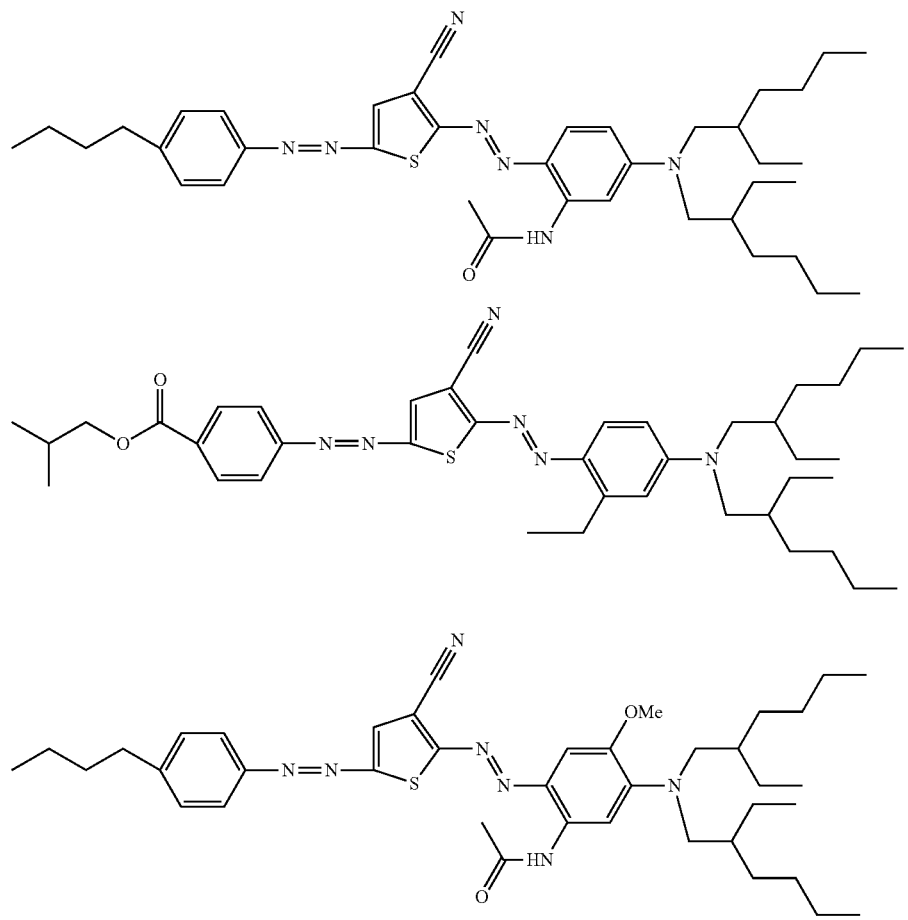

[Chem. 28]

-continued
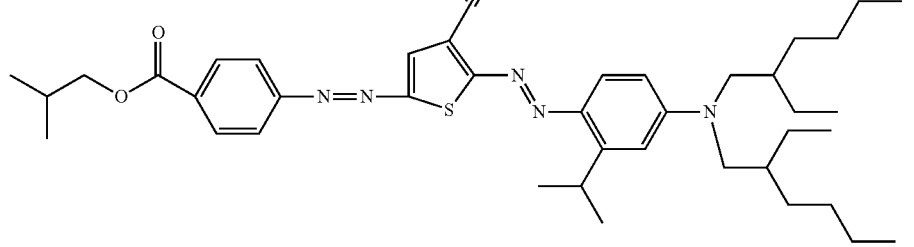
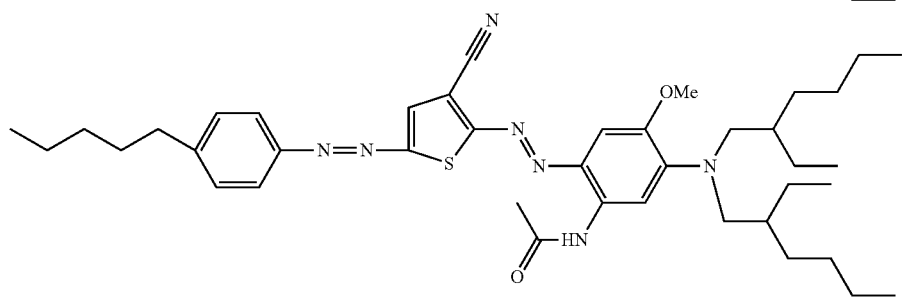
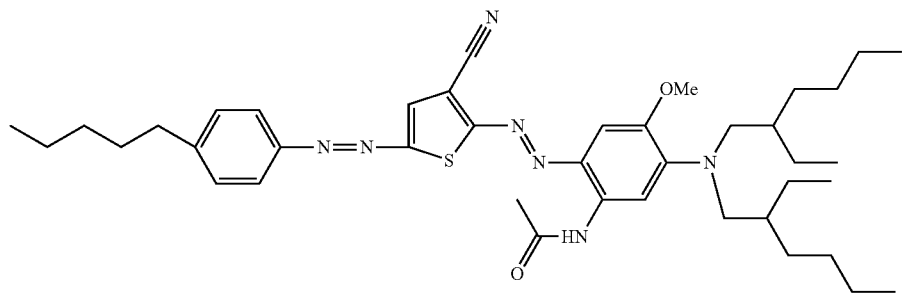
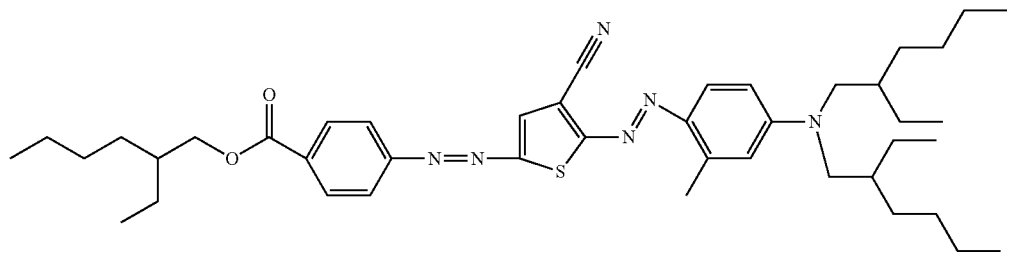
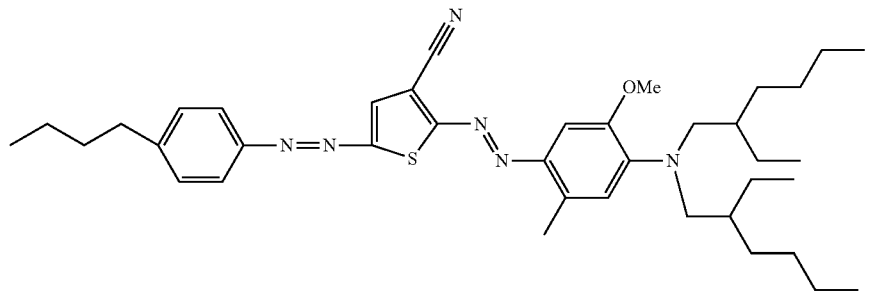
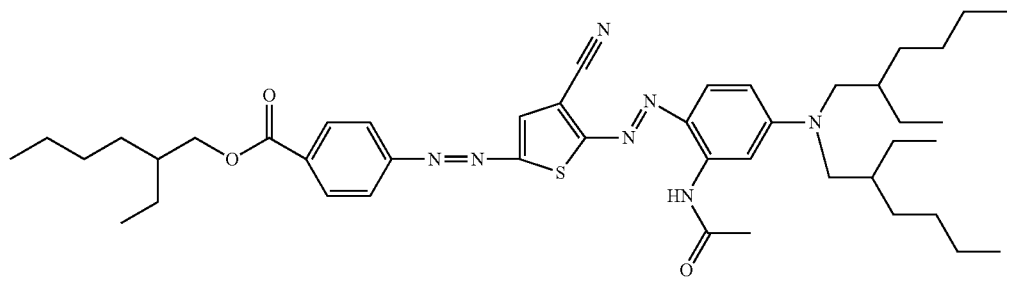

-continued
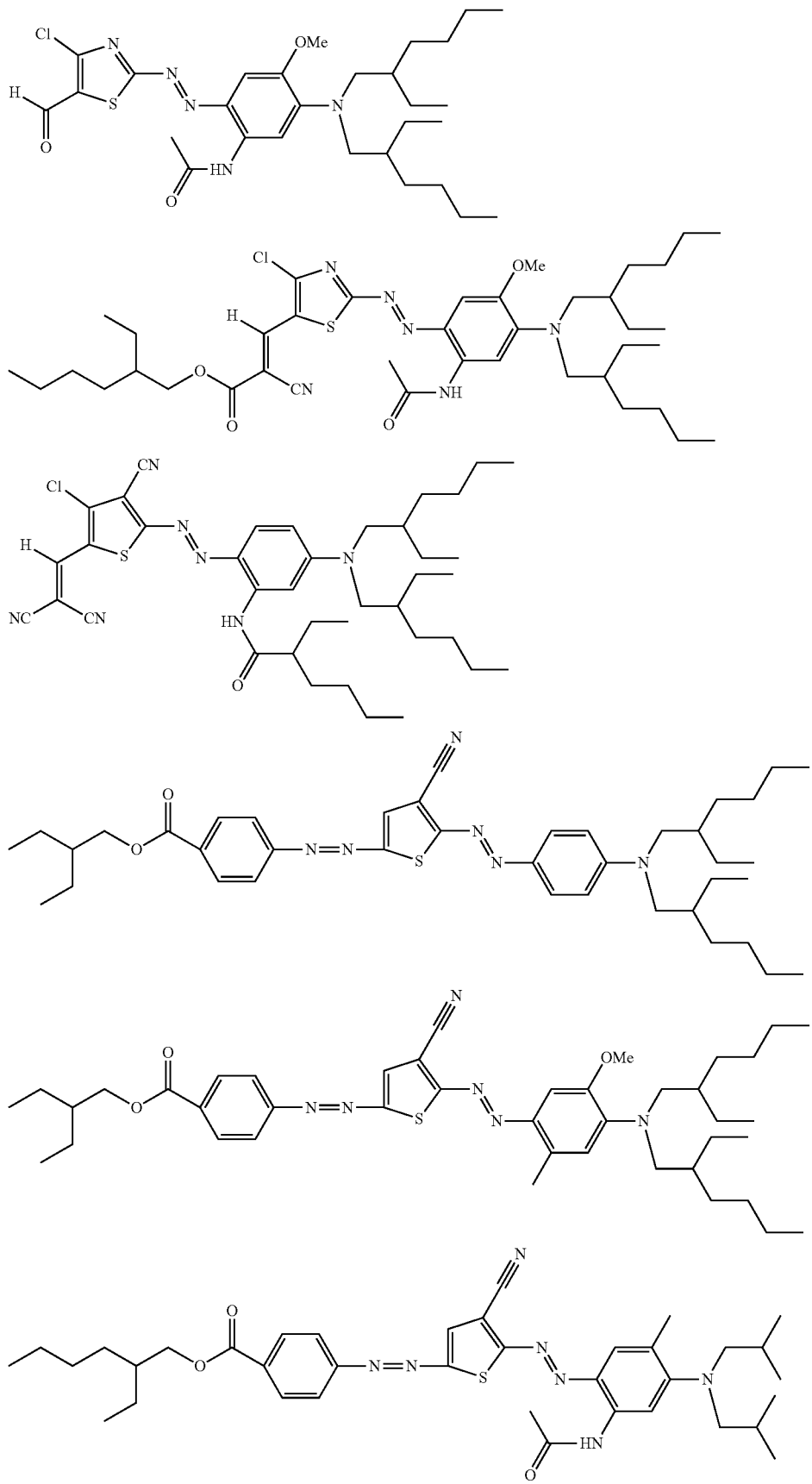

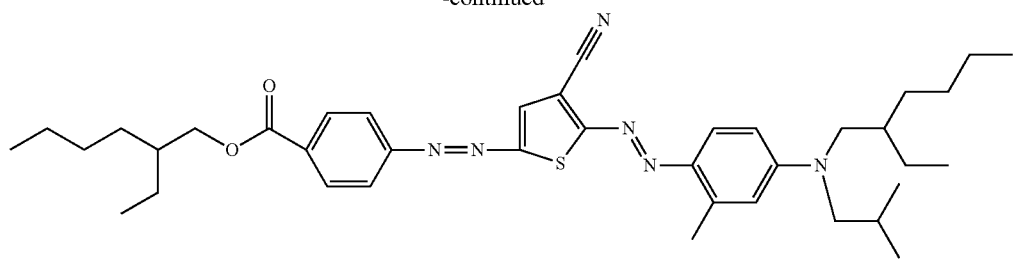
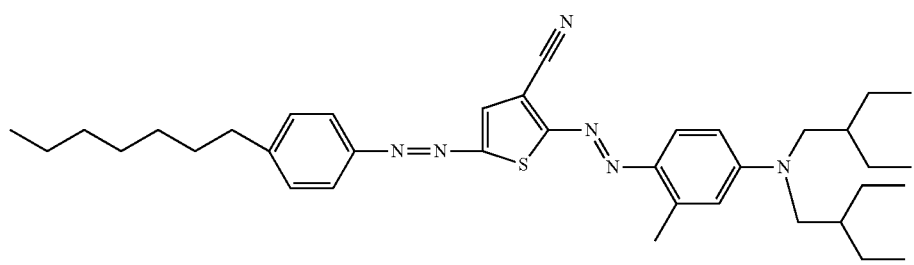
[Chem. 29]
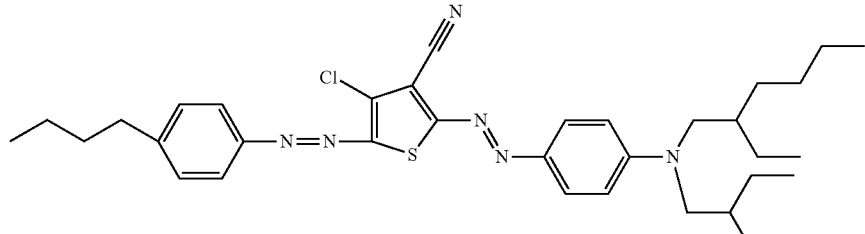
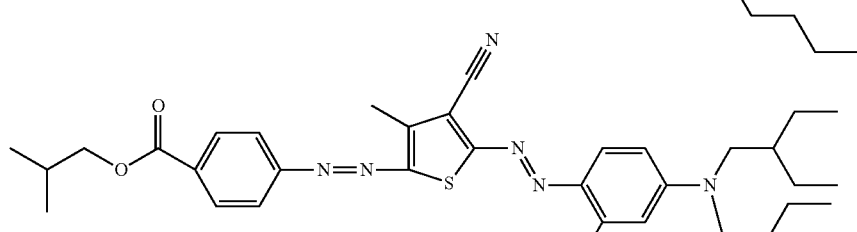
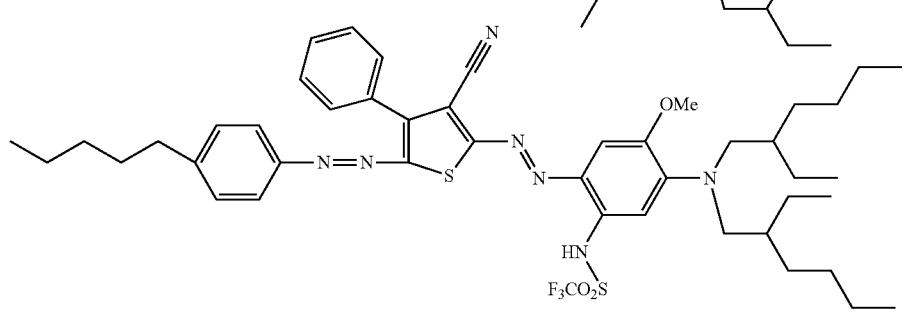
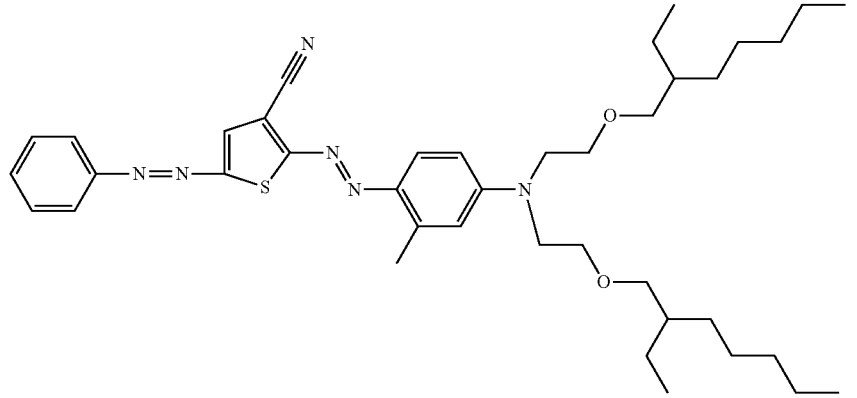

-continued
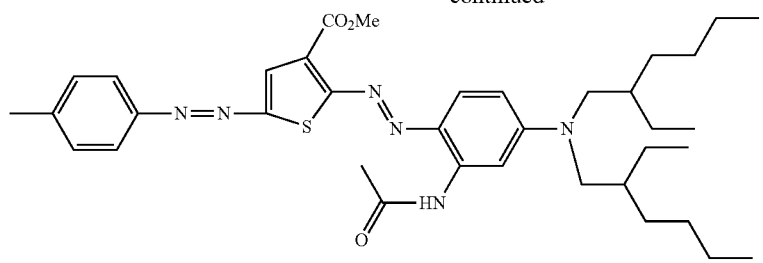
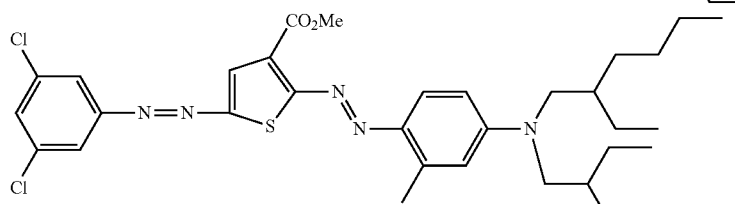
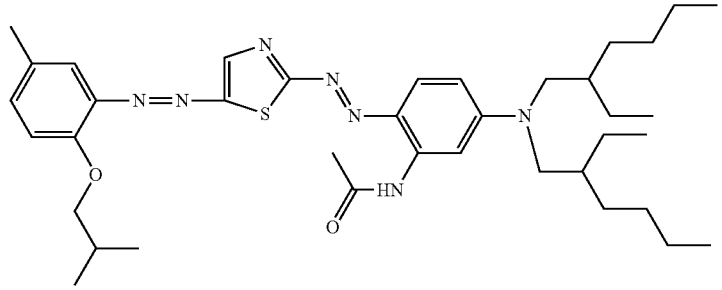
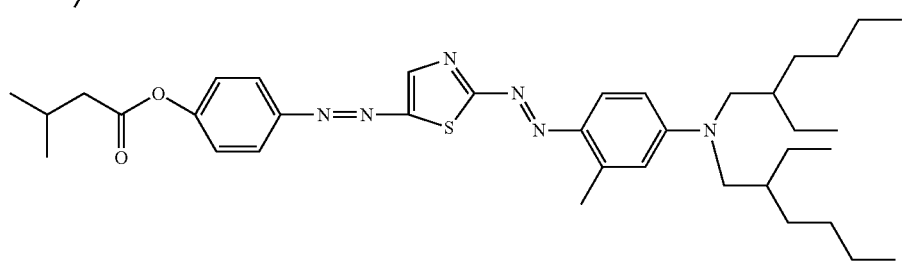
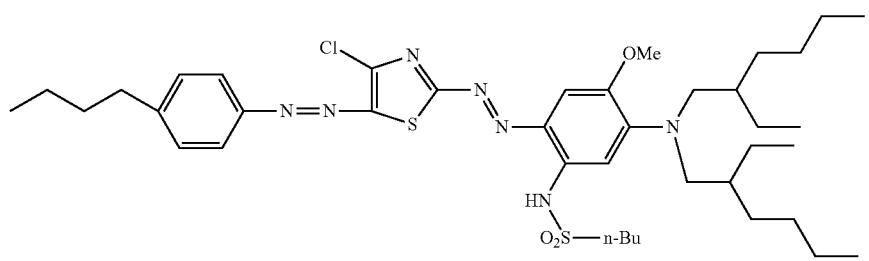
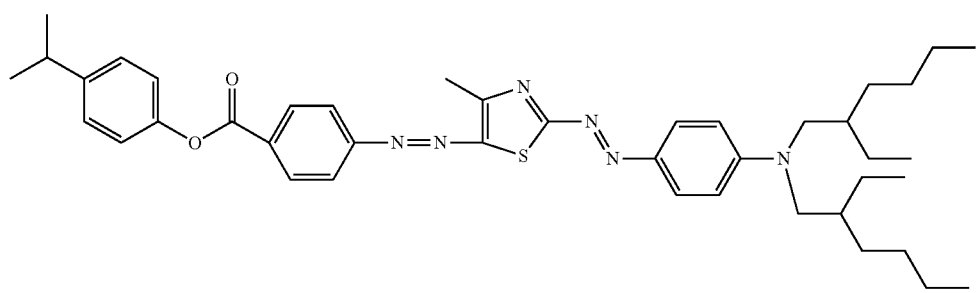

-continued
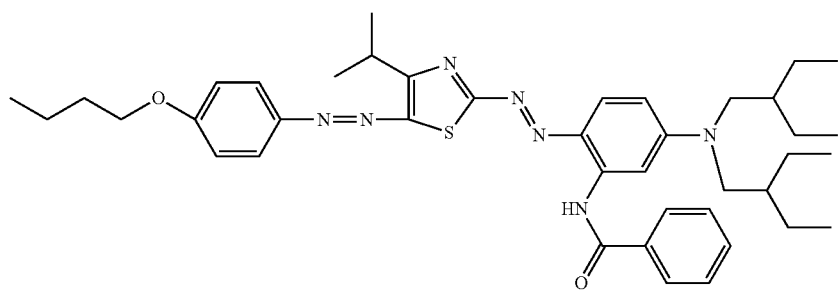
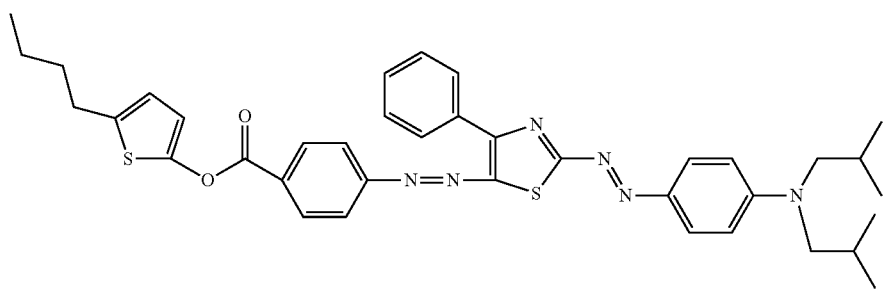
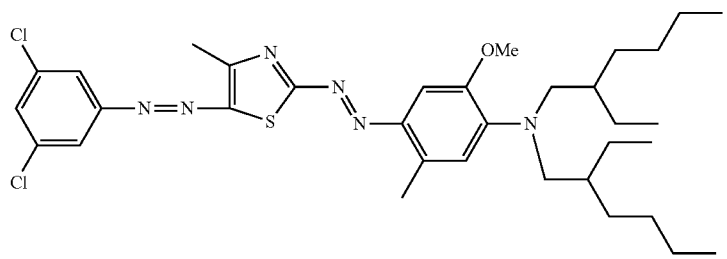
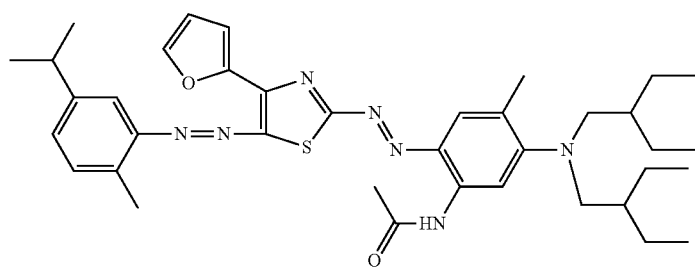
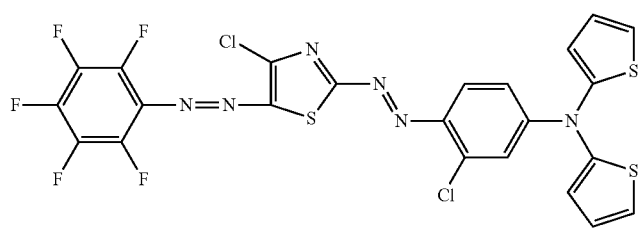
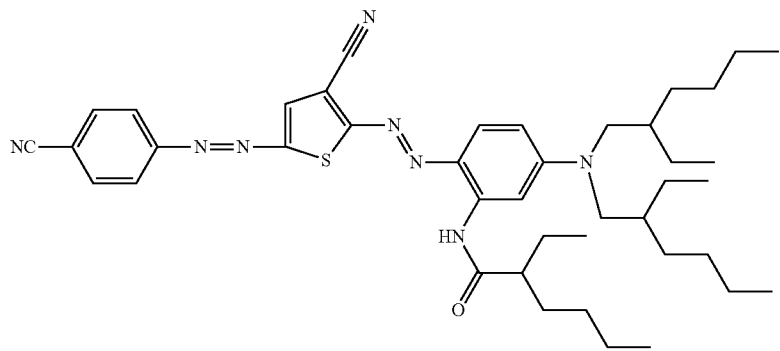

The heterocyclic compound represented by general formula (7) can be synthesized, for example, in accordance with the method described in JP-A-3-256793.

The molecular weight of each of the heterocyclic compounds represented by general formulae (4) to (7), etc. explained above, including the substituents in the case where the compound has substituents, is usually 2,000 or less, preferably 1,000 or less, and is usually 300 or higher, preferably 400 or higher, from the standpoint of gram extinction coefficient.

Specific examples of the cyanovinyl compounds are not particularly limited. However, compounds represented by the following general formula (8) are preferred.

[Chem. 30]

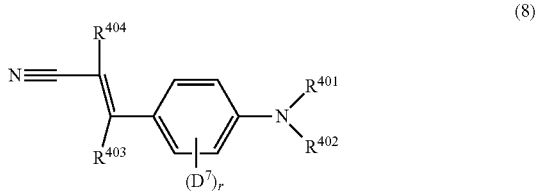

(8)

[In general formula (8),
$R^{401}$, $R^{402}$, and $D^7$ each independently represent any substituent,
$R^{403}$ and $R^{404}$ each independently represent a hydrogen atom or any substituent, and
r represents an integer of 0-4, and when r is 2 or large, the two or more $D^7$s present in the molecule may be the same or different.]

<$R^{401}$ and $R^{402}$>

$R^{401}$ and $R^{402}$ each independently represent any substituent. $R^{401}$ and $R^{402}$ are not particularly limited unless the effects of the invention are lessened thereby. However, from the standpoints of high extinction coefficient and high solubility in solvents, it is preferable that $R^{401}$ and $R^{402}$ should each independently be an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for $R^{401}$ and $R^{402}$ specifically has the same meaning as the alkyl group which may have a substituent, examples of which were shown above with regard to the $R^1$ contained in general formula (1), and the substituents which may be possessed are also the same. The number of carbon atoms of each of the alkyl groups represented by $R^{401}$ and $R^{402}$ is preferably 2 or larger, more preferably 4 or larger. Meanwhile, the number of carbon atoms thereof is preferably 16 or less, more preferably 12 or less. In cases when the number of carbon atoms thereof is in an adequate range, there are cases where the compound can have excellent solubility in solvents and a high gram extinction coefficient.

(Aryl Group which May have a Substituent)

The term "aryl group" for $R^{401}$ and $R^{402}$ specifically has the same meaning as the aryl group, examples of which were shown above with regard to the $R^{101}$ contained in general formula (4), and the substituents which may be possessed are also the same as those of the aryl group which were shown above as examples with regard to the $R^{101}$ contained in general formula (4).

(Heteroaryl Group which May have a Substituent)

The term "heteroaryl group" for $R^{401}$ and $R^{402}$ specifically has the same meaning as the heteroaryl group, examples of which were shown above with regard to the $R^{101}$ contained in general formula (4), and the substituents which may be possessed are also the same as those of the heteroaryl group which were shown above as examples with regard to the $R^{101}$ contained in general formula (4).

<$R^{403}$, $R^{404}$, and $R^{405}$>

$R^{403}$ and $R^{404}$ each independently represent a hydrogen atom or any substituent. $R^{403}$ and $R^{404}$ are not particularly limited unless the effects of the invention are lessened thereby. However, from the standpoints of high extinction coefficient and high solubility, it is preferable that $R^{403}$ should be a hydrogen atom or a cyano group and $R^{404}$ should be a cyano group or a —$COR^{405}$ group.

$R^{405}$ represents a hydrogen atom, an alkyl group which has 1-20 carbon atoms and may have a substituent, an alkoxy group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for $R^{405}$ specifically has the same meaning as the alkyl group which may have a substituent, examples of which were shown above with regard to the $R^1$ contained in general formula (1), and the substituents which may be possessed are also the same. The number of carbon atoms of the alkyl group represented by $R^{405}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group which may have a substituent" for $R^{405}$ has the same meaning as the alkoxy group which may have a substituent, examples of which were shown above with regard to the $R^1$ contained in general formula (1), and the substituents which may be possessed are also the same. The number of carbon atoms of the alkoxy group represented by $R^{405}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group which may have a substituent" for $R^{405}$ specifically has the same meaning as the aryl group which may have a substituent, examples of which were shown above with regard to the $R^{101}$ contained in general formula (4), and the substituents which may be possessed are also the same as those of the aryl group which were shown above as examples with regard to the $R^{101}$ contained in general formula (4).

(Heteroaryl Group which May have a Substituent)

The term "heteroaryl group which may have a substituent" for $R^{405}$ specifically has the same meaning as the heteroaryl group which may have a substituent, examples of which were shown above with regard to the $R^{101}$ contained in general formula (4), and the substituents which may be possessed are also the same as those of the heteroaryl group which were shown above as examples with regard to the $R^{101}$ contained in general formula (4).

<D⁷>

D⁷ represents any substituent. D⁷ is not particularly limited unless the effects of the invention are lessened thereby. However, from the standpoints of high extinction coefficient and high solubility in solvents, it is preferable that D⁷ should be a hydrogen atom, a halogen atom, an alkyl group which has 1-20 carbon atoms and may have a substituent, an alkoxy group which has 1-20 carbon atoms and may have a substituent, an —NHCOR$^{406}$ group, or an —NHSO$_2$R$^{407}$ group.

Symbol r represents an integer of 0-4. When r is 2 or larger, the two or more D⁷s present in the molecule may be the same or different.

R$^{406}$ and R$^{407}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for D⁷, R$^{406}$, and R$^{407}$ specifically has the same meaning as the alkyl group which may have a substituent, examples of which were shown above with regard to the R$^1$ contained in general formula (1), and the substituents which may be possessed are also the same.

The number of carbon atoms of each of the alkyl groups represented by D⁷, R$^{406}$, and R$^{407}$ is preferably 2 or larger, more preferably 4 or larger. Meanwhile, the number of carbon atoms thereof is preferably 16 or less, more preferably 12 or less. In cases when the number of carbon atoms thereof is in an adequate range, there are cases where the compound can have excellent solubility in solvents and a high gram extinction coefficient.

(Alkoxy Group which May have a Substituent)

The term "alkoxy group which may have a substituent" for D⁷ has the same meaning as the alkoxy group which may have a substituent, examples of which were shown above with regard to the R$^1$ contained in general formula (1), and the substituents which may be possessed are also the same. The number of carbon atoms of the alkoxy group represented by D⁷ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group which may have a substituent" for R$^{406}$ and R$^{407}$ specifically has the same meaning as the aryl group which may have a substituent, examples of which were shown above with regard to the R$^{101}$ contained in general formula (4), and the substituents which may be possessed are also the same as those of the aryl group which were shown above as examples with regard to the R$^{101}$ contained in general formula (4).

(Heteroaryl Group which May have a Substituent)

The term "heteroaryl group which may have a substituent" for R$^{406}$ and R$^{407}$ specifically has the same meaning as the heteroaryl group which may have a substituent, examples of which were shown above with regard to the R$^{101}$ contained in general formula (4), and the substituents which may be possessed are also the same as those of the heteroaryl group which were shown above as examples with regard to the R$^{101}$ contained in general formula (4).

Specific examples of the cyanovinyl compounds represented by general formula (8) are shown below. However, the cyanovinyl compounds should not be construed as being limited to the following examples unless the compounds depart from the spirit thereof.

[Chem. 31]

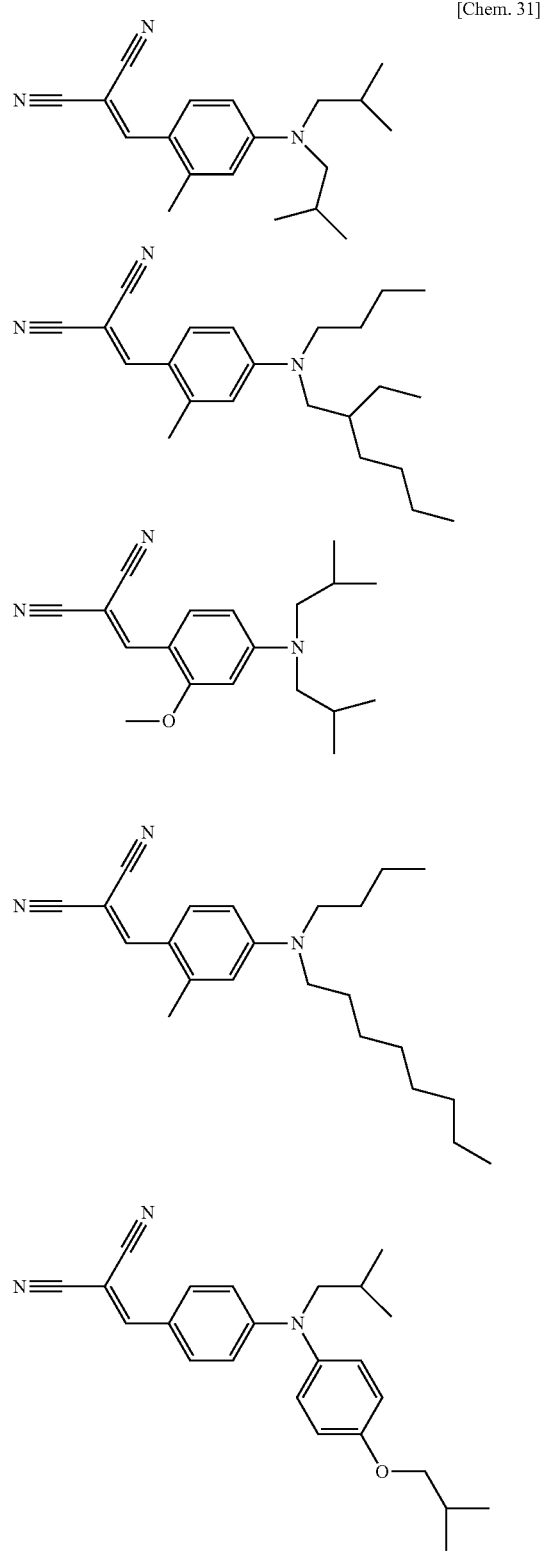

75
-continued
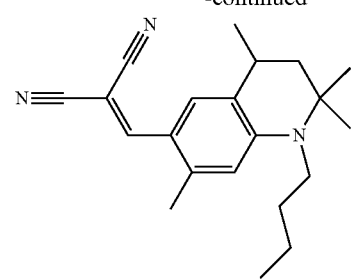
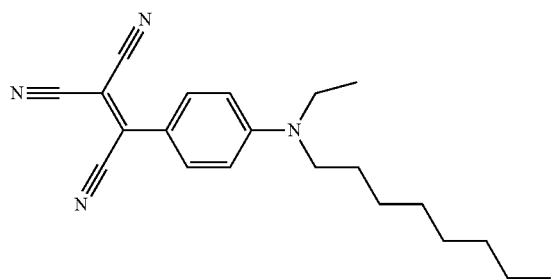
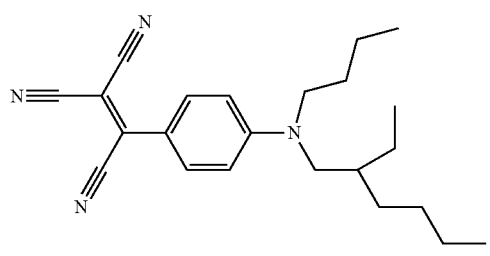
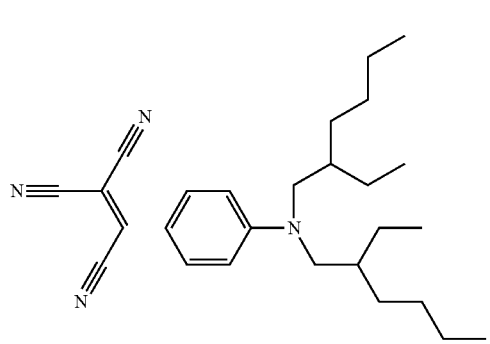
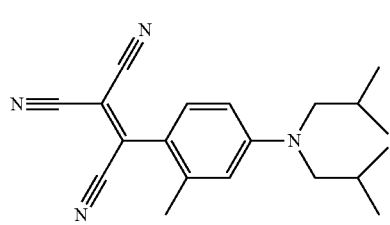
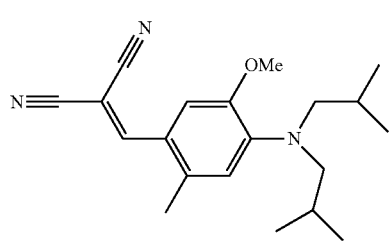
76
-continued
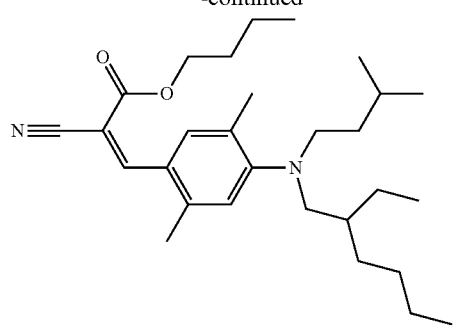
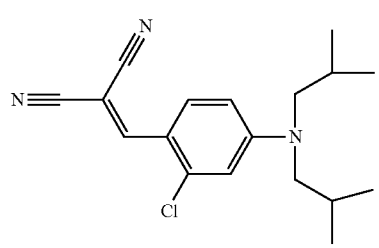
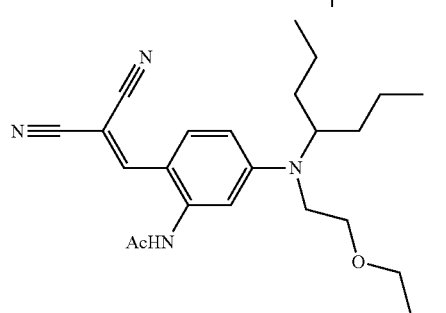
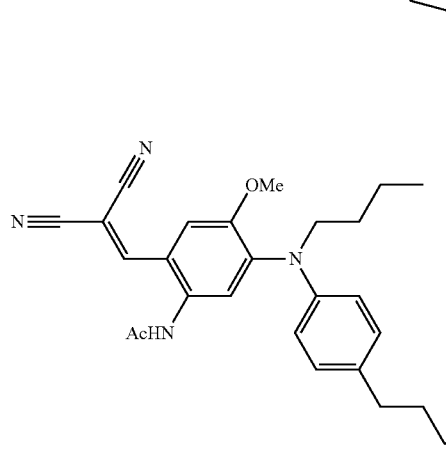
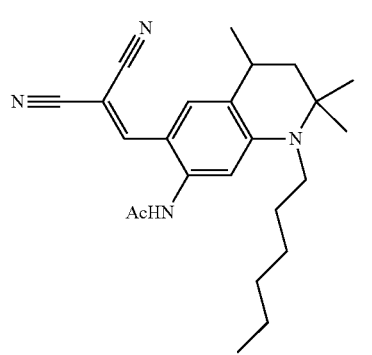

77
-continued
[Chem. 32]
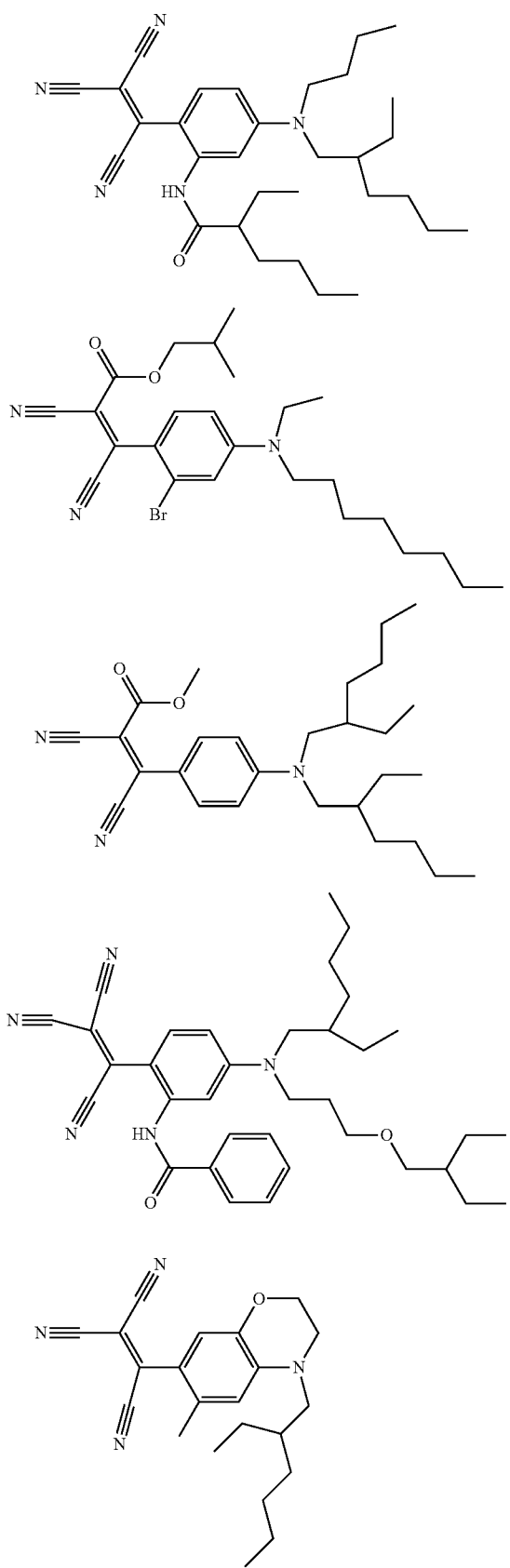
78
-continued
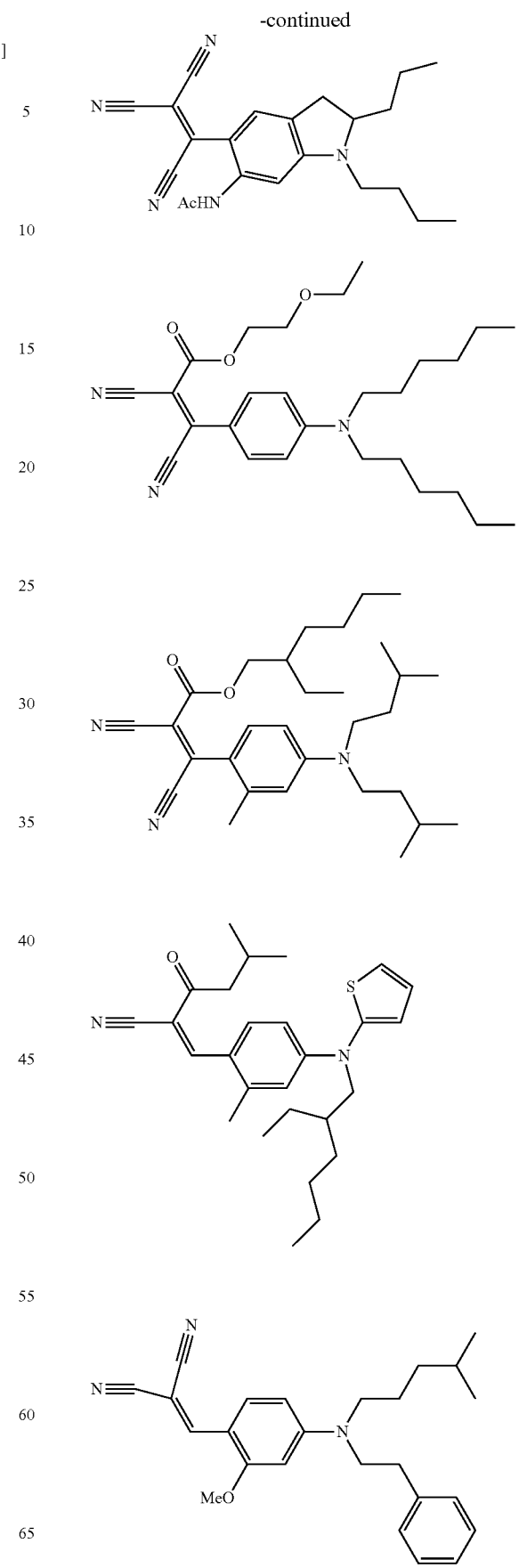

79
-continued

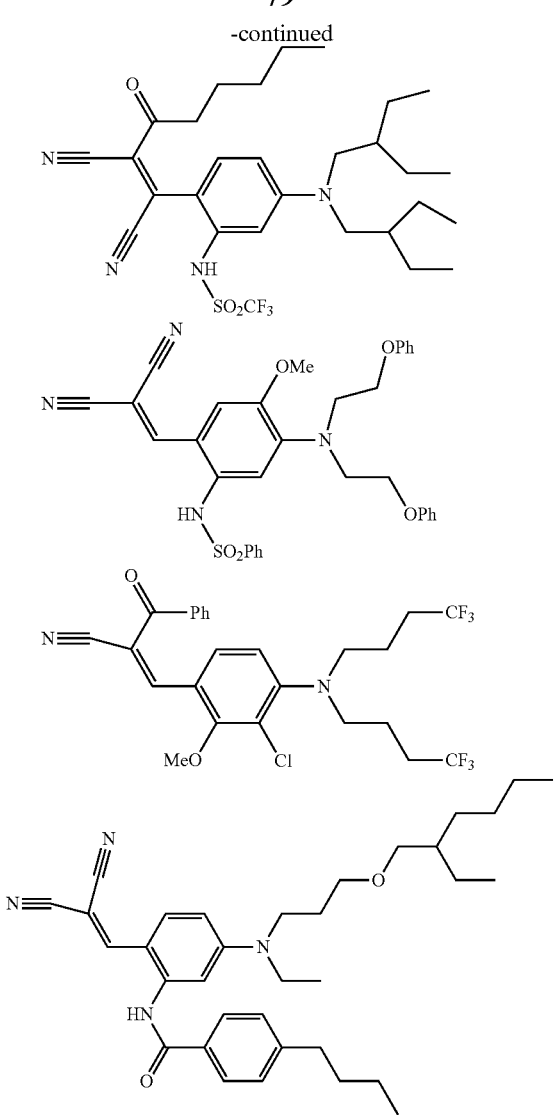

The compound represented by general formula (8) can be synthesized, for example, in accordance with the method described in JP-A-11-100523 or JP-A-2000-247942.

Specific examples of the anthraquinone compounds are not particularly limited. However, compounds represented by the following general formula (9) are preferred.

[Chem. 33]

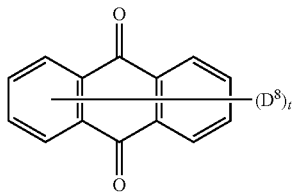

(9)

[In general formula (9),
$D^8$ represents any substituent, and
t represents an integer of 0-8, and when t is 2 or larger, the two or more $D^8$s present in the molecule may be the same or different.]

80

<$D^8$>

$D^8$ represents any substituent. $D^8$ is not particularly limited unless the effects of the invention are lessened thereby. However, from the standpoints of high extinction coefficient and high solubility in solvents, it is preferable that $D^8$ should be a halogen atom, an alkyl group which has 1-20 carbon atoms and may have a substituent, an alkoxy group which has 1-20 carbon atoms and may have a substituent, a cyano group, a hydroxy group, an amino group, a nitro group, a —$COOR^{501}$ group, an —$NHR^{502}$ group, an —$NHCOR^{503}$ group, or an —$SR^{504}$ group.

Symbol t represents an integer of 0-8. When t is 2 or larger, the two or more $D^8$s present in the molecule may be the same or different.

$R^{501}$, $R^{502}$, $R^{503}$, and $R^{504}$ each independently represent a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

(Alkyl Group which May have a Substituent)

The term "alkyl group which may have a substituent" for $D^8$, $R^{501}$, $R^{502}$, $R^{503}$, and $R^{504}$ specifically has the same meaning as the alkyl group which may have a substituent, examples of which were shown above with regard to the $R^1$ contained in general formula (1), and the substituents which may be possessed are also the same. The number of carbon atoms of each of the alkyl groups represented by $D^8$, $R^{501}$, $R^{502}$, $R^{503}$, and $R^{504}$ is preferably 16 or less, more preferably 10 or less, especially preferably 6 or less. In cases when the number of carbon atoms thereof is in an adequate range, there are cases where the compound can have excellent solubility in solvents and a high gram extinction coefficient.

(Aryl Group which May have a Substituent)

The term "aryl group which may have a substituent" for $R^{501}$, $R^{502}$, $R^{503}$, and $R^{504}$ specifically has the same meaning as the aryl group which may have a substituent, examples of which were shown above with regard to the $R^{101}$ contained in general formula (4), and the substituents which may be possessed are also the same as those of the aryl group which were shown above as examples with regard to the $R^{101}$ contained in general formula (4). It is preferable that the aryl groups represented by $R^{502}$ and $R^{504}$ each should be a phenyl or naphthyl group which may have a substituent, from the standpoint of high solubility in solvents.

Preferred examples of the substituents which may be possessed by the phenyl group or naphthyl group include halogen atoms, alkyl groups having 1-10 carbon atoms, and alkoxy groups having 1-10 carbon atoms, from the standpoint of high solubility in solvents.

(Heteroaryl Group which May have a Substituent)

The term "heteroaryl group" for $R^{501}$, $R^{502}$, $R^{503}$, and $R^{504}$ specifically has the same meaning as the heteroaryl group, examples of which were shown above with regard to the $R^{101}$ contained in general formula (4), and the substituents which may be possessed are also the same as those of the heteroaryl group which were shown above as examples with regard to the $R^{101}$ contained in general formula (4).

Specific examples of the anthraquinone compounds represented by general formula (9) are shown below. However, the anthraquinone compounds should not be construed as being limited to the following examples unless the compounds depart from the spirit thereof.

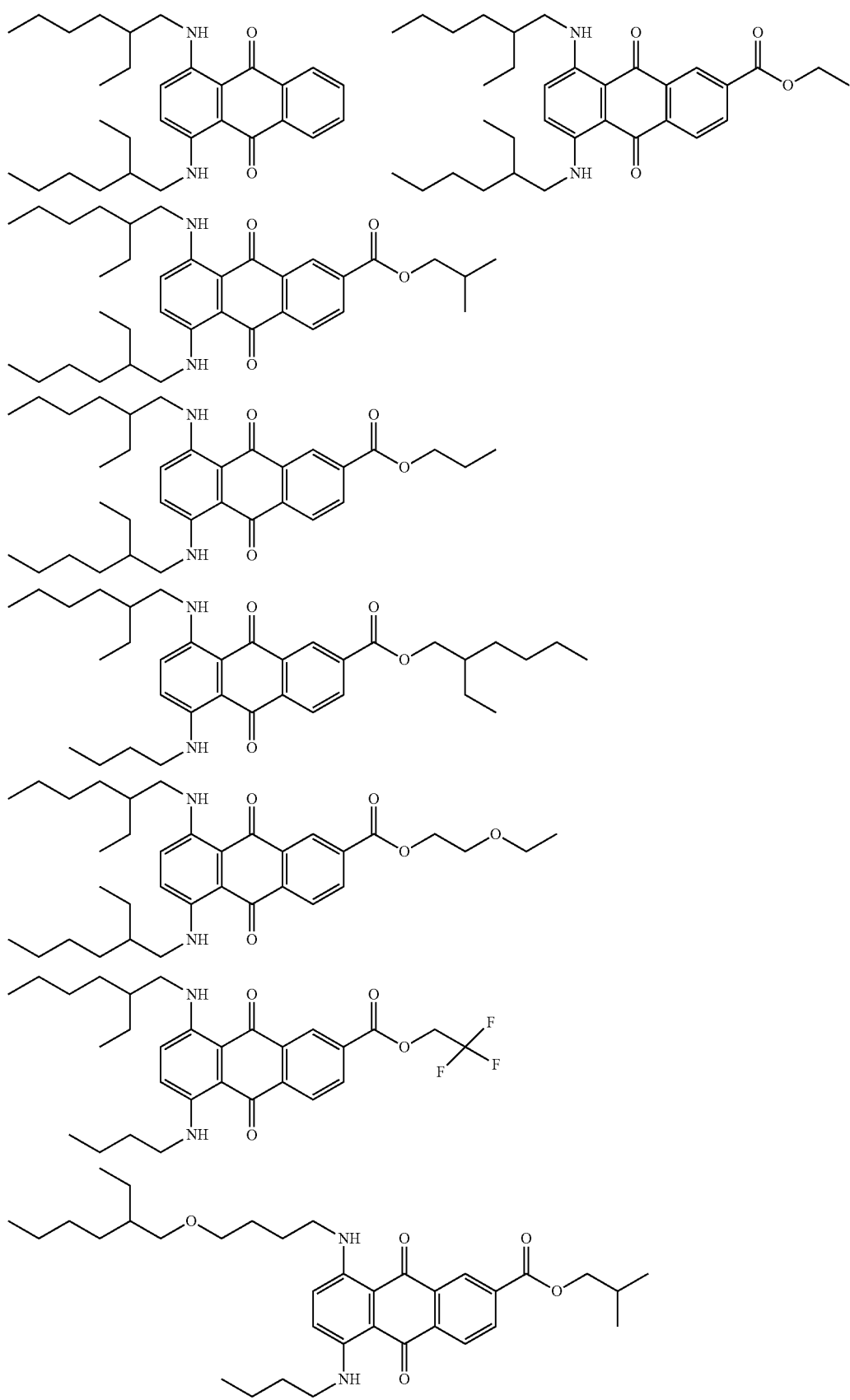

-continued
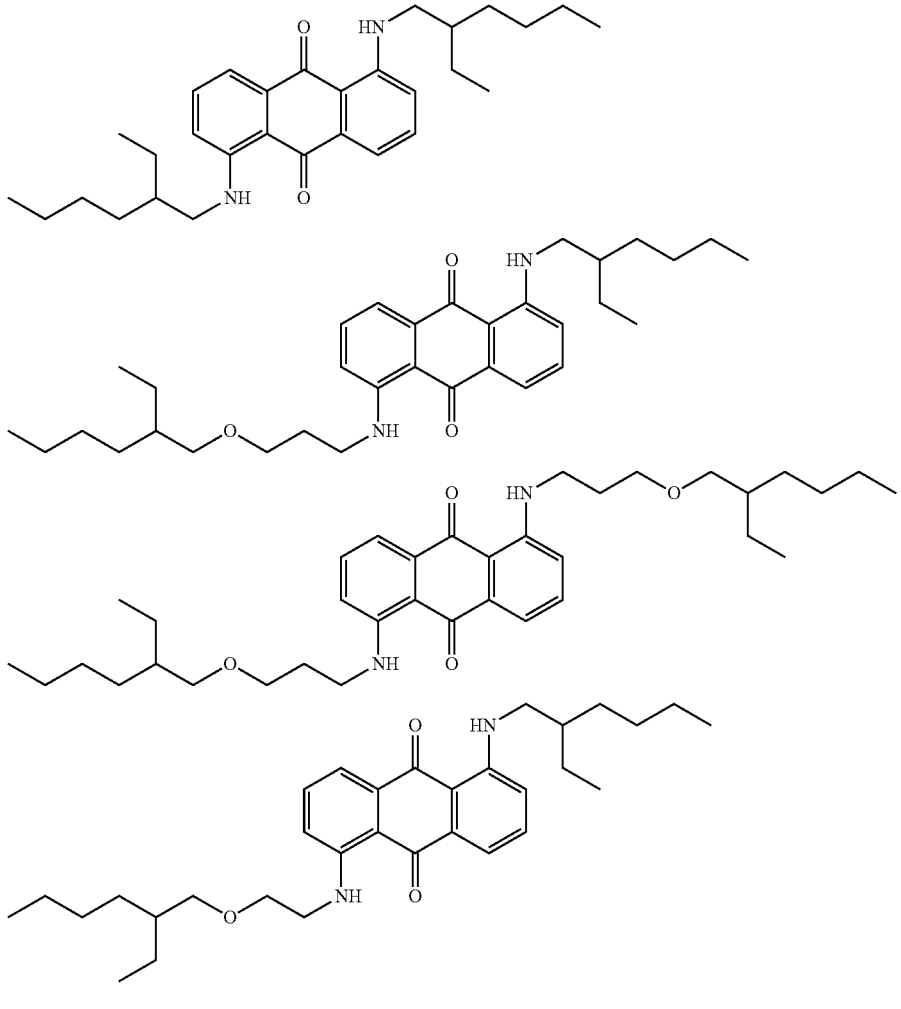
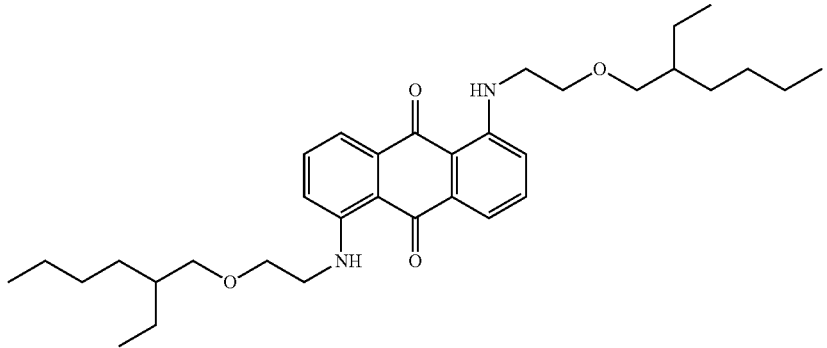
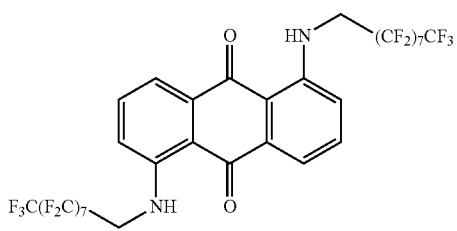

-continued
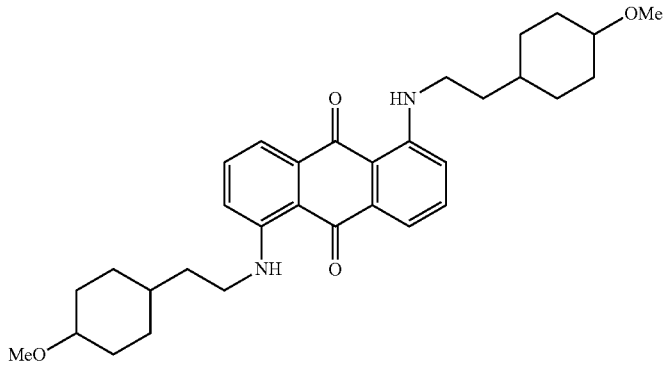
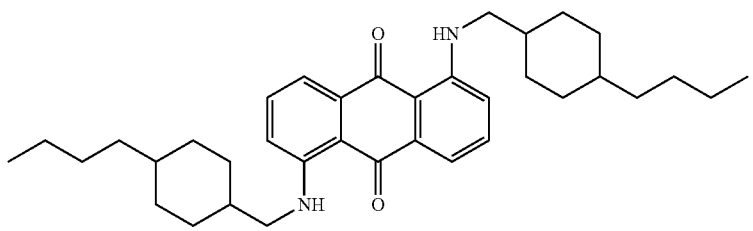
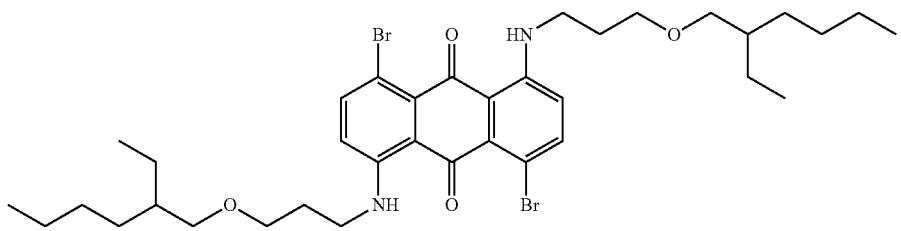
[Chem. 35]
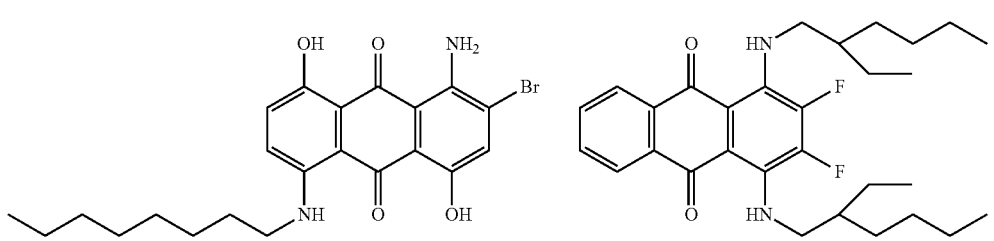
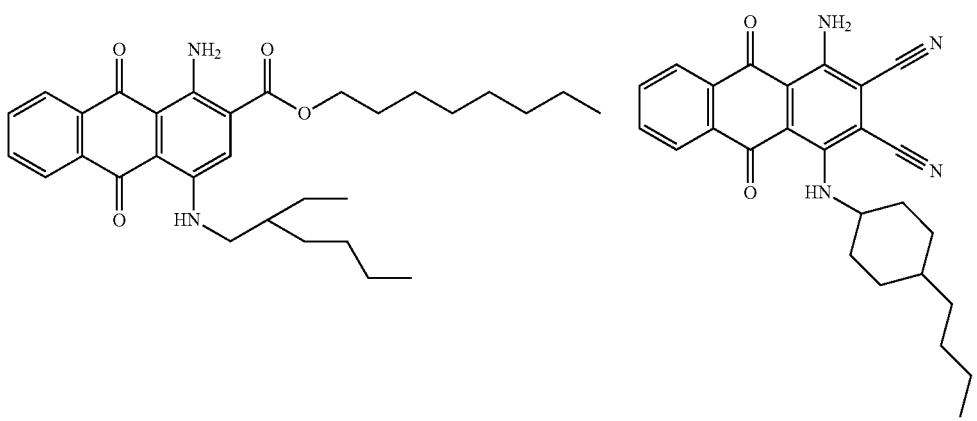

-continued
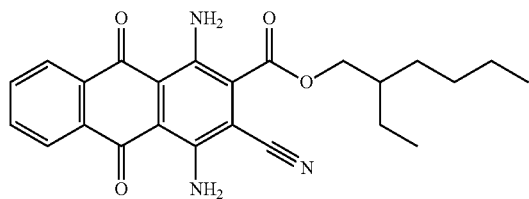 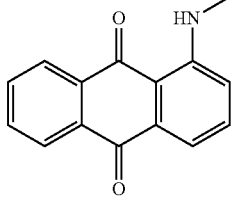
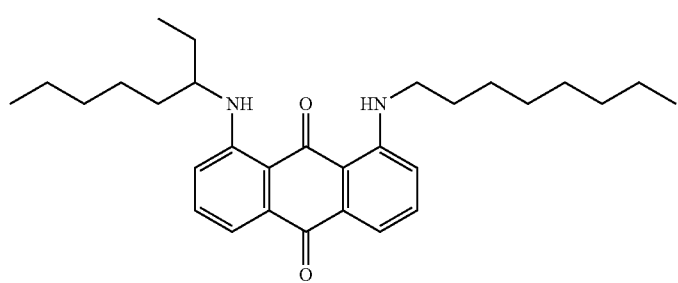
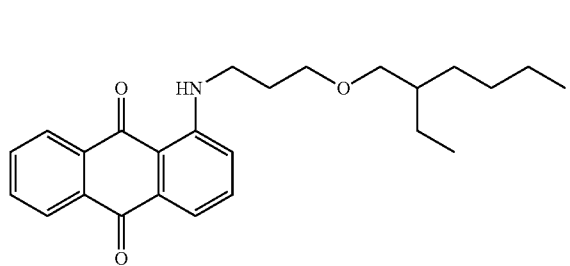 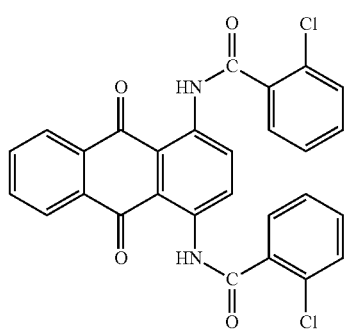
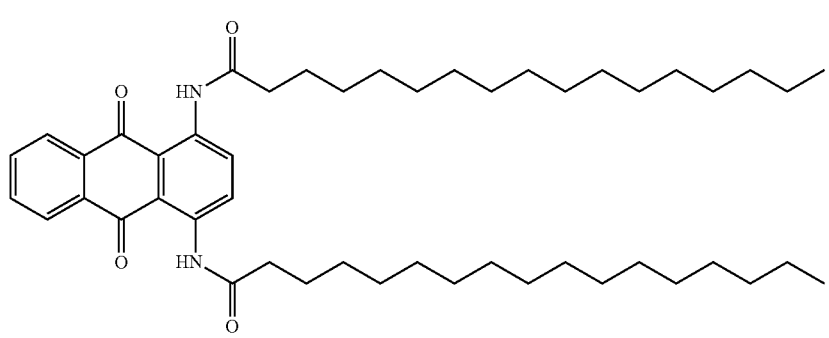
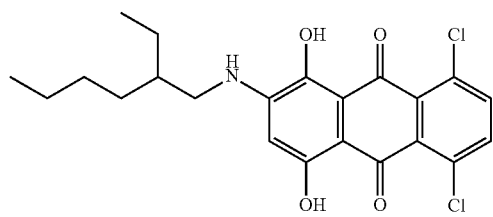
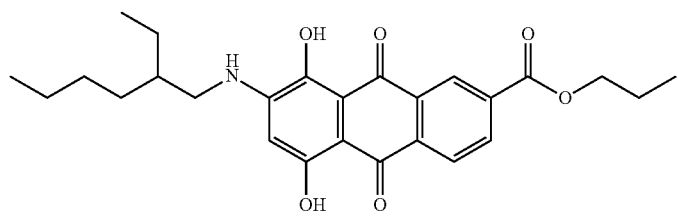

-continued
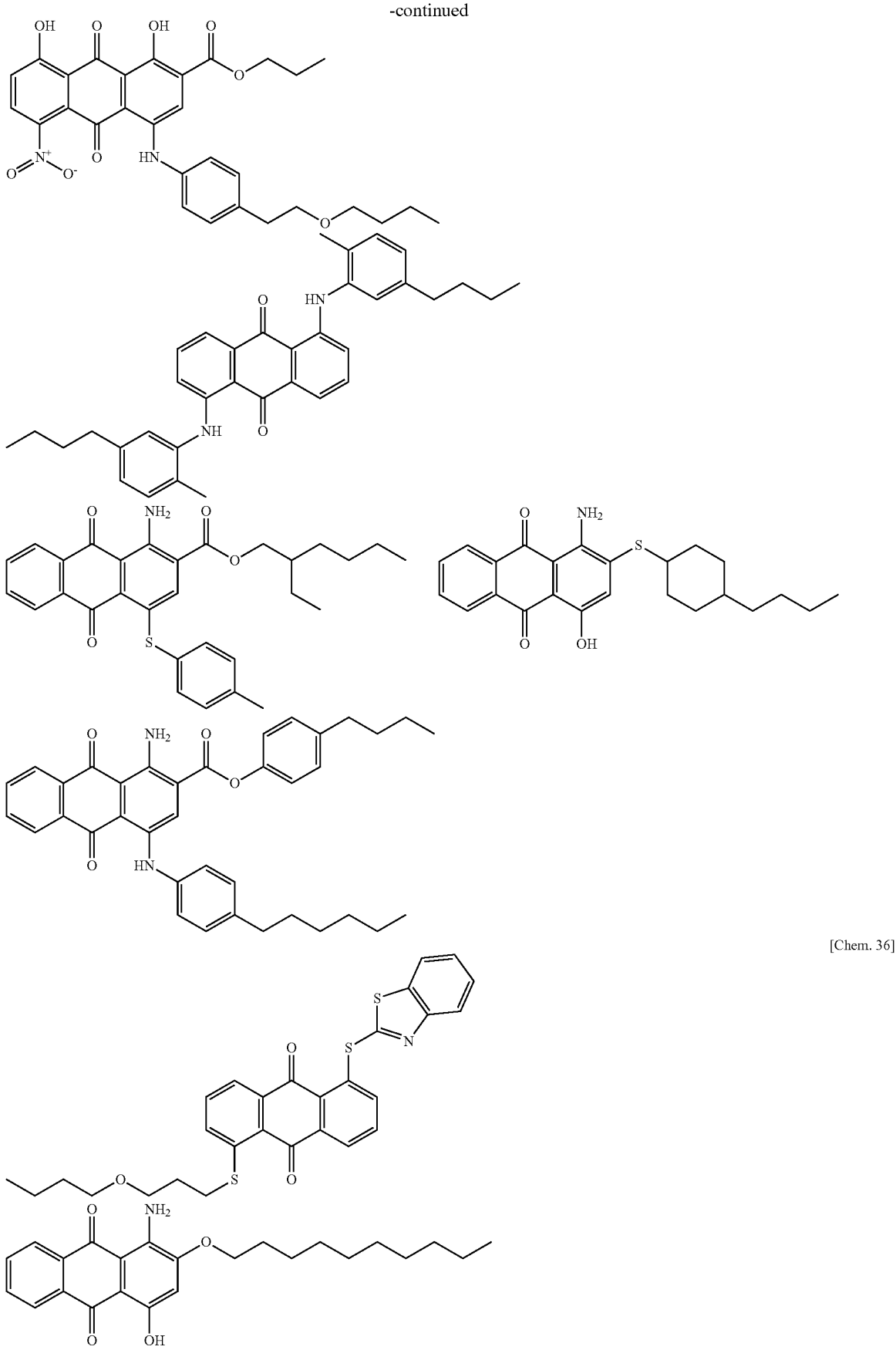
[Chem. 36]

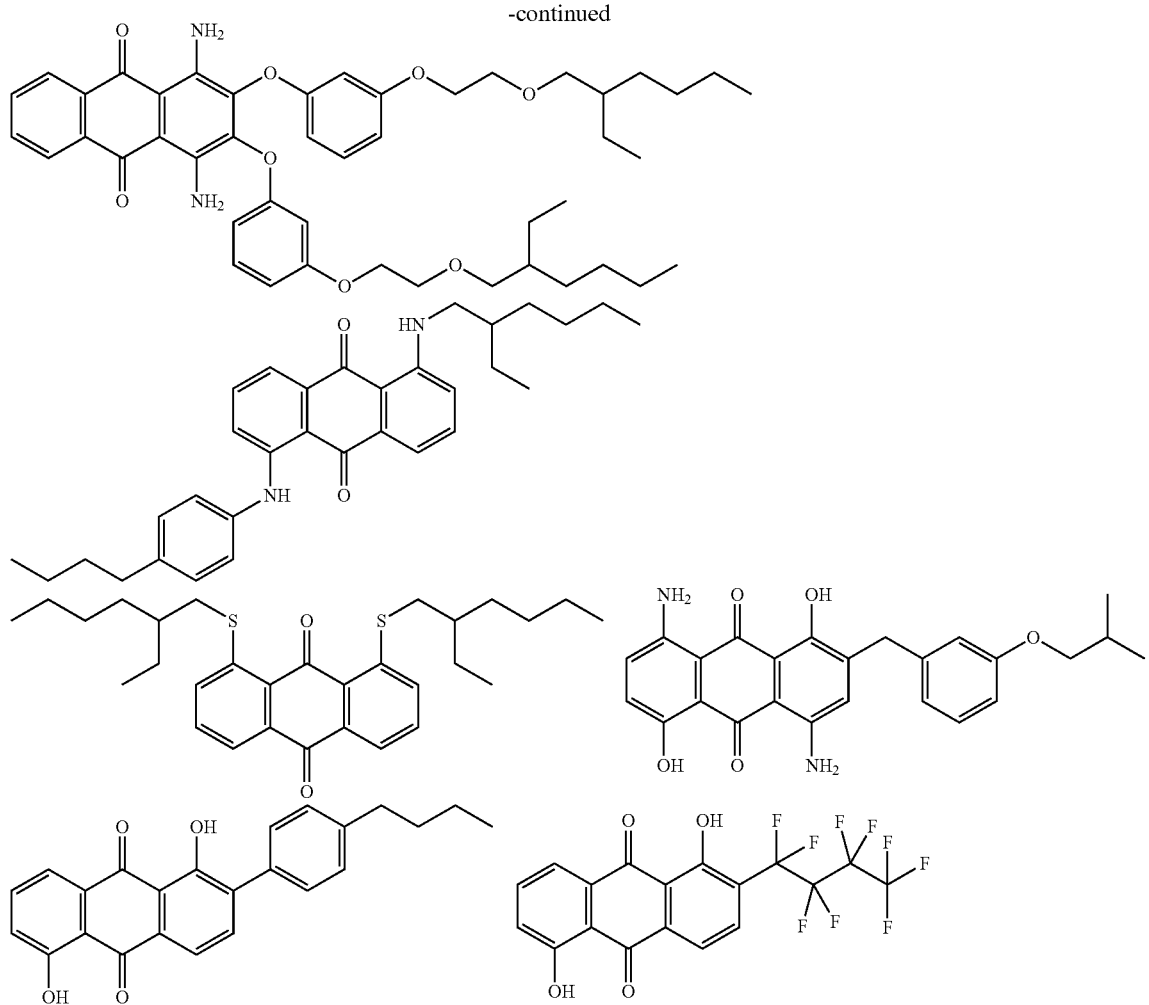

The anthraquinone compound represented by general formula (9) can be synthesized, for example, in accordance with the methods described in U.S. Pat. No. 5,558,808 and JP-T-11-506151.

The molecular weight of the anthraquinone compound represented by general formula (9), including the substituents in the case where the compound has substituents, is usually 2,000 or less, preferably 1,000 or less, and is usually 300 or higher, preferably 400 or higher, from the standpoint of gram extinction coefficient.

With respect to the concentration of the compounds represented by general formulae (1) to (9) in the ink in which the compounds are contained, the ink is prepared so as to have any desired concentration in accordance with the intended use thereof. In the case of use as compounds for electrowetting displays, the compounds are diluted, before use, with a solvent usually to a concentration of 0.2% by mass or higher according to the required value of EC. However, the concentration thereof is preferably 1% by mass or higher, more preferably 5% by mass or higher. The concentration thereof is usually preferably about 80% by mass or less.

In the case where the ink of the invention is to be used as a black ink, it is preferable that the ink should contain at least one of the compounds represented by general formulae (4) to (9), besides the compound represented by general formula (1). In cases when the ink contains these compounds, high light absorption can be attained in a wide wavelength range within the visible light region. In addition, even when used as a mixture thereof, these compounds are not reduced in solubility and show high solubility in the solvent. This ink is excellent in this respect.

Furthermore, the ink of the invention may contain any additives suitable for various applications according to need, so long as the effects of the invention are not lessened thereby.

The hue of an ink can be quantitatively evaluated in terms of the CIE chromaticity system $L^*a^*b^*$. $L^*$ indicates lightness; $L^*=0$ indicates black, and $L^*=100$ indicates a white diffusion color. Symbols $a^*$ and $b^*$ indicate hue, and saturation is expressed by $C^*$, which is determined from $a^*$ and $b^*$ using $C^*=\sqrt{(a^{*2}+b^{*2})}$. The closer the value of $C^*$ to 0, the more the color is achromatic.

In the case where the ink of the invention is used as a black ink, this ink shows a preferred hue because the values of both $L^*$ and $C^*$ are close to 0. In the case where the ink is examined using a cell having a measuring optical-path length of 0.01 mm, the value of $C^*$ thereof is preferably 2 or less, more preferably 1.5 or less. There is no lower limit thereon; the closer the value of $C^*$ to 0, the more the ink is preferred. Likewise, in the case where the ink is examined using a cell having a measuring optical-path length of 0.01 mm, the value of L* thereof is desirably 3 or less, preferably 2 or less. There is no lower limit thereon; the closer the value of L* to 0, the more the ink is preferred.

It is preferable that the ink of the invention should have a higher value of optical density (OD), and there is no particular upper limit thereon. When examined using the same measuring optical-path length, the value of OD of an ink depends on the concentration of each compound, absorption wavelengths of the compound, etc. For example, heightening the concentration of a compound results in an increase in the OD value of the ink. However, to heighten the concentration of a compound tends to increase the viscosity of the ink.

Meanwhile, since the ink of the invention contains one or more compounds which show absorption in a wavelength range where luminosity factor is high, low compound concentrations suffice for a desired OD. This ink has a high OD and a low viscosity, and is especially useful in the applications shown below.

(Applications)

The ink of the invention is suitable for use as inks for displays. With respect to displays, the ink of the invention is useful especially in displays which each have a display part including an ink and which are displays wherein voltage application to the display part is controlled to thereby display an image, or are displays wherein a change in the coloration state is caused by voltage application to thereby display an image, or are displays wherein electrophoretic particles or an aqueous medium is further used in the display part to display an image.

Examples of the display wherein a change in the coloration state is caused by voltage application to thereby display an image include one in which a colored or colorless ink or solvent is caused to undergo a movement, e.g., spreading or agglomeration, by voltage application to thereby cause a change in color and display an image. However, the display is not limited to this example.

Here, the electrophoretic particles are charged particles, and the particles may have a color. Multiple kinds of electrophoretic particles may be included in the display part. Meanwhile, the aqueous medium is a fluid which may have a color, and the display part may include multiple kinds of such aqueous media. Examples of the aqueous medium include water, non-charged liquids, liquids having an affinity for water, and liquids which are akin in surface tension to water, and specifically include alcohols and liquids which contain an inorganic salt, e.g., an alkali metal halide.

The azo compound and ink of the invention are especially useful as inks for use in displays operated in an electrowetting mode or displays operated in an electrophoresis mode.

It is also possible to provide satisfactory inks having excellent hues, e.g., a black ink, by using the azo compound of the invention in combination with other compound(s). For example, the black ink is useful as a member which functions as an optical shutter.

Although usable in any display devices having a display, the ink of the invention is especially useful in electronic paper.

Examples of display modes include an electrowetting mode and an electrophoresis mode. Examples of applications of such displays include various ones including computers, electronic paper, electronic signboards, and electronic inks, and there is a possibility that such displays can replace the existing liquid-crystal displays in most of the applications thereof. It is especially preferred to use the ink of the invention as an ink for electrowetting displays.

(Ink Containing at Least One of Each of the Following Compounds (I) to (IV))

Another ink of the invention is characterized by including a solvent which has a relative permittivity, measured at a frequency of 1 kHz and a temperature of 22° C., of 3 or less and a solubility in water at 25° C. of 20 mg/L or less and at least one of each of the following compounds (I) to (IV):

(I) compounds which as a decane solution thereof have an absorption maximum wavelength of 400 nm or larger and less than 500 nm, (II) compounds which as a decane solution thereof have an absorption maximum wavelength of 500 nm or larger and less than 570 nm, (III) compounds which as a decane solution thereof have an absorption maximum wavelength of 570 nm or larger and less than 640 nm, (IV) compounds which as a decane solution thereof have an absorption maximum wavelength of 640 nm to 700 nm.

Since this ink of the invention contains at least one of each of compounds (I) to (IV), the ink has high absorption in a wide wavelength range and is useful especially as a black ink. Furthermore, the concentration of a compound which is necessary for making the ink have a desired OD can be lowered. The ink hence has a high OD and a low viscosity, and is especially useful in the applications which will be described later.

Compounds (I) to (IV) are not particularly limited so long as these are compounds each having an absorption maximum wavelength in a specific range. However, from the standpoint of making the ink have a high OD and a low viscosity, it is preferable that the compounds should have excellent solubility in solvents, in particular, in solvents having a relative permittivity of 3 or less and a solubility in water at 25° C. of 20 mg/L or less.

Compounds (I) to (IV) have a solubility in 5° C. n-decane of preferably 1% by mass or higher, more preferably 3% by mass or higher, especially preferably 5% by mass or higher. The higher the solubility, the more the compounds are preferred. However, the solubility thereof is usually up to about 80% by mass. When the solubility thereof is not less than a specific value, there are cases where displaying on display devices such as displays is rendered possible.

In the case of use in electrowetting displays, it is desirable that compounds (I) to (IV) should be water-insoluble, in view of the principle of the displays. The term "water-insoluble" herein means that the solubility in water, under the conditions of 25° C. and 1 atm, is 0.1% by mass or less, preferably 0.01% by mass or less.

The molar extinction coefficient of each of compounds (I) to (IV) is preferably 10,000 (L·mol$^{-1}$·cm$^{-1}$) or higher, more preferably 40,000 (L·mol$^{-1}$·cm$^{-1}$) or higher, and is especially preferably 50,000 (L·mol$^{-1}$·cm$^{-1}$) or higher, from the standpoint of satisfying the performance of the display device.

The value of the product $\epsilon C$ of the molar extinction coefficient $\epsilon$ (L*mol$^{-1}$·cm$^{-1}$) at an absorption maximum wavelength of an n-decane solution of each of compounds (I) to (IV) and the saturation concentration C (mol·L$^{-1}$) at 5° C. of the solution is usually 500 cm$^{-1}$ or larger, preferably 1,000 cm$^{-1}$ or larger, especially preferably 2,000 cm$^{-1}$ or larger. Although there is no particular upper limit, the value of $\epsilon C$ is usually 60,000 cm$^{-1}$ or less.

With respect to the concentration of compounds (I) to (IV) in the ink of the invention, the ink is prepared so as to have any desired concentration in accordance with the intended use thereof. For example, in the case of use as a colorant for electrowetting displays, the compounds are diluted, before use, with a nonpolar solvent usually to a concentration of 1% by mass or higher, in accordance with a required concentration. However, the concentration thereof is preferably 3% by mass or higher, more preferably 5% by mass or higher. The concentration thereof is usually about 80% by mass or less.

In the ink of the invention which contains at least one of each of compounds (I) to (IV), there is no particular lower limit on the viscosity thereof at an ink temperature of 25° C. However, the viscosity at 25° C. thereof is usually preferably 0.1 mPa·s or higher. Meanwhile, the upper limit thereof is preferably 10,000 mPa·s or less, more preferably 1,000 mPa·s or less, especially preferably 100 mPa·s or less. In case where the ink has too high a viscosity, this ink may raise difficulties in operating the display device.

Although compounds (I) to (IV) are not particularly limited so long as these are compounds each having an absorption maximum wavelength in the specific range, examples of (I) include compounds represented by general formula (4), and examples of (II) include compounds represented by general formulae (5) and (6). Examples of (III) include compounds represented by general formulae (1), (5), (6), and (7), and examples of (IV) include compounds represented by general formula (7).

Azo compounds represented by the following general formulae (10) and (11) are novel compounds. These compounds have excellent solubility in solvents and have a high extinction coefficient.

[Chem. 37]

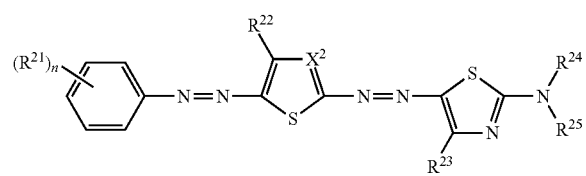

(10)

[In general formula (10), $R^{21}$ represents any substituent, $R^{22}$ and $R^{23}$ each independently represent a hydrogen atom or any substituent, $R^{24}$ and $R^{25}$ each independently represent an alkyl group which may have a substituent, $X^2$ represents a nitrogen atom or a methine group which may have a substituent, and n' represents an integer of 0-5.]

$R^{21}$ in general formula (10) has the same meaning as the $R^1$ contained in general formula (1), and the preferred range and the substituents which may be possessed are also the same. Likewise, $R^{22}$, $R^{23}$, $R^{24}$, $R^{25}$, and $X^2$ in general formula (10) and n' in general formula (10) have the same meanings as the $R^2$ in general formula (1), $R^5$ in general formula (2), $R^3$ in general formula (1), $R^4$ in general formula (1), X in general formula (1), and n in general formula (1), respectively, and the preferred ranges and the substituents which may be possessed are also the same.

[Chem. 38]

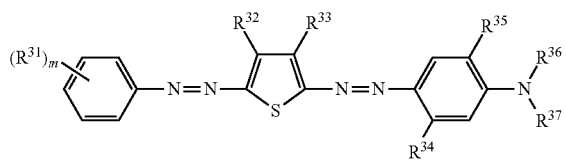

(11)

[In general formula (11), $R^{31}$ represents any substituent, $R^{32}$ represents a hydrogen atom or an alkyl group, $R^{33}$ represents a cyano group or an alkoxycarbonyl group, with the proviso that when $R^{32}$ is a hydrogen atom, $R^{33}$ represents an alkoxycarbonyl group, $R^{34}$ and $R^{35}$ each independently represent a hydrogen atom or any substituent, $R^{36}$ and $R^{37}$ each independently represent a branched alkyl group which has 4-20 carbon atoms and may have a substituent, and m represents an integer of 0-5.]

$R^{31}$ has the same meaning as the $R^1$ contained in general formula (1), and the substituents which may be possessed and the preferred range are also the same. Likewise, $R^{32}$, $R^{34}$, $R^{35}$, and m have the same meanings as the $R^2$ in general formula (1), $R^{46}$ in general formula (3), $R^7$ in general formula (3), and n in general formula (1), respectively, and the substituents which may be possessed and the preferred ranges are also the same.

Meanwhile, $R^{33}$ has the same meaning as the X contained in general formula (1) which is a carbon atom that may have a substituent which is either a cyano group or an alkoxycarbonyl group. The preferred range is also the same.

$R^{36}$ and $R^{37}$ each independently represent a branched alkyl group which has 4-20 carbon atoms and may have a substituent. Specifically, $R^{36}$ and $R^{37}$ each have the same meaning as the alkyl group represented by $R^1$ in general formula (1), the alkyl group being a branched alkyl group having 4-20 carbon atoms, and the substituents which may be possessed are also the same. The number of carbon atoms of each of $R^{35}$ and $R^{36}$ is more preferably 6-20, especially preferably 6-12. In cases when the number of carbon atoms thereof is in an adequate range, high solubility in solvents and a high gram extinction coefficient tend to be obtainable.

EXAMPLES

The invention will be explained below in more detail by reference to Examples and Comparative Examples, but the invention should not be construed as being limited to the following Examples in any way.

[Synthesis of Intermediates TH1 to TH4]

[Chem. 39]

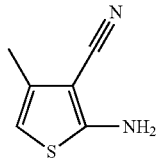

TH1

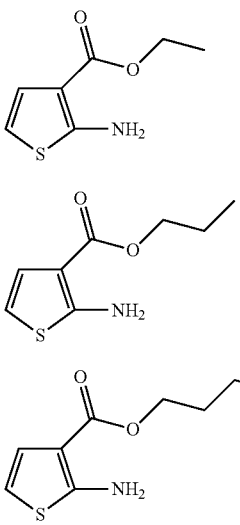

TH2

TH3

TH4

<Synthesis of Intermediate TH1>
2,5-Dimethyl-1,4-dithiane-2,5-diol (10 g; 55.5 mmol) and malononitrile (7.33 g; 111 mmol) were dissolved in methanol (100 mL). Triethylamine (15.4 mL; 111 mmol) was gradually added thereto, and the mixture was stirred at room temperature for 1 hour. This liquid reaction mixture was concentrated, washed with water, and then filtered to obtain intermediate TH1 (9.32 g; yield, quantitative; $^1$H-NMR (400 MHz, CDCl$_3$): 6.00 (s, 1H), 4.87 (br-s, 2H), 2.19 (s, 3H)) as a solid.

<Synthesis of Intermediate TH2>
1,4-Dithiane-2,5-diol (5.0 g; 32.8 mmol) and ethyl cyanoacetate (8.53 g; 75.4 mmol) were diluted with dimethylformamide (50 mL; 10 VR). Triethylamine (9.09 mL; 65.6 mmol) was dropped thereinto, and the mixture was allowed to react at room temperature for 30 minutes. Water (200 mL) was added to the liquid reaction mixture, and the resultant mixture was extracted with ethyl acetate (150 mL) twice. The organic layer was further washed with water (50 mL) three times. The organic layer was dried with magnesium sulfate and then filtered, and the filtrate obtained was concentrated to obtain intermediate TH2 (yield, quantitative) as a brown oil.

<Synthesis of Intermediate TH3>
Triethylamine (10.8 mL) was dropped into a mixture of propyl cyanoacetate (25.0 g; 0.19 mol), 1,4-dithiane-2,5-diol (16.45 g; 0.11 mol), and methanol (43 mL). In this operation, the reaction solution was kept at 30° C. or lower. After the dropping, the mixture was heated to 40° C. and stirred for 2 hours. This reaction solution was returned to room temperature and then concentrated. Ethyl acetate was added thereto, and the solid which had separated out was removed by filtration. The filtrate was concentrated to obtain intermediate TH3 (47.96 g) as a brown oil.

<Synthesis of Intermediate TH4>
Triethylamine (6.4 mL) was dropped into a mixture of butyl cyanoacetate (25.0 g; 0.18 mol), 1,4-dithiane-2,5-diol (14.81 g; 0.097 mol), and methanol (25 mL). In this operation, the reaction solution was kept at 30° C. or lower. After the dropping, the mixture was heated to 40° C. and stirred for 2 hours. This reaction solution was returned to room temperature and then concentrated. Ethyl acetate was added thereto, and the solid which had separated out was removed by filtration. The filtrate was concentrated to obtain intermediate TH4 (45.32 g; yield, quantitative).

[Synthesis of Intermediates MA1 to MA7]

[Chem. 40]

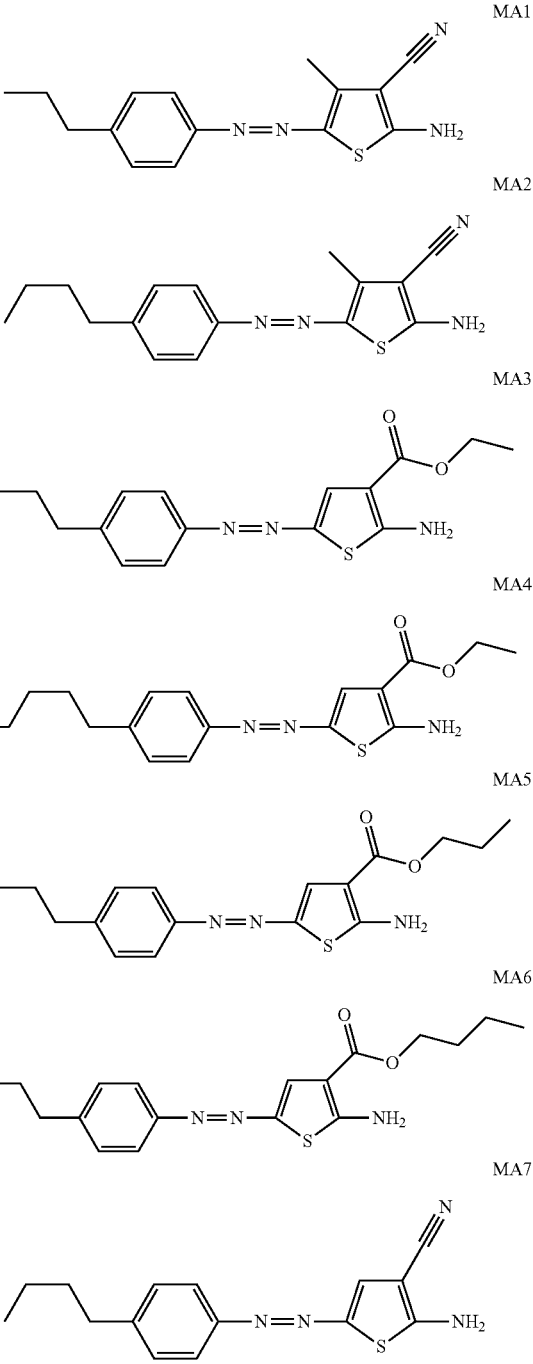

<Synthesis of Intermediate MA1>
4-Propylaniline (product of Tokyo Kasei: 5.87 g; 43.4 mmol) was diluted with water (60 mL). While this dilution was being cooled with ice, concentrated hydrochloric acid (12.0 mL; 130 mmol) was added thereto and sodium nitrite (3.14 g; 61.3 mmol) was further added gradually thereto. The resultant mixture was stirred for further 30 minutes with cooling with ice to obtain a diazotization solution. Intermediate TH1 (6.00 g; 43.4 mmol) was diluted with methanol (120 mL) in another flask, and the diazotization solution was gradually dropped thereinto. This mixture was stirred for 10 minutes and then heated to room temperature. The mixture was filtered, and the solid obtained was washed with a small amount of methanol to obtain intermediate MA1 (12.4 g; yield, quantitative).

<Synthesis of Intermediate MA2>

4-Butylaniline (product of Tokyo Kasei: 8.72 g; 58.4 mmol) was diluted with water (90 mL). While this dilution was being cooled with ice, concentrated hydrochloric acid (15.9 mL; 175 mmol) was added thereto and sodium nitrite (4.23 g; 61.3 mmol) was further added gradually thereto. The resultant mixture was stirred for further 30 minutes with cooling with ice to obtain a diazotization solution. Intermediate TH1 (7.50 g; 54.2 mmol) was diluted with methanol (250 mL) in another flask, and the diazotization solution was gradually dropped thereinto. This mixture was stirred for 10 minutes and then heated to room temperature. The mixture was filtered, and the solid obtained was washed with a small amount of methanol to obtain intermediate MA2 (19.0 g; yield, quantitative).

<Synthesis of Intermediate MA3>

4-Butylaniline (product of Tokyo Kasei: 8.72 g; 58.4 mmol) was diluted with water (90 mL). While this dilution was being cooled with ice, concentrated hydrochloric acid (15.9 mL; 175 mmol) was added thereto and sodium nitrite (4.23 g; 61.3 mmol) was further added gradually thereto. The resultant mixture was stirred for further 30 minutes with cooling with ice to obtain a diazotization solution. Intermediate TH2 (10.0 g; 58.4 mmol) was diluted with methanol (90 mL) in another flask, and the diazotization solution was gradually dropped thereinto. This mixture was stirred for 10 minutes and then heated to room temperature. The mixture was filtered, and the solid obtained was washed with methanol (200 mL) to obtain intermediate MA3 (12.1 g; yield, 62%).

<Synthesis of Intermediate MA4>

4-Pentylaniline (product of Tokyo Kasei: 2.33 g; 14.3 mmol) was diluted with water (25 mL; 10 VR), and 35% hydrochloric acid (3.9 mL; 42.9 mmol; 3.0 MR) was added thereto. Sodium nitrite (1.03 g; 15.0 mmol) was added thereto with cooling with ice to obtain a diazotization solution. Intermediate TH2 (4.5 g; 13.0 mmol) and methanol (45 mL; 10 VR) were introduced into another flask. While this flask was being cooled with an ice bath, the diazotization solution was gradually dropped thereinto. In the course of the dropping, methanol (50 mL) was added. The liquid reaction mixture was heated to room temperature, and the solid which had separated out was taken out by filtration. The solid obtained was suspended in and washed with methanol (100 mL), and the suspension was filtered to obtain intermediate MA4 (4.84 g; yield, quantitative) as a yellow solid.

<Synthesis of Intermediate MA5>

A mixture of 4-butylaniline (10 mL; 62.9 mmol), desalted water (78 mL), and 35% hydrochloric acid (19.4 mL) was cooled to 0° C. or below, and an aqueous solution (21 mL) of sodium nitrite (4.563 g; 66.13 mol) was dropped thereinto. After the dropping, the mixture was stirred for 30 minutes while keeping the temperature thereof at 0° C. or below. Thus, a diazotization solution was obtained. A mixture of TH3 (11.668 g; 0.153 mol), methanol (520 mL), and sulfamic acid (0.611 g; 6.29 mmol) was cooled to 0° C. or below, and the diazotization solution was dropped thereinto. After the dropping, the mixture was stirred for 30 minutes while keeping the temperature thereof at 0° C. or below. The reaction solution was returned to room temperature, and the sediment which had separated out was taken out by filtration and rinsed by pouring a water/methanol=1/1 solution (300 mL) thereon. Thus, intermediate MA5 (13.81 g; yield, 63%) was obtained.

<Synthesis of Intermediate MA6>

A mixture of 4-butylaniline (10 mL; 62.9 mmol), desalted water (78 mL), and 35% hydrochloric acid (19.4 mL) was cooled to 0° C. or below, and an aqueous solution (21 mL) of sodium nitrite (4.563 g; 66.13 mol) was dropped thereinto. After the dropping, the mixture was stirred for 30 minutes while keeping the temperature thereof at 0° C. or below. Thus, a diazotization solution was obtained. A mixture of TH4 (12.55 g; 62.9 mmol), methanol (188 mL), and sulfamic acid (0.611 g; 6.29 mmol) was cooled to 0° C. or below, and the diazotization solution was dropped thereinto.

In the course of the dropping, a solid separated out to render the stirring difficult, and methanol (260 mL) was hence added. After the dropping of the diazotization solution, the mixture was stirred for 30 minutes while keeping the temperature thereof at 0° C. or below. The reaction solution was returned to room temperature, and the sediment which had separated out was taken out by filtration and rinsed by pouring a water/methanol=1/1 solution (300 mL) thereon. Thus, intermediate MA6 (12.87 g; yield, 57%) was obtained.

<Synthesis of Intermediate MA7>

A mixture of 8.02 g (54 mmol) of 4-n-butylaniline and 80 mL of 7% aqueous hydrochloric acid solution was stirred and cooled with ice, and an aqueous solution obtained by dissolving 3.76 g (55 mmol) of sodium nitrite in 25 mL of water was thereafter dropped thereinto. This mixture was stirred to obtain a diazotization solution. Into another vessel were introduced 6.68 g (54 mmol) of 2-amino-3-cyanothiophene and 100 mL of methanol. On an ice bath, the diazotization solution was dropped into the mixture to cause coupling. The sediment yielded was taken out by filtration and dried to obtain intermediate MA7 (14 g; yield, 92%).

[Synthesis of Intermediates CP1 to CP7]

[Chem. 41]

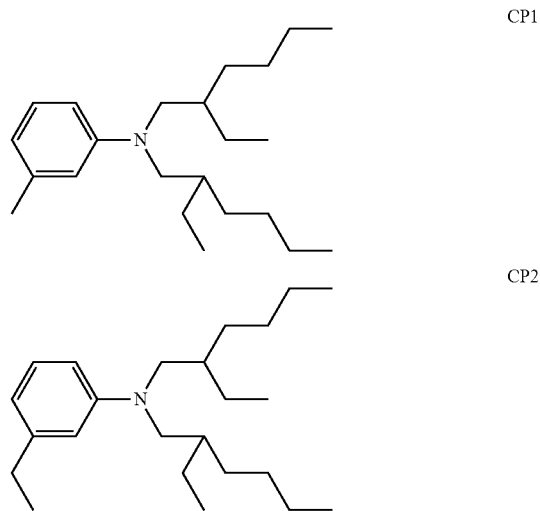

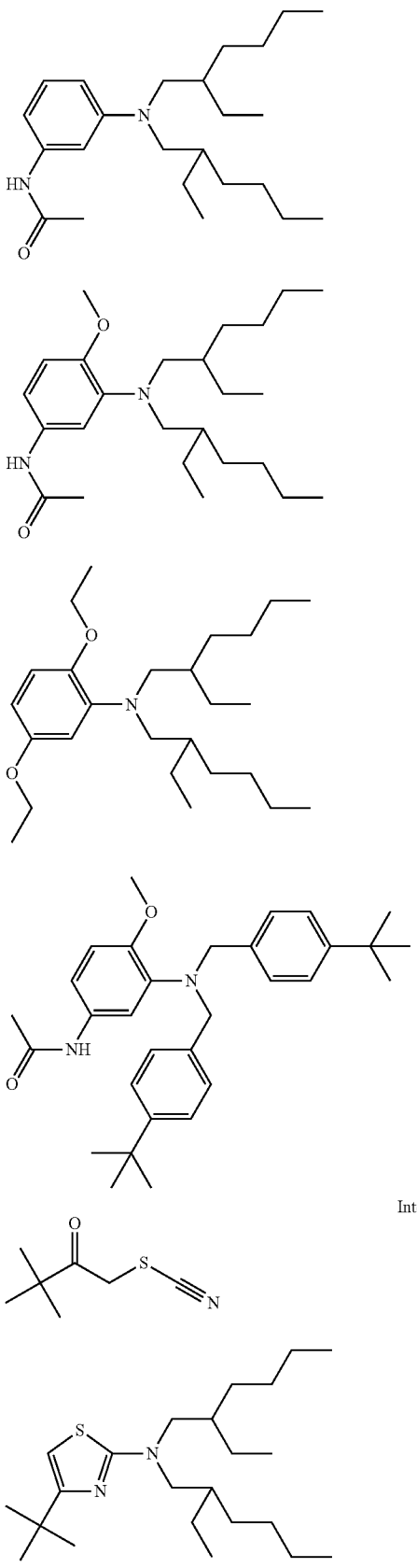

<Synthesis of Intermediate CP1>

A mixture of m-toluidine (51.1 g; 477 mmol), 1-bromo-2-ethylhexane (357.3 g; 1.86 mol), and potassium carbonate (221.5 g; 1.6 mol) was stirred at 140° C. for 17 hours. This mixture was allowed to cool and then filtered. The organic layer obtained was concentrated and then purified by silica gel column chromatography to obtain intermediate CP1 (52 g: yield, 33%).

<Synthesis of Intermediate CP2>

A mixture of 3-ethylaniline (10.0 g; 83 mmol), N,N-dimethylformamide (50 mL), 1-bromo-2-ethylhexane (47.8 g; 248 mmol), and potassium carbonate (45.6 g; 330 mmol) was stirred at 110° C. for 24 hours. The mixture was allowed to cool and then filtered. Water was added to the filtrate, and the resultant mixture was extracted with toluene. The organic layer obtained was concentrated and then purified by silica gel column chromatography to obtain CP2 (6.3 g; yield 22%).

<Synthesis of Intermediate CP3>

A mixture of m-aminoacetanilide (13.0 g; 87 mmol), N,N-dimethylformamide (60 mL), 1-bromo-2-ethylhexane (50.4 g; 261 mmol), and potassium carbonate (49.5 g; 358 mmol) was stirred at 140° C. for 14 hours. The mixture was allowed to cool and then filtered. Water was added to the filtrate, and the resultant mixture was extracted with toluene. The organic layer obtained was concentrated and then purified by silica gel column chromatography to obtain CP3 (17.4 g; yield 54%).

<Synthesis of Intermediate CP4>

A mixture of 3'-amino-4'-methoxyacetanilide (25.0 g; 139 mmol), N,N-dimethylformamide (125 mL), 1-bromo-2-ethylhexane (80.4 g; 416 mmol), and potassium carbonate (76.7 g; 554 mmol) was stirred at 140° C. for 14 hours. The mixture was allowed to cool and then filtered. Water was added to the filtrate, and the resultant mixture was extracted with toluene. The organic layer obtained was concentrated and then purified by silica gel column chromatography to obtain intermediate CP4 (9.82 g; yield 18%).

<Synthesis of Intermediate CP5>

Into a flask were introduced 2,5-diethoxyanilne (product of Tokyo Kasei: 50 g; 276 mmol), 2-ethylhexyl bromide (286 mL), potassium iodide (4.58 g), and potassium carbonate (153 g). The contents were heated and stirred for 26 hours in total at an internal temperature of about 125° C. This liquid reaction mixture was cooled to room temperature and filtered. Water (400 mL) was added to the filtrate obtained, and the resultant mixture was extracted with hexane (300 mL). The hexane layer was further washed with water (400 mL) twice and dried with magnesium sulfate, and the solvent was thereafter distilled off. The crude product obtained was purified by silica gel column chromatography to obtain intermediate CP5 (23.6 g; yield, 22%) as oily matter.

<Synthesis of Intermediate CP6>

A mixture of 3'-amino-4'-methoxyacetanilide (7.51 g; 41.7 mmol), 4-tert-butylbenzyl bromide (28.4 g; 125 mmol), potassium carbonate (11.5 g; 83.4 mmol), and N,N-dimethylformamide (25 mL) was stirred for 1.5 hours at an internal temperature of 75° C. This mixture was cooled to room temperature, and water was added thereto. The resultant mixture was extracted with a mixed solvent composed of toluene and ethyl acetate. The extract was dried with anhydrous sodium sulfate and concentrated under vacuum. The solid was washed with hexane to obtain intermediate CP6 (17.7 g; yield, 90%).

<Synthesis of Intermediate CP7>

A mixture of methanol (36 mL) and sodium thiocyanate (15.5 g; 191 mmol) was heated to 60° C., and 1-chloropinacolone (25 mL; 191 mmol) was dropped thereinto over 15 minutes. This mixture was heated at 60° C. for 2.5 hours, allowed to cool to room temperature, and then cooled to 10° C. or below with an ice bath. Water (32 mL) was dropped thereinto, and the resultant mixture was stirred at 5° C. for 1 hour. The resultant crystals were taken out by filtration and air-dried to obtain intermediate 1 (amount yielded, 27 g; yield, 90%).

A mixture of the intermediate 1 (13 g; 83 mmol), toluene (65 mL), and acetic acid (2.5 g; 41 mmol) was heated to 80° C., and di(2-ethylhexyl)amine (20 g; 83 mmol) was dropped thereinto over 10 minutes. This mixture was heated at 80° C. for 4 hours and then allowed to cool to room temperature. Thereafter, water was added to the organic layer, and the resultant mixture was subjected to liquid separation. Furthermore, the organic layer was washed with water three times and with saturated aqueous sodium chloride solution once. This organic layer was dried with anhydrous sodium sulfate, and the solvent was distilled off. The residue was purified by column chromatography to obtain intermediate CP7 as a colorless viscous liquid (amount yielded, 21.77 g; yield, 69.1%).

Example 1

Synthesis of Compound 1

Intermediate MA2 (7.50 g; 25.1 mmol) was diluted with acetic acid/propionic acid=17/8 (V/V) (375 mL), and this dilution was cooled to −5° C. with a freezing mixture. While holding the dilution at 0° C. or below, 40% nitrosylsulfuric acid (8.77 g; 1.1 eq.) was gradually dropped thereinto to prepare a diazotization solution. Intermediate CP3 (9.39 g; 25.1 mmol), THF (275 mL), and sodium acetate (13.2 g) were introduced into another flask and cooled to −5° C. While holding the contents at 0° C. or below, the diazotization solution was gradually dropped thereinto.

The liquid reaction mixture was heated to room temperature, and water was added thereto. Thereafter, this mixture was extracted with hexane, and the organic layer was washed twice with 10% aqueous sodium hydroxide solution (200 mL). The organic layer was dried with magnesium sulfate, and the solvent was distilled off. The resultant residue was purified by silica gel column chromatography, and methanol was added thereto. This mixture was cooled, and the solid obtained was taken out by filtration to obtain compound 1 (yield, 14%).

Example 2

Synthesis of Compound 2

Intermediate MA2 (2.50 g; 8.38 mmol) was diluted with acetic acid/propionic acid=17/8 (V/V) (125 mL), and the dilution was cooled to −5° C. or below with a freezing mixture. Thereinto was gradually dropped 40% nitrosylsulfuric acid (2.93 g; 9.05 mmol), thereby preparing a diazotization solution. Intermediate CP1 (2.78 g; 8.38 mmol), THF (125 mL), and sodium acetate (4.5 g) were introduced into another flask and cooled to −5° C. Thereinto was gradually dropped the diazotization solution prepared as described above.

The liquid reaction mixture was heated to room temperature, and water (200 mL) was added thereto. Thereafter, this mixture was extracted with hexane (300 mL), and the organic layer was washed twice with 10% aqueous NaOH solution (100 mL). The organic layer was dried with magnesium sulfate and concentrated under vacuum. The concentrate was purified by silica gel column chromatography, and the solid was washed with methanol to obtain compound 2 (1.40 g; yield, 26%).

Example 3

Synthesis of Compound 3

Intermediate MA1 (3.00 g; 10.5 mmol) was diluted with acetic acid/propionic acid=17/8 (V/V) (180 mL), and the dilution was cooled to −5° C. or below with a freezing mixture. Thereinto was gradually dropped 40% nitrosylsulfuric acid (3.67 g; 9.05 mmol), thereby preparing a diazotization solution. Intermediate CP3 (3.95 g; 10.5 mmol), THF (180 mL), and sodium acetate (5.5 g) were introduced into another flask and cooled to −5° C. Thereinto was gradually dropped the diazotization solution prepared as described above.

The liquid reaction mixture was heated to room temperature, and water (200 mL) was added thereto. Thereafter, this mixture was extracted with hexane (300 mL), and the organic layer was washed twice with 10% aqueous sodium hydroxide solution (100 mL). The organic layer was dried with magnesium sulfate and concentrated under vacuum. The concentrate was purified by silica gel column chromatography, and the solid was washed with methanol (50 mL) to obtain compound 3 (770 mg; yield, 11%).

Example 4

Synthesis of Compound 4

Intermediate MA2 (3.58 g; 10.5 mmol) was diluted with acetic acid/propionic acid=17/8 (V/V) (215 mL), and the dilution was cooled to −5° C. or below with a freezing mixture. Thereinto was gradually dropped 40% nitrosylsulfuric acid (4.19 g; 13.2 mmol), thereby preparing a diazotization solution. Intermediate CP5 (4.87 g; 12.0 mmol), THF (215 mL), and sodium acetate (6.5 g) were introduced into another flask and cooled to −5° C. Thereinto was gradually dropped the diazotization solution prepared as described above.

The liquid reaction mixture was heated to room temperature, and water (100 mL) was added thereto. Thereafter, this mixture was extracted twice with n-hexane (200 mL), and the organic layer was washed twice with 10% aqueous NaOH solution (100 mL). The organic layer was dried with magnesium sulfate and concentrated under vacuum. The concentrate was purified by silica gel column chromatography, and methanol was added thereto. This mixture was cooled, and the solid obtained was taken out by filtration to obtain compound 4 (630 mg; yield, 8%).

Example 5

Synthesis of Compound 5

Intermediate MA4 (2.40 g; 6.95 mmol) was diluted with acetic acid/propionic acid=17/8 (V/V) (144 mL), and the dilution was cooled to −5° C. or below with a freezing mixture. Thereinto was gradually dropped 40% nitrosylsulfuric acid (2.65 g; 8.34 mmol), thereby preparing a diazotization solution. Intermediate CP2 (2.30 g; 6.95 mmol), THF (150 mL), and sodium acetate (5.0 g) were introduced into another flask and cooled to −5° C. Thereinto was gradually dropped the diazotization solution prepared as described above.

The liquid reaction mixture was heated to room temperature, and water (400 mL) was added thereto. Thereafter, this mixture was extracted twice with n-hexane (200 mL), and the organic layer was washed twice with 1-N NaOH (200 mL). The organic layer was dried with magnesium sulfate and concentrated under vacuum. The concentrate was purified by silica gel column chromatography, and methanol was added thereto. This mixture was cooled, and the solid obtained was taken out by filtration to obtain compound 5 (190 mg; yield, 4%).

Example 6

Synthesis of Compound 6

Intermediate MA3 (2.50 g; 7.54 mmol) was diluted with acetic acid/propionic acid=17/8 (V/V) (250 mL), and the dilution was cooled to −5° C. or below with a freezing mixture. Thereinto was gradually dropped 40% nitrosylsulfuric acid (2.87 g; 9.05 mmol), thereby preparing a diazotization solution. Intermediate CP1 (2.50 g; 7.54 mmol), THF (250 mL), and sodium acetate (5.0 g) were introduced into another flask and cooled to −5° C. Thereinto was gradually dropped the diazotization solution prepared as described above.

The liquid reaction mixture was heated to room temperature, and water (300 mL) was added thereto. Thereafter, this mixture was extracted twice with hexane (400 mL), and the organic layer was washed twice with 10% aqueous NaOH solution (100 mL). The organic layer was dried with magnesium sulfate and concentrated under vacuum. The concentrate was purified by silica gel column chromatography, and methanol was added thereto. This mixture was cooled, and the solid obtained was taken out by filtration to obtain compound 6 (150 mg; LC area, 98.8%; yield, 3%).

Example 7

Synthesis of Compound 7

A mixture of intermediate MA5 (3.00 g; 8.68 mmol), 85% phosphoric acid (38 mL), acetic acid (25 mL), and propionic acid (13 mL) was cooled to 0° C. or below, and 40% nitrosylsulfuric acid (2.89 g; 9.11 mmol) was dropped thereinto. After the dropping, the mixture was stirred for 30 minutes while holding the mixture at 0° C. or below, thereby obtaining a diazotization solution. A mixture of intermediate CP1 (2.879 g; 8.68 mmol), tetrahydrofuran (18 mL), methanol (2 mL), desalted water (3 mL), and urea (52 mg; 0.868 mmol) was cooled to 0° C. or below, and the diazotization solution was dropped thereinto.

During this operation, the pH was kept at 2.8-3.6 by suitably adding a saturated aqueous solution of sodium acetate. After the diazotization solution had been dropped, the resultant mixture was stirred for 30 minutes while holding the mixture at 0° C. or below. This reaction solution was returned to room temperature, and the aqueous layer was extracted with hexane. The organic layer was dried with anhydrous sodium sulfate and filtered, and the resultant filtrate was concentrated. The crude product obtained was purified by silica gel column chromatography and solidified by cooling in a freezer. Thus, compound 7 was obtained as a powder.

Example 8

Synthesis of Compound 8

A mixture of intermediate MA6 (3.00 g; 8.34 mmol), 85% phosphoric acid (38 mL), acetic acid (25 mL), and propionic acid (13 mL) was cooled to 0° C. or below, and 40% nitrosylsulfuric acid (2.78 g; 8.8 mmol) was dropped thereinto. After the dropping, the mixture was stirred for 30 minutes while holding the mixture at 0° C. or below, thereby obtaining a diazotization solution. A mixture of intermediate CP1 (2.767 g; 8.34 mmol), tetrahydrofuran (18 mL), methanol (2 mL), desalted water (3 mL), and urea (50 mg; 0.834 mmol) was cooled to 0° C. or below, and the diazotization solution was dropped thereinto.

During this operation, the pH was kept at 2.8-3.6 by suitably adding a saturated aqueous solution of sodium acetate. After the diazotization solution had been dropped, the resultant mixture was stirred for 30 minutes while holding the mixture at 0° C. or below. This reaction solution was returned to room temperature, and the aqueous layer was extracted with hexane. The organic layer was dried with anhydrous sodium sulfate, concentrated under vacuum, and purified by silica gel column chromatography. Thereafter, the purified product was solidified by cooling in a freezer, thereby obtaining compound 8 as a powder.

Example 9

Synthesis of Compound 9

Intermediate MA3 (3.31 g; 10 mmol), phosphoric acid (30 mL), acetic acid (24 mL), and propionic acid (6 mL) were cooled with an ice-acetone bath, and 40% nitrosylsulfuric acid (3.49 g; 11 mmol) was added thereto. This mixture was stirred for 20 minutes to obtain a diazotization solution. Intermediate CP4 (4.05 g; 10 mmol), amidosulfuric acid (0.29 g; 3 mmol), tetrahydrofuran (50 mL), and water (100 mL) were introduced into another vessel. While cooling this mixture with an ice bath, the diazotization solution was added thereto.

During this operation, the internal temperature was kept at 7° C. or below, and the pH was kept at 2-3 by dropping an aqueous sodium acetate solution. After the dropwise addition, the mixture was stirred for further 3 hours with cooling, and then extracted with toluene. The toluene layer was washed with water and concentrated under vacuum. The concentrate was purified by silica gel column chromatography and washed with methanol. Thus, compound 9 (2.2 g; yield, 29%) was obtained as a black powder.

Example 10

Synthesis of Compound 10

A mixture of intermediate MA7 (2.50 g; 8.79 mmol), 85% phosphoric acid (31 mL), acetic acid (20 mL), and propionic acid (10 mL) was cooled to −5° C., and 40% nitrosylsulfuric acid (2.9 g; 9.2 mmol) was dropped thereinto.

After the dropping, the mixture was stirred for 15 minutes while holding the mixture at −5° C. or below, thereby obtaining a diazotization solution. A mixture of intermediate CP7 (3.34 g; 8.79 mmol), tetrahydrofuran (22 mL), methanol (2 mL), desalted water (3 mL), and urea (0.052 g; 0.87 mmol) was cooled to −5° C. or below in another vessel, and the diazotization solution was dropped thereinto. During this operation, the pH was kept at 2.8-3.2 by adding an aqueous sodium acetate solution (110 mL in total).

After the diazotization solution had been dropped, the resultant mixture was stirred for 30 minutes while holding the mixture at −5° C. or below. This reaction solution was returned to room temperature, and the aqueous layer was extracted with hexane. The organic layer was dried with anhydrous sodium sulfate, concentrated under vacuum, and purified by silica gel column chromatography. Methanol was added thereto, and the mixture was cooled. The resultant solid was taken out by filtration to obtain compound 10 (1.97 g; yield, 33%).

<Synthesis of Compound 11>

A mixture of intermediate MA8 (5.0 g; 16.7 mmol), 85% phosphoric acid (63 mL), acetic acid (24 mL), and propionic acid (21 mL) was cooled to −5° C. or below, and 40% nitrosylsulfuric acid (5.85 g; 18.4 mmol) was dropped thereinto. After completion of the dropping, the mixture was stirred at −5° C. or below for 30 minutes to obtain a diazotization solution. A mixture of CP7 (6.37 g; 16.7 mmol), tetrahydrofuran (41 mL), methanol (6 mL), desalted water (6 mL), and urea (0.100 g; 1.67 mmol) was introduced into another vessel, and the diazotization solution was dropped thereinto while keeping the internal temperature at −5° C. or below.

During this operation, the pH was kept at 2.8-3.2 by adding an aqueous sodium acetate solution. After completion of the dropping, the resultant mixture was stirred at −5° C. for 30 minutes and then returned to room temperature. Thereafter, water was added thereto, and this mixture was extracted with hexane. The hexane layer was dried with anhydrous sodium sulfate, concentrated under vacuum, and purified by silica gel column chromatography. Methanol was added thereto, and the resultant solid was taken out by filtration to obtain compound 11.

[Chem. 42]

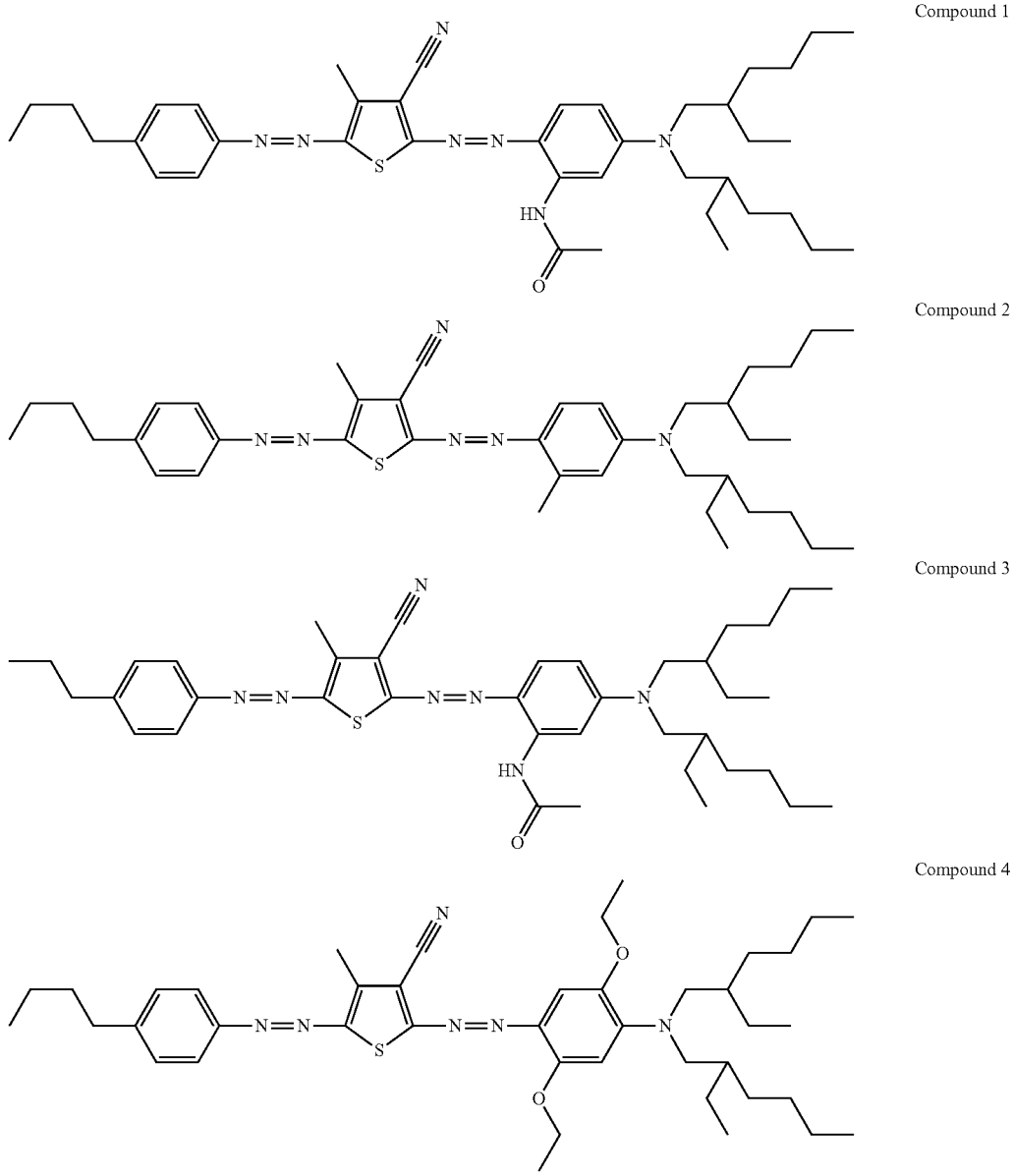

-continued
Compound 5
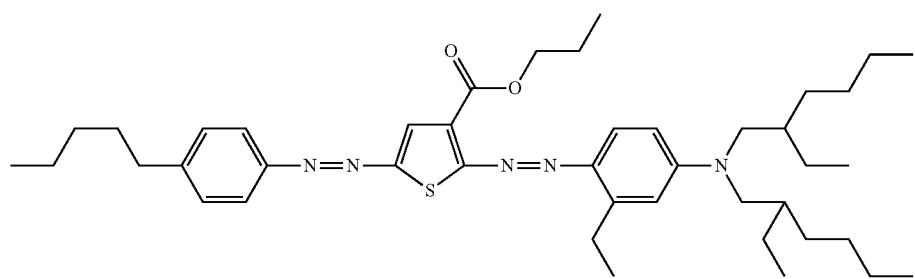
Compound 6
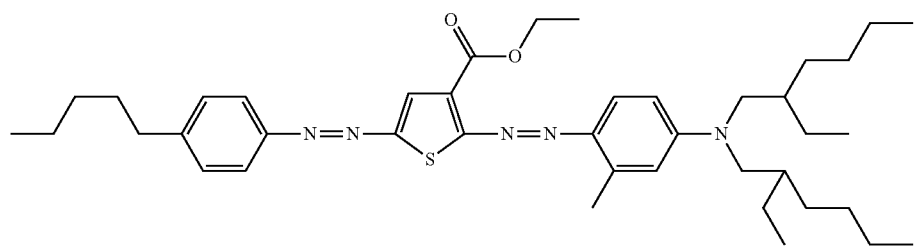
Compound 7
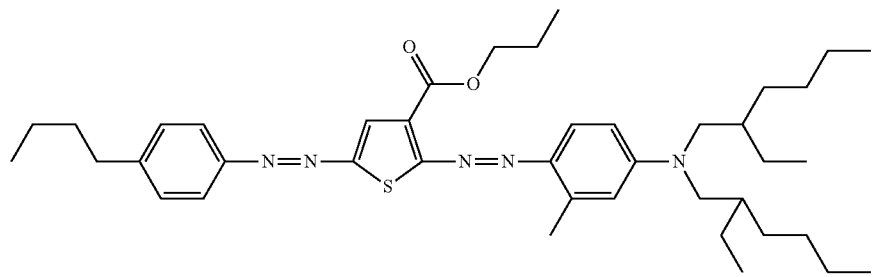
Compound 8
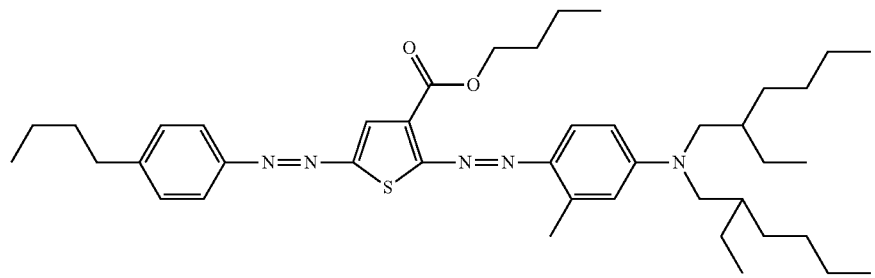
Compound 9
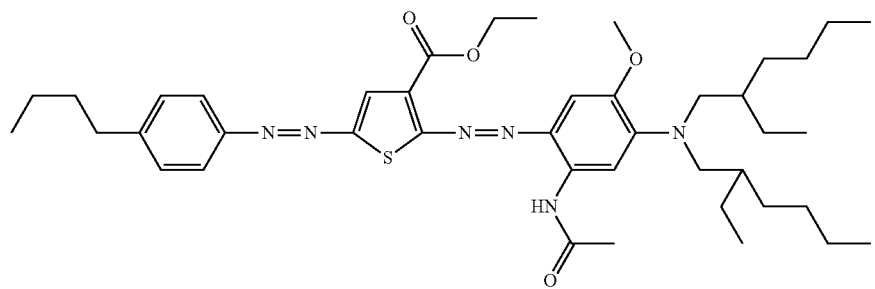
Compound 10
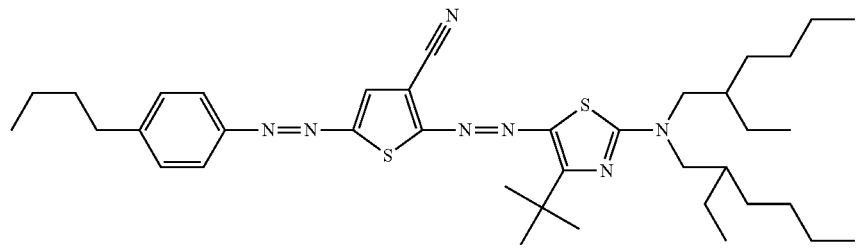

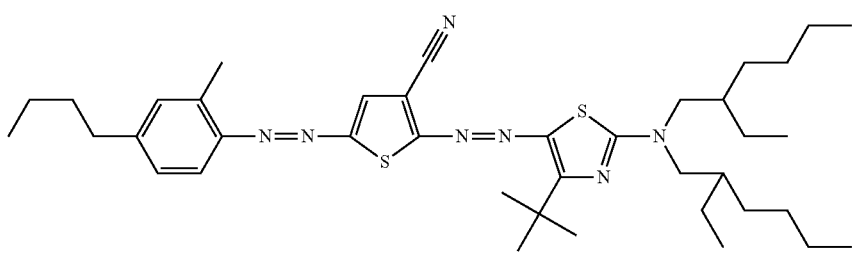

Compound 11

Comparative Example 1

<Synthesis of Intermediate TD>

A mixture of 2-amino-5-mercapto-1,3,4-thiadiazole (12.9 g; 96.8 mmol), 1-bromohexane (16.8 g; 102 mmol), ethanol (100 mL), and potassium hydroxide (8.15 g; 145 mmol) was heated with refluxing for 4 hours and then poured into ice water. The sediment was taken out by filtration and washed with methanol/water (1/1 by volume) to obtain intermediate TD (12.3 g; yield, 58%).

<Synthesis of Comparative Compound 1>

A mixture of 44% nitrosylsulfuric acid (2.52 g; 10 mmol), acetic acid (30 mL), and propionic acid (10 mL) was prepared with cooling with an ice bath. Intermediate TD (2.17 g; 10 mmol) was added thereto, and this mixture was stirred for 1 hour with cooling with an ice bath to obtain a diazotization solution. Intermediate CP6 (4.73 g; 10 mmol), sodium acetate (16.4 g; 100 mmol), and tetrahydrofuran (60 mL) were introduced into another vessel, and the diazotization solution was dropped thereinto with cooling with an ice bath. The resultant mixture was stirred at room temperature. Thereafter, water was added thereto, and this mixture was extracted with toluene. The toluene layer was washed with water and concentrated under vacuum. The concentrate was purified by silica gel column chromatography to obtain comparative compound 1 (1.79 g; yield, 26%).

as a solvent. The solution color, absorption maximum wavelength ($\lambda_{max}$), solubility C in 5° C. n-decane, molar extinction coefficient ε, and εC of each ink are summarized in Table 4.

<Method of Determining Relative Permittivity of Solvent>

Precision LCR Meter 4284A, manufactured by Agilent Technologies, Inc., was used to make a measurement by the impedance meter method. The solvent and the ink were each sandwiched between flat glass substrates which each had an ITO electrode and which had been arranged opposite and in parallel so as to result in an electrode spacing of 30 Thereafter, at 22° C., the equivalent parallel capacitance was measured under the conditions of a frequency of 1 kHz and application of a test signal voltage of 0.1 V. The relative permittivity was determined through a calculation using the following equation and evaluated.

Relative permittivity=(equivalent parallel capacitance)×(electrode spacing)/(electrode area)/(permittivity of vacuum ($\epsilon_0$))

<Method of determining Solubility of Solvent in Water>

Into a 110-mL vial were introduced 30 g of pure water and 8 g of the solvent. This vial was shaken for 4 hours at a

[Chem. 43]

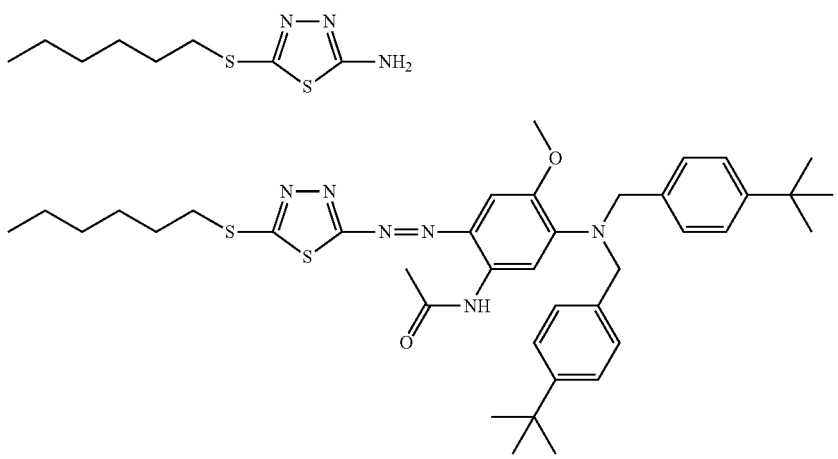

Intermediate TD

Comparative compound 1

[Production of Inks of the Compounds]

With respect to each of compounds 1 to 11 and comparative compound 1, an ink was prepared using n-decane (relative permittivity, 2.0; solubility in water, 1 mg/L or less)

frequency of 200 times per minute in a 25° C. thermostatic chamber. The liquid which had undergone the shaking was centrifuged (6,000×g; for 5 minutes), and the aqueous layer was sampled. The concentration of the solvent dissolved therein was determined by gas chromatography.

<Method of determining Absorption Maximum Wavelength $\lambda_{max}$ and Molar Extinction Coefficient $\epsilon$>

One milligram of each of compound 1 and comparative compounds 1 and 2 was dissolved in 100 mL of the solvent, and the solution was examined for absorption spectrum with Hitachi Spectrophotometer U-4100 using a quartz cell having a measuring optical-path length of 10 mm. From the spectrum obtained, the absorption maximum wavelength $\lambda_{max}$ (nm) and the molar extinction coefficient E (L·mol$^{-1}$·cm$^{-1}$) were determined.

<Method of Determining Solubility C and $\epsilon$C>

The solubility C of each compound in n-decane was determined in the following manner. Each of compounds 1 to 11 and comparative compound 1 was added to n-decane until some of the compound came to remain undissolved, and the mixture was subjected to an ultrasonic treatment at 30° C. for 30 minutes. Compounds 1, 3 to 5, and 11 were highly soluble and, hence, the addition thereof was stopped at the time when a specific solubility was ascertained.

After the addition, each mixture was subjected to a 30-minute ultrasonic treatment at 30° C. This mixture was allowed to stand at 5° C. for 24 hours and then subjected to centrifugal filtration with a 0.1-µm filter using a miniature centrifugal machine (centrifugal force, 5,200×g). The saturated solution obtained was diluted to an adequate concentration and examined for absorption spectrum with Hitachi Spectrophotometer U-4100 using a quartz cell having a measuring optical-path length of 10 mm. The concentration of each compound was determined from a relationship between the absorbance at the absorption maximum wavelength $\lambda_{max}$ (nm) and the molar extinction coefficient $\epsilon$ (L·mol$^{-1}$·cm$^{-1}$) determined beforehand, and the solubility C (mol·L$^{-1}$) thereof was calculated. Furthermore, the product $\epsilon$C of the molar extinction coefficient $\epsilon$ (L·mol$^{-1}$·cm$^{-1}$) and the solubility C (mol·L$^{-1}$) was determined.

TABLE 4

| Compound | Color tone | Absorption maximum wavelength $\lambda_{max}$ (nm) | Solubility C (mass %) | $\epsilon$ (L · mol$^{-1}$ · cm$^{-1}$) | $\epsilon$C (cm$^{-1}$) |
|---|---|---|---|---|---|
| Compound 1 | blue | 617 | ≥28.8 | 70000 | ≥20000 |
| Compound 2 | blue | 608 | 1.7 | 62000 | 1220 |
| Compound 3 | blue | 617 | ≥34.3 | 70000 | ≥20000 |
| Compound 4 | blue | 638 | ≥10.5 | 54000 | ≥6000 |
| Compound 5 | blue | 591 | ≥20.1 | 50000 | ≥10000 |
| Compound 6 | blue | 575 | 5.2 | 55000 | 3100 |
| Compound 7 | blue | 590 | 17.4 | 51000 | 9500 |
| Compound 8 | blue | 591 | ≥11.0 | 52000 | ≥6000 |
| Compound 9 | blue | 653 | 33.9 | 65000 | 22000 |
| Compound 10 | blue | 595 | ≥15 | 57000 | ≥9000 |
| Compound 11 | blue | 595 | ≥19.7 | 59000 | ≥12000 |
| Comparative compound 1 | red | 526 | 9.1 | 50000 | 4700 |

<Method of Light Fastness Test>

The light fastness of compounds 1 to 3, 5, and 7 to 11 and comparative compound 1 was determined in the following manner. In 0.99 g of n-decane was dissolved 0.01 of each compound. This solution was introduced into a cell having an optical-path length of 0.004 mm, and this cell was sealed with an epoxy resin. Using a weatherometer (Atlas Ci4000), the cell was irradiated with xenon light (340 nm; irradiance, 0.55 W/m$^2$) for 40 hours. During the irradiation, the internal temperature of the test chamber was kept at 33° C.

The retention of each compound was calculated using the following equation. The compounds which had a retention of 100-90% were rated as A, those having a retention of 89-80% as B, those having a retention of 80-50% as C, and those having a retention of 49% or less as D.

*Retention (%)=(absorbance at absorption maximum wavelength after irradiation)/(absorbance at absorption maximum wavelength before irradiation)×100

The results of the light fastness test are summarized in Table 5 below.

TABLE 5

| Compound | Light fastness |
|---|---|
| Compound 1 | A |
| Compound 2 | A |
| Compound 3 | A |
| Compound 4 | A |
| Compound 5 | A |
| Compound 6 | A |
| Compound 7 | A |
| Compound 8 | A |
| Compound 9 | A |
| Compound 10 | A |
| Compound 11 | A |
| Comparative compound 1 | D |

<Preparation of Black Inks>

Composition 1, which was composed of compound 3 and the yellow compound A, red compound A, and blue compound A that are described below, was dissolved in n-decane (relative permittivity, 2.0; solubility in water, 1 mg/L or less; manufactured by Tokyo Kasei Kogyo Co., Ltd.) to prepare black ink 1 in accordance with Table 6. Furthermore, composition 2, which was composed of compound 10 and the yellow compound A, red compound A, and blue compound A that are described below, and composition 3, which was composed of the yellow compound A, red compound A, and blue compound A that are described below, were each dissolved in the same n-decane as in the case of composition 1 to prepare black ink 2 and a comparative black ink in accordance with Table 6.

Incidentally, when the black inks 1 and 2 and comparative black ink were prepared, the addition amounts of the compounds were regulated so as to result in an optical density (OD), measured at an optical-path length of 0.010 mm, of 2.7.

TABLE 6

| | | Compound 3 (g) | Compound 10 (g) | Yellow compound A (g) | Red compound A (g) | Blue compound A (g) | Total weight of compounds (g) | n-Decane (g) |
|---|---|---|---|---|---|---|---|---|
| Black ink 1 | composition 1 | 0.035 | — | 0.083 | 0.052 | 0.226 | 0.396 | 1.604 |
| Black ink 2 | composition 2 | — | 0.035 | 0.084 | 0.044 | 0.229 | 0.392 | 1.608 |
| Comparative black ink | composition 3 | — | — | 0.0956 | 0.05 | 0.356 | 0.502 | 1.498 |

115

<Yellow Compound A>

The compound (1-1) described in International Publication WO 2009/063880.

[Chem. 44]

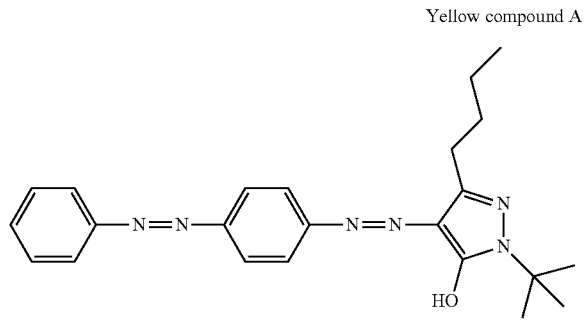

Yellow compound A

<Red Compound A>

A mixture of H-1 (0.50 g; 3.3 mmol), glacial acetic acid (3 mL), propionic acid (0.7 mL), sulfuric acid (2.7 mL), and desalted water (0.3 mL) was cooled with an ice bath, and 44 wt % nitrosylsulfuric acid (1.0 g; 3.6 mmol) was dropped thereinto at an internal temperature of 1° C. Thereafter, the resultant mixture was stirred for 1 hour while keeping the internal temperature at 0±5° C., thereby obtaining a diazotization solution. Intermediate CP1 (0.81 g; 3.1 mmol), tetrahydrofuran (40 mL), sulfamic acid (0.06 g; 0.6 mmol), and sodium acetate (5.7 g) were introduced into another vessel, and the diazotization solution was dropped thereinto while keeping the internal temperature at 0±5° C. with cooling with ice.

In the course of the dropping, ice and tetrahydrofuran (40 mL) were added. After completion of the dropping, the pH was adjusted to 4 by adding an aqueous sodium acetate solution. This mixture was extracted with toluene, and the extract was concentrated under vacuum and purified by silica gel column chromatography. The solid yielded was washed with methanol/water (1/1 (by volume)). Thus, red compound A (0.45 g; yield, 32%) was synthesized.

[Chem. 45]

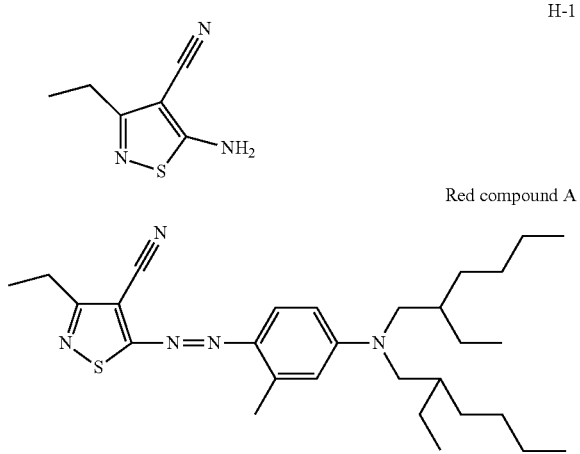

H-1

Red compound A

116

<Blue Compound A>

The compound described in JP-A-2000-313174.

[Chem. 46]

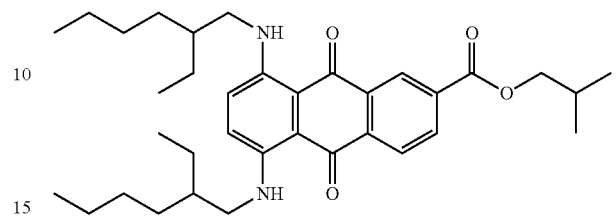

Blue compound A

<Hue Evaluation>

The black inks and the comparative ink were each examined for spectrum using a cell having a measuring optical-path length of 0.01 mm. The hue thereof was quantitatively evaluated by conducting a color measurement using the color calculation program which belonged to the Hitachi Spectrophotometer U-4100, under the conditions of illuminant D65 and a viewing angle of 2 degrees. The results of the hue evaluation of black ink 1 and the comparative ink are shown in Table 7.

<Viscosity Measurement>

Black inks 1 and 2 and the comparative black ink were examined for viscosity at 25° C. using a rotational viscometer (BROOKFIELD LV-1). The results of the measurement are shown in Table 7.

TABLE 7

| | Measuring optical-path length (mm) | Results of hue evaluation | | | | |
|---|---|---|---|---|---|---|
| | | $L^*$ | $a^*$ | $b^*$ | $C^*$ | OD |
| Black ink 1 | 0.01 | 1.33 | 0.38 | 0.08 | 0.4 | 2.7 |
| Black ink 2 | 0.01 | 1.78 | −0.33 | 0.27 | 0.4 | 2.7 |
| Comparative black ink | 0.01 | 1.94 | −0.21 | 1.79 | 1.8 | 2.7 |

Although equal in OD to the comparative black ink, black inks 1 and 2 each had a small value of $L^*$ and a value of $C^*$ of 1 or less. Black inks 1 and 2 were found to be satisfactory black inks having an excellent black hue. Black inks 1 and 2 further had a lower ink viscosity than the comparative ink, and were found to be inks having excellent properties.

While the invention has been described in detail and with reference to specific embodiments thereof, it will be apparent to one skilled in the art that various changes and modifications can be made therein without departing from the spirit and scope thereof. This application is based on a Japanese patent application filed on Nov. 28, 2012 (Application No. 2012-260019) and a Japanese patent application filed on Nov. 28, 2012 (Application No. 2012-260020), the entire contents thereof being incorporated herein by reference.

The invention claimed is:

1. An ink comprising: a solvent having a relative permittivity, measured at a frequency of 1 kHz and a temperature of 22° C., of 3 or less and a solubility in water at 25° C. of 20 mg/L or less; and an azo compound represented by the following general formula (1):

(1)

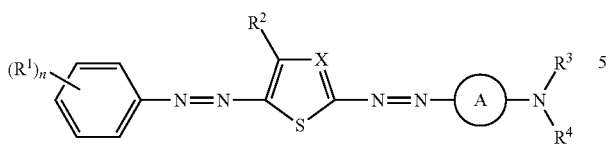

wherein in the general formula (1),
$R^1$ represents any substituent,
$R^2$ represents a hydrogen atom or any substituent,
$R^3$ and $R^4$ each independently represent an alkyl group which may have a substituent, ring A represents general formula (2),
X represents a nitrogen atom, a methine group, or a methine group having a substituent, and general formula (2) is represented by the following formula:

(2)

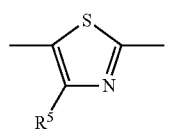

wherein in the general formula (2),
$R^5$ represents a hydrogen atom or any substituent (3)

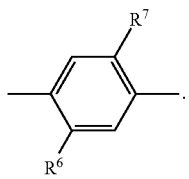

2. The ink according to claim 1, wherein the solvent comprises at least one member selected from the group consisting of hydrocarbon-based solvents, silicone oils, and fluorocarbon-based solvents.

3. The ink according to claim 1, wherein a product $\epsilon C$ of a molar extinction coefficient $\epsilon$ ($Lmol^{-1}\ cm^{-1}$) at an absorption maximum wavelength in an n-decane solution of the azo compound and a saturation concentration C ($molL^{-1}$) at 5° C. of the solution is 1,000 $cm^{-1}$ or larger.

4. The ink according to claim 1, which further comprises at least one member selected from the group consisting of heterocyclic compounds, cyanovinyl compounds, and anthraquinone compounds.

5. The ink according to claim 4, wherein the heterocyclic compounds are at least one compound selected from the group consisting of the following general formulae (4) to (7):

(4)

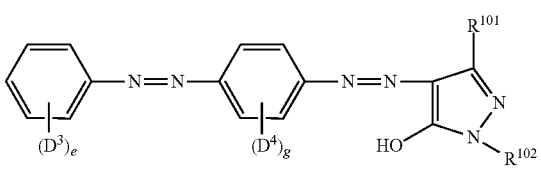

wherein in the general formula (4),
$R^{101}$ and $R^{102}$ each independently represent a hydrogen atom or any substituent,
$D^3$ and $D^4$ each independently represent any substituent,
e represents an integer of 0-5, and when e is 2 or larger, the two or more $D^3$s present in the molecule may be the same or different, and
g represents an integer of 0-4, and when g is 2 or larger, the two or more $D^4$s present in the molecule may be the same or different;

(5)

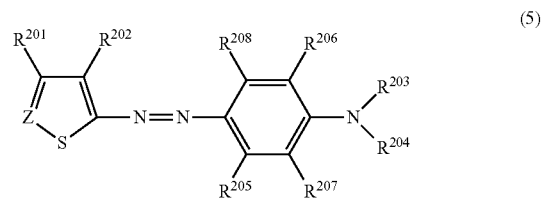

wherein in the general formula (5), $R^{201}$, $R^{202}$, $R^{203}$, $R^{204}$, $R^{205}$, $R^{206}$, $R^{207}$, and $R^{208}$ each independently represent a hydrogen atom or any substituent, and
Z represents a nitrogen atom, a methine group or a methine group having a substituent;

(6)

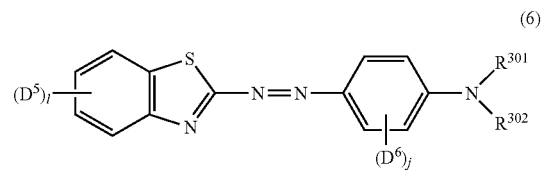

wherein in the general formula (6),
$R^{301}$, $R^{302}$, $D^5$, and $D^6$ each independently represent any substituent,
l represents an integer of 0-4, and when l is 2 or larger, the two or more $D^5$s present in the molecule may be the same or different, and
j represents an integer of 0-4, and when j is 2 or larger, the two or more $D^6$s present in the molecule may be the same or different;

(7)

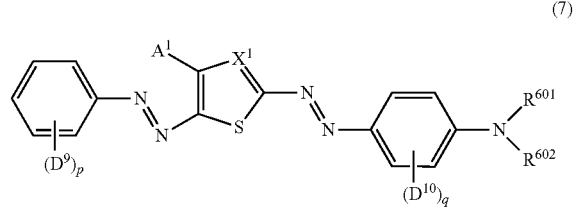

wherein in the general formula (7), $R^{601}$, $R^{602}$, $D^9$, or $D^{10}$ each independently represents any substituent,
$A^1$ represents a hydrogen atom or any substituent,
p represents an integer of 0-5, and when p is 2 or larger, the two or more $D^9$s present in the molecule may be the same or different,
q represents an integer of 0-4, and when q is 2 or larger, the two or more $D^{10}$s present in the molecule may be the same or different,
$X^1$ represents a nitrogen atom, a methine group, or a methine group having a halogen atom, a cyano group, or a —$COOR^{605}$ group as a substituent, and $R^{605}$ represents a hydrogen atom, an alkyl group which has 1-20 carbon atoms and may have a substituent, an aryl group which has 6-20 carbon atoms and may have a substituent, or a heteroaryl group which has 2-20 carbon atoms and may have a substituent.

6. The ink according to claim 4, wherein the anthraquinone compounds are represented by the following general formula (8):

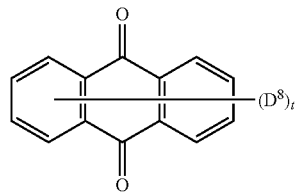
(8)

wherein in the general formula (8), $D^8$ represents any substituent, and t represents an integer of 0-8, and when t is 2 or larger, the two or more $D^8$s present in the molecule may be the same or different.

7. The ink according to claim 1, which is for displays or for optical shutters.

8. A display which comprises a display part including the ink according to claim 1, wherein an image is displayed by controlling voltage application to the display part.

9. The display according to claim 8, wherein the display part includes electrophoretic particles or an aqueous medium.

10. The display according to claim 8, wherein an image is displayed by causing a change in the coloration state by the voltage application.

11. The display according to claim 8, wherein an image is displayed in an electrowetting mode or an electrophoresis mode.

12. An electronic paper which comprises the display according to claim 8.

13. An azo compound represented by the following general formula (10):

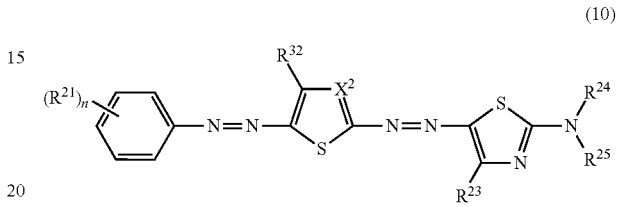
(10)

wherein in the general formula (10), $R^{21}$ represents any substituent, $R^{22}$ and $R^{23}$ each independently represent a hydrogen atom or any substituent, $R^{24}$ and $R^{25}$ each independently represent an alkyl group which may have a substituent, $X^2$ represents a nitrogen atom or a methine group which may have a substituent, and n' represents an integer of 0-5.

* * * * *